United States Patent
Cham

(10) Patent No.: US 7,439,052 B2
(45) Date of Patent: Oct. 21, 2008

(54) METHOD OF MAKING MODIFIED IMMUNODEFICIENCY VIRUS PARTICLES

(75) Inventor: Bill E. Cham, Sheldon (AU)

(73) Assignee: Lipid Sciences, Pleasanton, CA (US)

( * ) Notice: Subject to any disclaimer, the term of this patent is extended or adjusted under 35 U.S.C. 154(b) by 10 days.

(21) Appl. No.: 11/401,434

(22) Filed: Apr. 10, 2006

(65) Prior Publication Data

US 2007/0031923 A1    Feb. 8, 2007

Related U.S. Application Data

(63) Continuation-in-part of application No. 10/873,015, filed on Jun. 21, 2004, now Pat. No. 7,407,662, which is a continuation-in-part of application No. 10/601,656, filed on Jun. 20, 2003, now Pat. No. 7,407,663, which is a continuation-in-part of application No. 10/311,679, filed as application No. PCT/IB01/01099 on Jun. 21, 2001, now abandoned.

(60) Provisional application No. 60/670,574, filed on Apr. 11, 2005, provisional application No. 60/669,738, filed on Apr. 8, 2005, provisional application No. 60/390,066, filed on Jun. 20, 2002, provisional application No. 60/491,928, filed on Aug. 1, 2003, provisional application No. 60/533,542, filed on Dec. 31, 2003, provisional application No. 60/542,947, filed on Feb. 9, 2004.

(30) Foreign Application Priority Data

Jun. 29, 2000    (AU) ...................................... PQ8469
Dec. 28, 2000    (WO) .................... PCT/AU00/01603

(51) Int. Cl.
C12N 7/00    (2006.01)
A61K 39/21    (2006.01)

(52) U.S. Cl. ................................. 435/235.1; 424/208.1

(58) Field of Classification Search ........................ None
See application file for complete search history.

(56) References Cited

U.S. PATENT DOCUMENTS

| | | | |
|---|---|---|---|
| 3,647,624 A | 3/1972 | Evenson | |
| 3,958,939 A | 5/1976 | Jones | |
| 3,983,008 A | 9/1976 | Shinozaki et al. | |
| 3,989,466 A | 11/1976 | Pan | |
| 4,025,423 A | 5/1977 | Stonner et al. | |
| 4,103,685 A | 8/1978 | Lupien et al. | |
| 4,124,509 A | 11/1978 | Iijima et al. | |
| 4,234,317 A | 11/1980 | Lucas et al. | |
| 4,235,602 A | 11/1980 | Meyer et al. | |
| 4,258,010 A | 3/1981 | Rozsa et al. | |
| 4,350,156 A | 9/1982 | Malchesky et al. | |
| 4,391,711 A | 7/1983 | Jackson et al. | |
| 4,399,217 A | 8/1983 | Holmquist et al. | |
| 4,402,940 A | 9/1983 | Nose et al. | |
| 4,431,633 A | 2/1984 | Machlowitz et al. | |
| 4,435,289 A | 3/1984 | Breslau | |
| 4,463,988 A | 8/1984 | Bouck et al. | |
| 4,481,189 A | 11/1984 | Prince | |
| 4,522,809 A | 6/1985 | Adamowicz et al. | |
| 4,540,401 A | 9/1985 | Marten | |
| 4,540,573 A | 9/1985 | Neurath et al. | |
| 4,581,231 A | 4/1986 | Purcell et al. | |
| 4,591,505 A | 5/1986 | Prince | |
| 4,605,648 A | 8/1986 | Price | |
| 4,613,501 A | 9/1986 | Horowitz | |
| 4,615,886 A | 10/1986 | Purcell et al. | |
| 4,643,718 A | 2/1987 | Marten | |
| 4,645,512 A | 2/1987 | Johns | |
| 4,647,280 A | 3/1987 | Maaskant et al. | |
| 4,648,974 A | 3/1987 | Rosskopf et al. | |
| 4,668,398 A | 5/1987 | Silvis | |

(Continued)

FOREIGN PATENT DOCUMENTS

CA    1271708    7/1990

(Continued)

OTHER PUBLICATIONS

Desombere, I. et al., Partial Delipidation Improves the T-Cell Antigenicity of Hepatitis B Virus Surface Antigen, *Journal of Virology*, 2006, vol. 80, No. 7, pp. 3506-3514.

(Continued)

*Primary Examiner*—Stacy B Chen
(74) *Attorney, Agent, or Firm*—Kilpatrick Stockton LLP

(57) ABSTRACT

Described are a composition and method for reducing the occurrence and severity of infectious diseases, especially infectious diseases in which lipid-containing infectious viral organisms are found in biological fluids, such as blood. Solvents useful for extracting lipids from lipid-containing infectious viral organisms are employed thereby creating immunogenic modified, partially delipidated viral particles with reduced infectivity. Provided are delipidated viral vaccine compositions, such as therapeutic vaccine compositions, comprising these modified, partially delipidated viral particles with reduced infectivity, optionally combined with a pharmaceutically acceptable carrier or an immunostimulant. The vaccine composition is administered to a patient to provide protection against a lipid-containing infectious viral organism or, as a therapeutic vaccine, to treat or alleviate infection by the lipid-containing infectious viral organism. The vaccine compositions of the present invention include combination vaccines of modified viral particles obtained from one or more strains of a virus and/or one or more types of virus.

20 Claims, 34 Drawing Sheets

U.S. PATENT DOCUMENTS

| | | |
|---|---|---|
| 4,671,909 A | 6/1987 | Torobin |
| 4,676,905 A | 6/1987 | Nagao et al. |
| 4,677,057 A | 6/1987 | Curtiss et al. |
| 4,680,320 A | 7/1987 | Uku et al. |
| 4,696,670 A | 9/1987 | Ohnishi et al. |
| 4,775,483 A | 10/1988 | Mookerjea et al. |
| 4,832,034 A | 5/1989 | Pizziconi et al. |
| 4,836,928 A | 6/1989 | Aoyagi et al. |
| 4,879,037 A | 11/1989 | Utzinger |
| 4,895,558 A | 1/1990 | Cham |
| 4,908,354 A | 3/1990 | Seidel et al. |
| 4,909,940 A | 3/1990 | Horowitz et al. |
| 4,909,942 A | 3/1990 | Sato et al. |
| 4,923,439 A | 5/1990 | Siedel et al. |
| 4,935,204 A | 6/1990 | Seidel et al. |
| 4,966,709 A | 10/1990 | Nose et al. |
| 4,970,144 A | 11/1990 | Fareed et al. |
| 5,026,479 A | 6/1991 | Bikson et al. |
| 5,080,796 A | 1/1992 | Nose et al. |
| 5,089,602 A | 2/1992 | Isliker et al. |
| 5,112,956 A | 5/1992 | Tang et al. |
| 5,116,307 A | 5/1992 | Collins |
| 5,126,240 A | 6/1992 | Curtiss |
| 5,128,318 A | 7/1992 | Levine et al. |
| 5,151,023 A | 9/1992 | Kuzuhara et al. |
| 5,152,743 A | 10/1992 | Gorsuch et al. |
| 5,187,010 A | 2/1993 | Parham et al. |
| 5,203,778 A | 4/1993 | Boehringer |
| 5,211,850 A | 5/1993 | Shettigar et al. |
| 5,236,644 A | 8/1993 | Parham et al. |
| 5,256,767 A | 10/1993 | Salk et al. |
| 5,258,149 A | 11/1993 | Parham et al. |
| 5,279,540 A | 1/1994 | Davidson |
| 5,301,694 A | 4/1994 | Raymond et al. |
| 5,354,262 A | 10/1994 | Boehringer et al. |
| 5,391,143 A | 2/1995 | Kensey |
| 5,393,429 A | 2/1995 | Nakayama et al. |
| 5,401,415 A | 3/1995 | Rauh et al. |
| 5,401,466 A | 3/1995 | Foltz et al. |
| 5,418,061 A | 5/1995 | Parham et al. |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham et al. |
| 5,523,096 A | 6/1996 | Okarma et al. |
| 5,565,203 A | 10/1996 | Gluck et al. |
| 5,634,893 A | 6/1997 | Rishton |
| 5,637,224 A | 6/1997 | Sirkar et al. |
| 5,652,339 A | 7/1997 | Lerch et al. |
| 5,679,260 A | 10/1997 | Boos et al. |
| 5,698,432 A | 12/1997 | Oxford |
| 5,707,673 A | 1/1998 | Prevost et al. |
| 5,719,194 A | 2/1998 | Mann et al. |
| 5,744,038 A | 4/1998 | Cham |
| 5,753,227 A | 5/1998 | Strahilevitz |
| 5,834,015 A | 11/1998 | Oleske et al. |
| 5,853,725 A | 12/1998 | Salk et al. |
| 5,855,782 A | 1/1999 | Falkenhagen et al. |
| 5,858,238 A | 1/1999 | McRea et al. |
| 5,877,005 A | 3/1999 | Castor |
| 5,879,685 A | 3/1999 | Gluck et al. |
| 5,885,578 A | 3/1999 | Salk et al. |
| 5,891,432 A | 4/1999 | Hoo |
| 5,895,650 A | 4/1999 | Salk et al. |
| 5,911,698 A | 6/1999 | Cham |
| 5,916,806 A | 6/1999 | Salk et al. |
| 5,919,369 A | 7/1999 | Ash |
| 5,928,930 A | 7/1999 | Salk et al. |
| 5,948,441 A | 9/1999 | Lenk et al. |
| 5,962,322 A | 10/1999 | Kozarsky et al. |
| 5,980,478 A | 11/1999 | Gorsuch et al. |
| 6,004,925 A | 12/1999 | Dasseux et al. |
| 6,017,543 A | 1/2000 | Salk et al. |
| 6,022,333 A | 2/2000 | Kensey |
| 6,037,323 A | 3/2000 | Dasseux et al. |
| 6,037,458 A | 3/2000 | Hirai et al. |
| 6,039,946 A | 3/2000 | Strahilevitz |
| 6,046,166 A | 4/2000 | Dasseux et al. |
| 6,080,778 A | 6/2000 | Yankner et al. |
| 6,127,370 A | 10/2000 | Smith et al. |
| 6,136,321 A | 10/2000 | Barrett et al. |
| 6,139,746 A | 10/2000 | Kopf |
| 6,156,727 A | 12/2000 | Garber et al. |
| 6,165,502 A | 12/2000 | Oleske et al. |
| 6,171,373 B1 | 1/2001 | Park et al. |
| 6,193,891 B1 | 2/2001 | Kent et al. |
| 6,264,623 B1 | 7/2001 | Strahilevitz |
| 6,309,550 B1 | 10/2001 | Iverson et al. |
| 6,337,368 B1 | 1/2002 | Kobayashi et al. |
| 6,369,048 B1 | 4/2002 | Budowsky et al. |
| 6,440,387 B1 | 8/2002 | Yankner et al. |
| 6,472,421 B1 | 10/2002 | Wolozin |
| 6,605,588 B1 | 8/2003 | Lees et al. |
| 6,706,008 B2 | 3/2004 | Vishnoi et al. |
| 6,737,066 B1 | 5/2004 | Moss |
| 2001/0028895 A1 | 10/2001 | Bisgaier et al. |
| 2002/0055529 A1 | 5/2002 | Bisgaier et al. |
| 2002/0081263 A1 | 6/2002 | Yankner et al. |
| 2002/0107173 A1 | 8/2002 | Friedhoff et al. |
| 2002/0128227 A1 | 9/2002 | Hildreth |
| 2002/0183379 A1 | 12/2002 | Yankner et al. |
| 2002/0188012 A1 | 12/2002 | Bisgaier et al. |
| 2003/0018013 A1 | 1/2003 | Dasseux et al. |
| 2003/0044428 A1 | 3/2003 | Moss |
| 2003/0119782 A1 | 6/2003 | Cham |
| 2003/0133929 A1 | 7/2003 | Cham |
| 2004/0170649 A1 | 9/2004 | Cham et al. |
| 2005/0032222 A1 | 2/2005 | Cham et al. |
| 2007/0212376 A1 | 9/2007 | Cham |

FOREIGN PATENT DOCUMENTS

| | | |
|---|---|---|
| CN | 1189378 | 8/1998 |
| DE | 29 44 138 A1 | 6/1981 |
| DE | 31 18 072 A1 | 11/1982 |
| DE | 32 13 390 A1 | 10/1983 |
| DE | 33 10 263 A1 | 9/1984 |
| EP | 0 036 283 A2 | 9/1981 |
| EP | 0 267 471 A1 | 5/1988 |
| FR | 2 571 971 A1 | 4/1986 |
| JP | 127104 | 1/1980 |
| JP | 277303 | 10/1993 |
| SU | 1116396 A | 9/1984 |
| SU | 1204224 A | 1/1986 |
| SU | 1752187 A3 | 7/1992 |
| WO | WO 88/09345 A1 | 12/1988 |
| WO | WO 95/03840 A1 | 2/1995 |
| WO | WO 99/38498 A1 | 8/1999 |
| WO | WO 01/45718 | 6/2001 |
| WO | WO 01/56579 A1 | 8/2001 |
| WO | WO 02/10768 A3 | 2/2002 |
| WO | WO 02/30863 A2 | 4/2002 |
| WO | WO 02/062824 A2 | 8/2002 |

OTHER PUBLICATIONS

Agnese, S.T., et al., "Evaluation of Four Reagents for Dilipidation of Serum," Clin Biochem., (Apr. 1983) vol. 16, No. 2, pp. 98-100.

Albouz, et al., Ann. Biol. Clin., Extraction of Plasma Lipids Preserving Antigenic Properties of Proteins and Allowing Quantitation of Gangliosides by Neuraminic Acid Determination, 37, 287-290. (abstract only) (1979).

Andre et al., Journal of Virology, Characterization of Low- and Very-Low-Density Hepatitis C Virus RNA-Containing Particles, 76 (14), 6919-6928. (Jul. 2002).

Asztalos et al., Arterioscler. Thromb. Vasc. Biol., Distribution of Apo A-I-Containing HDL Subpopulations in Patients with Coronary Heart Disease, 2670-2676. (Dec. 1, 2000).

Asztalos et al., Arterioscler. Thromb. Vasc. Biol., Presence and Formation of 'Free Apolipoprotein A-I-Like' Particles in Human Plasma, 15, 1419-1423. (1995).

Asztalos et al., Arterioscler. Thromb. Vasc. Biol., Role of Free Apolipoprotein A-I in Cholesterol Efflux, 17, 1630-1636. (1997).

Badimon, et al., Laboratory Investigation, High Density Lipoprotein Plasma Fractions Inhibit Aortic Fatty Streaks in Cholesterol-Fed Rabbits, 60, 455-461. (1989).

Badimon, et al., J. Clinical Investigation, Regression of Atherosclerotic Lesions by High Density Lipoprotein Plasma Fraction in the Cholesterol-Fed Rabbit, 85, 1234-1241. (1990).

Barbara, The Rationale for Pathogen-Inactivation Treatment of Blood Components, Int. J. Hematol, vol. 80, pp. 311-316, 2004.

Barouch, et al., Nature (2002), vol. 415, pp. 335-339.

Barrans et al., Biochimica et Biophysica Acta, Pre-β HDL: Structure and Metabolism, 1300, 73-85. (1996).

Barres et al., Science, Cholesterol—Making or Breaking the Synapse, 294, 1296/1297. (Nov. 9, 2001).

Bloom, et al., Clin. Biochem., Quantitation of lipid profiles from isolated serum lipoproteins using small volumes of human serum, 14, 119-125. (abstract only) (Jun. 1981).

Burns et al., Neurochem Res, Use of In Vivo Models to Study the Role of Cholesterol in the Etiology of Alzheimer's Disease 28, 979-86. (abstract only) (Jul. 2003).

Cham, Clinical Chemistry, Nature of the Interaction Between Low-Density Lipoproteins and Polyanions and Metal Ions, as Exemplified by Heparin and $Ca^{2+}$, 22, 1812-1816. (1976).

Cham, et al., Clinical Chemistry, Changes in Electrophoretic Mobilities of α- and β-Lipoproteins as a Result of Plasma Delipidation, 22, 305-309. (1976).

Cham, et al., Biochemical and Biophysical Research Communications, Heterogeneity of Lipoprotein B, 103, 196-206 (1981).

Cham, et al., Chem. Biol. Interactions, Importance of Apolipoproteins in Lipid Metabolism, 20, 263-277. (1978).

Cham, et al., J. Biol. Chem., In Vitro Partial Relipidation of Apolipoproteins in Plasma, 251, 6367-6371. (abstract only) (1976).

Cham, et al., Pharmacol. (Life Sci. Adv.), Lipid Apheresis in an Animal Model Causes Acute Reduction in plasma Lipid Concentrations and Mobilisation of Lipid from Liver and Aorta, 13, 25-32. (1994).

Cham, et al., J. Clin. Apheresis, Lipid Apheresis in an Animal Model Causes In Vivo Changes ini Lipoprotein Electrophoretic Patterns, 11, 61-70. (1996).

Cham, et al., Clinical Chemistry, Phospholipids in EDTA—Treated Plasma and Serum, 39, 2347-2348. (1993).

Cham, et al., 59th Congress European Atherosclerosis Society, Nice, France, Rapid Regression of Atherosclerosis by Cholesterol Apheresis—A Newly Developed Technique, 17-21. (abstract only) (May 1992).

Cham, et al., Clinica Chimica Acta, Rapid, Sensitive Method for the Separation of Free Cholesterol from Ester Cholesterol, 49, 109-113. (1973).

Cham, Bill E., et al., "A solvent system for delipidation of plasma or serum without protein precipitation," Journal of Lipid Research, vol. 17, 1976, pp. 176-181.

Cham et al., Journal of Biological Chemistry, Differential Effects of Lecithin and Cholesterol on the Immunoreactivity and Confirmation of Apolipoprotein A-I in High Density Lipoproteins, 266 (14), 9145-9152. (May 15, 1991).

Cham, Bill E., et al., "Lipid Apheresis: An In Vivo Application of Plasma Delipidation with Organic Solvents Resulting in Acute Transient Reduction of Circulating Plasma Lipids in Animals," Journal of Clinical Apheresis, vol. 10, 1995, pp. 61-69.

Collet et al., Journal of Biological Chemistry, Differential Effects of Lecithin and Cholesterol on the Immunoreactivity and Confirmation of Apolipoprotein A-I in High Density Lipoproteins, 266 (14), 9145-9152. (May 15, 1991).

Cooper, Drugs Aging, Dietary Lipids in the Aetiology of Alzheimer's Disease: Implications for Therapy, 20 (6), 399-418. (abstract only) (2003).

Cruzado et al., Analytical Biochemistry, Characterization and Quantitation of the Apoproteins of High-Density Lipoprotein by Capillary Electrophoresis, 14 (7), 100-109. (1996).

Daughaday, W.H. et al., "Comparisons of serologic and febrile responses in humans to vaccination with influenza A viruses or their hemagglutinins," The Journal of Laboratory and Clinical Medicine, vol. 63, No. 1, Jan.-Jun. 1964, pp. 5-13.

Desombre,I. et al., Partial Delipidation Improves the T-Cell Antigenicity of Hepatitis B Virus Surface Antigen, Journal of Virology, 2006, vol. 80, No. 7, pp. 3506-3514.

Desrosiers, Prospects for an AIDS Vaccine, Nature Medicine, 2004, vol. 10, No. 3, pp. 221-223.

Deva, A.K., et al., "Establishment of an in-use testing method for evaluating disinfection of surgical instruments using the duck hepatitis B model," J. Hosp. Infect., (Jun. 1996), vol. 22, No. 2, pp. 119-130, Abstract only.

Dwivedy, 18th Australian Atherosclerosis Society Conference, Surfers Paradise, Increase of Reverse Cholesterol Transport by Cholesterol Apheresis Regression of Atherosclerosis, 21. (1992).

Eisenhauer, et al, Klin Wochenschr (KWH), Selective Removal of Low Density Lipoproteins (LDL) by Precipitation at Low pH: First Clinical Application of the Help System, 65, 161-168. (1987).

Erlich, KS, Herpes Simplex Virus and HIV, on HIV InSite, http://hivinsite.ucsf.edu/InSite?page=kb-05-03-02. 21 pages, 2002.

Fang, et al., 18th Australian Atherosclerosis Society Conference, Gold Coast, Australia, In Vivo Rapid Mobilization of Adipose Tissue by Lipid Apheresis—A Newly Developed Technique. (1992).

Feinberg et al. AIDS Vaccine Models: Challenging Challenge Viruses, Nature Medicine, 2002, vol. 8, No. 3, pp. 207-210.

Feinstone, Stephen M., et al., "Inactivation of Hepatitis B Virus and Non-A, Non-B Hepatitis by Chloroform," Infection and Immunity, Aug. 1983, vol. 41, No. 2, pp. 816-821.

Golde et al., Drug Discovery Today, Cholesterol Modulation as an Emerging Strategy for the Treatment of Alzheimer's Disease, 6 (20), 1049-1055. (abstract only) (Oct. 15, 2001).

Hatch et al., Lipoprotein Analysis, Advances in Lipid Research, Practical Methods for Plasma Lipoprotein Analysis, 6, 1-68. (1968).

Higleyman, The Search for an HCV Vaccine, HCV Advocate, Monthly Newsletter, Oct. 2003, vol. 5, Issue 10, pp. 109, http://www.hcvadvocate.org.

Horowitz, B., et al., "Viral safety of solvent/detergent-treated blood products," Blood Coagulation and Fibrinolysis, vol. 5, Supp. 3, 1994, pp. S21-S28.

Innerarity, et al., Biochemistry, Enhanced Binding by Cultured Human Fibroblasts of Apo-E-Containing Lipoproteins as Compared with Low Density Lipoproteins, 17, 1440-1447. (1978).

Ito, J., et al., "Cholesterol-Sphingomyelin Interaction in Membrane and Apolipoprotein-Medicated Cellular Cholesterol Efflux", J. of Lipid Research, Jun. 2000, pp. 894-904, vol. 41.

Jackson et al., Biochimica et Biophysica Acta, Isolation and Characterization of the Major Apolipoprotein from Chicken High Density Lipoproteins, 420, 342-349. (1976).

Klimov, A.N. et al., "Extraction of Lipids from Blood Plasma and Subsequent Introduction of Autologous Delipidized Plasma into the Body as a Possible Means to Treat Atherosclerosis", Russian Journal Kardiologiia, vol. 18, No. 6, pp. 23-29 (1978).

Koizumi, et al., J. Lipid Research, Behavior of Human Apolipoprotein A-1: Phospho-Lipid and apoHDL: Phospholipid Complexes In Vitro and After Injection into Rabbits, 29, 1405-1415. (1988).

Kostner, et al., XI Internet Symp. on Drugs Affecting Lipid Metabolism, Italy, Increase of APO A1 Concentration in Hypercholesteraemic Chickens after Treatment with a Newly Developed Extracorpreal Lipid Elimination. (May 13, 1992).

Kostner, et al., European Journal of Clinical Investigation, Lecithin-cholesterol acyltransferase activity in Normocholesterolaemic and Hypercholesterolaemic Roosters: Modulation by Lipid Apheresis, 27, 212-218. (May 7, 1997).

Koudinov et al., Clin Chim Acta, Alzheimer's Amyloid Beta Interaction with Normal Human Plasma High Density Lipoprotein: Association with Apolipoprotein and Lipids, 270 (2), 75-84. (abstract only) (Feb. 23, 1999).

Koudinov et al., Cell Biol Int., Alzheimer's Soluble Amyloid Beta Protein is Secreted by HepG2 Cells as an Apolipoprotein, 21 (5), 265-71. (abstract only) (May 1997).

Koudinov et al., Biochem Biophys Res Commun, Biochemical Characterization of Alzheimer's Soluble Amyloid Beta Protein in Human Cerebrospinal Fluid: Association with High Density Lipoproteins, 223 (3), 592-7. (abstract only) (Jun. 25, 1999).

Koudinov et al., Science, Cholesterol's Role in Synapse Formation, 294, 2213. (Nov. 9, 2001).

Koudinova et al., Soc. Neuroscience Abstract Viewer and Itinerary Planner, Amyloid Beta, Neural Lipids, Cholesterol and Alzheimer's Disease—Abstract No. 21.10. (2002).

Lipid Sciences, http://www.lipidsciences.com/technology.html, Lipid Technology, 1-4. (Aug. 25, 2001).

Lupien, et al., Lancet (LOS), A New Approach to the Management of Familial Hypercholesterolaemia: Removal of Plasma-Cholesterol Based on the Principle of Affinity Chromatography, 1, 1261-1265. (1976).

Mauch et al., Science, CNS Synaptogenesis Promoted by Glia-Derived Cholesterol, 294, 1354-1357. (Nov. 9, 2001).

Moya et al., Arteriosclerosis and Thrombosis, A Cell Culture System for Screening Human Serum for Ability to Promote Cellular Cholesterol Efflux, 14 (7), 1056-1065. (Jul. 1994).

Neurath, A. R. et al., "Properties of Delipidated Hepatitis B Surface Antigen (HbsAAg) and Preparation of its Proteolytic Cleavage Fragments Carrying HbsAg-Specific Antigenic Determinants," Intervirology, vol. 10, No. 5, 1978, pp. 265-275.

Ngu, V.A., "Chronic Infections from the Perspective of Evolution: a Hypothesis", *Medical Hypotheses*, vol. 42, pp. 81-88 (1994).

Ngu, V.A., "Human Cancers and Viruses: A Hypothesis for Immune Destruction of Tumours Caused by Certain Enveloped Viruses Using Modified Viral Antigens", *Medical Hypotheses*, vol. 39, pp. 17-21 (1992).

Ngu, V.A., "The viral envelope in the evolution of HIV: a hypothetical approach to inducing an effective immune response to the virus", *Medical Hypotheses*, vol. 48, pp. 517-521 (1997).

Okazaki et al., Journal of Chromatography, Biomedical Applications, Improved High-Performance Liquid Chromatographic Method for the Determination of Apolopoproteins in Serum High-Density Lipoproteins, 430, 135-142. (1988).

Thompson, et al., Lancet (LOS), Plasma Exchange in the Management of Homozygous Familial Hypercholesterolaemia, 1, 1208-1211. (1975).

Walker, et al. Nature, 2000, vol. 407, pp. 313-314.

Wikipedia.com entry for "Cell Membrane." http://en.wikipedia.org/wiki/Cell_membrane Accessed Feb. 14, 2006. 3 pages, 2006.

Williams et al., Biochim. Biophys. Act., Uptake of Endogenous Cholesterol by a Synthetic Lipoprotein , 875 (2), 183-194. (Feb. 12, 1986).

Williams, et al., Proc. Natl. Acad. Sci. USA, Low Density Lipoprotein Receptor-Independent Hepatic Uptake of a Synthetic, Cholesterol-Scavenging Lipoprotein: Implications for the Treatment of Receptor-Deficient Atherosclerosis, 85, 242-246. (1988).

Wong, et al, Journal of Lipid Research, Retention of gangliosides in serum delipidated by diisopropyl ether-1-butanol extraction, 24, 666-669. (1983).

Wormser, Henry, PSC3110—Fall Semester 2002, Lipids.

Yokoyama, et al., Arteriosclerosis, Selective Removal of Low Density Lipoprotein by Plasmapheresis in Familial Hypercholesterolemia, 5, 613-622. (1985).

Yoshidome et al., Artif Organs, Serum Amyloid A and P Protein Levels are Lowered by Dextran Sulfate Cellulose Low-Density Lipoprotein Apheresis, 22 (2), 144-148. (1998).

Zetia, http://www.zetia.com/ezetimbe/zetia/hcp/product_highlights/index.jsp, Zetia (ezetimibe), 1-2. (Jul. 18, 2003).

Zetia, http://www.zetia.com/ezetimibe/zetia.hcp/mechanism_of_action/index.jsp, Zetia: Complimentis Statin with a Unique Mechanism, 1-2. (Jul. 18, 2003).

Zhang et al., Journal of Lipid Research, Characterization of phospholipids in a pre-alpha HDL: Selective Phospholipid Efflux with Apolipoprotein A-I , 39, 1601-1607. (1998).

Parker, Thomas S., et al., "Plasma high density lipoprotein is increased in man when low density lipoprotein (LDL) is lowered by LDL-pheresis," Proc. Natl. Acad. Sci. USA, vol. 82, pp. 771-781, Feb. 1986.

Paterno et al., Cerebrovasc Dis., Reconstituted High-Density Lipprotein Exhibits Neuroprotection in Two Rat Models of Stroke, 17, 2-2, 204-11. (Abstract only) (Epub Dec. 29, 2003).

Refolo et al., Soc. Neuroscience Abstracts, Cholesterol Metabolism: A Potential Target for Alzheimer's Disease Therapy, 27 (2), 1518. (abstract only) (2001).

Robern et al., Experientia, The Application of Sodium Deoxycholate and Sephacryl-200 for the Delipidation and Separation of High Density Lipoproteins, 38, 437-439. (1982).

Ryan, et al., Clinical Chemistry, An Improved Extraction Procedure for the Determination of Triglycerides and Cholesterol in Plasma or Serum, 13, 769-772. (1967).

Scanu et al., Analytical Biochemistry, Solubility in Aqueous Solutions of Ethanol of the Small Molecular Weight Peptides of the Serum Very Low Density and High Density Lipoproteins: Relevance to the Recovery Problem During Delipidation of Serum Lipoproteins, 44, 576-588. (1971).

Segrest et al., Journal of Biological Chemsitry, A Detailed Molecular Belt Model for Apolipoprotein A-I in Discoidal High Density Lipoprotein, 274 (45), 31755-31758. (Nov. 5, 1999).

Slater, et al., J. of Lipid Research, A Comparison of Delipidated Sera Used in Studies of Sterol Synthesis by Human Mononuclear Leukocytes, 20, 413-416. (1979).

Slater, et al., Atherosclerosis, The Effect of Delipidated High Density Lipoprotein on Human Leukocyte Sterol Synthesis, 35, 41-49. (1980).

Stremlau, M. et al. The Cytoplasmic Body Component TRIMSalpha Restricts HIV-1 Infection in Old World Monkeys. Nature. vol. 427, pp. 848-853 (Feb. 26, 2004).

U.S. Appl. No. 12/118,263, unpublished; filed May 9, 2008, Cham et al.*

U.S. Appl. No. 12/118,409, unpublished; filed May 9, 2008, Cham et al.*

U.S. Appl. No. 12/118,335, unpublished; filed May 9, 2008, Cham et al.*

U.S. Appl. No. 12/106,201, unpublished; filed Apr. 18, 2008, Akeefe et al.*

U.S. Appl. No. 12/118,451, unpublished; filed May 9, 2008, Cham et al.*

* cited by examiner

SIVmac251 Gag p55 Antibody Titers of Mice
Immunized with AT-2 Treated Virus

```
                          SEQUENCE LISTING

<160> NUMBER OF SEQ ID NOS: 136

<210> SEQ ID NO 1
<211> LENGTH: 20
<212> TYPE: PRT
<213> ORGANISM: Artificial Sequence
<220> FEATURE:
<223> OTHER INFORMATION: Synthetic

<400> SEQUENCE: 1

Met Gly Val Arg Asn Ser Val Leu Ser Gly Lys Lys Ala Asp Glu Leu
1               5                   10                  15

Glu Lys Ile Arg
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Ser Gly Lys Lys Ala Asp Glu Leu Glu Lys Ile Arg Leu Arg Pro Asn
1               5                   10                  15

Gly Lys Lys Lys
            20

<210> SEQ ID NO 3
<211> LENGTH: 20
```

```
<212> TYPE: PRT
<213> ORGANISM: Artificial Sequence
<220> FEATURE:
<223> OTHER INFORMATION: Synthetic

<400> SEQUENCE: 3

Glu Lys Ile Arg Leu Arg Pro Asn Gly Lys Lys Tyr Met Leu Lys
1               5                   10                  15

His Val Val Trp
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Gly Lys Lys Lys Tyr Met Leu Lys His Val Val Trp Ala Ala Asn Glu
1               5                   10                  15

Leu Asp Arg Phe
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

His Val Val Trp Ala Ala Asn Glu Leu Asp Arg Phe Gly Leu Ala Glu
1               5                   10                  15

Ser Leu Leu Glu
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic

<400> SEQUENCE: 6

Leu Asp Arg Phe Gly Leu Ala Glu Ser Leu Leu Glu Asn Lys Glu Gly
1               5                   10                  15

Cys Gln Lys Ile
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic

<400> SEQUENCE: 7

Ser Leu Leu Glu Asn Lys Glu Gly Cys Gln Lys Ile Leu Ser Val Leu
1               5                   10                  15

Ala Pro Leu Val
            20

<210> SEQ ID NO 8
```

<211> LENGTH: 20
<212> TYPE: PRT
<213> ORGANISM: Artificial Sequence
<220> FEATURE:
<223> OTHER INFORMATION: Synthetic

<400> SEQUENCE: 8

Cys Gln Lys Ile Leu Ser Val Leu Ala Pro Leu Val Pro Thr Gly Ser
1               5                   10                  15

Glu Asn Leu Lys
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

Ala Pro Leu Val Pro Thr Gly Ser Glu Asn Leu Lys Ser Leu Tyr Asn
1               5                   10                  15

Thr Val Cys Val
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Glu Asn Leu Lys Ser Leu Tyr Asn Thr Val Cys Val Ile Trp Cys Ile
1               5                   10                  15

His Ala Glu Glu
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

Thr Val Cys Val Ile Trp Cys Ile His Ala Glu Glu Lys Val Lys His
1               5                   10                  15

Thr Glu Glu Ala
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

His Ala Glu Glu Lys Val Lys His Thr Glu Glu Ala Lys Gln Ile Val
1               5                   10                  15

Gln Arg His Leu
            20

```
<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

Thr Glu Glu Ala Lys Gln Ile Val Gln Arg His Leu Val Val Glu Thr
1               5                   10                  15

Gly Thr Thr

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Val Gln Arg His Leu Val Val Glu Thr Gly Thr Thr Glu Thr Met Pro
1               5                   10                  15

Lys Thr Ser Arg
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic

<400> SEQUENCE: 15

Gly Thr Thr Glu Thr Met Pro Lys Thr Ser Arg Pro Thr Ala Pro Ser
1               5                   10                  15

Ser Gly Arg Gly
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic

<400> SEQUENCE: 16

Thr Ser Arg Pro Thr Ala Pro Ser Ser Gly Arg Gly Gly Asn Tyr Pro
1               5                   10                  15

Val Gln Gln Ile
            20

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Ser Gly Arg Gly Gly Asn Tyr Pro Val Gln Gln Ile Gly Gly Asn Tyr
1               5                   10                  15

Val His Leu

<210> SEQ ID NO 18
```

```
<211> LENGTH: 20
<212> TYPE: PRT
<213> ORGANISM: Artificial Sequence
<220> FEATURE:
<223> OTHER INFORMATION: Synthetic

<400> SEQUENCE: 18

Pro Val Gln Gln Ile Gly Gly Asn Tyr Val His Leu Pro Leu Ser Pro
1               5                   10                  15

Arg Thr Leu Asn
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Tyr Val His Leu Pro Leu Ser Pro Arg Thr Leu Asn Ala Trp Val Lys
1               5                   10                  15

Leu Ile Glu Glu
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic

<400> SEQUENCE: 20

Arg Thr Leu Asn Ala Trp Val Lys Leu Ile Glu Glu Lys Lys Phe Gly
1               5                   10                  15

Ala Glu Val Val
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Leu Ile Glu Glu Lys Lys Phe Gly Ala Glu Val Val Pro Gly Phe Gln
1               5                   10                  15

Ala Leu Ser Glu
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic

<400> SEQUENCE: 22

Ala Glu Val Val Pro Gly Phe Gln Ala Leu Ser Glu Gly Cys Thr Pro
1               5                   10                  15

Tyr Asp Ile Asn
            20
```

```
<210> SEQ ID NO 23
<211> LENGTH: 20
<212> TYPE: PRT
<213> ORGANISM: Artificial Sequence
<220> FEATURE:
<223> OTHER INFORMATION: Synthetic

<400> SEQUENCE: 23

Ala Leu Ser Glu Gly Cys Thr Pro Tyr Asp Ile Asn Gln Met Leu Asn
1               5                   10                  15

Cys Val Gly Asp
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

Tyr Asp Ile Asn Gln Met Leu Asn Cys Val Gly Asp His Gln Ala Ala
1               5                   10                  15

Met Gln Ile Ile
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic

<400> SEQUENCE: 25

Cys Val Gly Asp His Gln Ala Ala Met Gln Ile Ile Arg Asp Ile Ile
1               5                   10                  15

Asn Glu Glu Ala
            20

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Met Gln Ile Ile Arg Asp Ile Ile Asn Glu Glu Ala Ala Asp Trp Asp
1               5                   10                  15

Leu Gln His

<210> SEQ ID NO 27
<211> LENGTH: 20
<212> TYPE: PRT
<213> ORGANISM: Artificial Sequence
<220> FEATURE:
<223> OTHER INFORMATION: Synthetic

<400> SEQUENCE: 27

Asn Glu Glu Ala Ala Asp Trp Asp Leu Gln His Pro Gln Pro Ala Pro
1               5                   10                  15

Gln Gln Gly Gln
            20
```

```
<210> SEQ ID NO 28
<211> LENGTH: 21
<212> TYPE: PRT
<213> ORGANISM: Artificial Sequence
<220> FEATURE:
<223> OTHER INFORMATION: Synthetic

<400> SEQUENCE: 28

Leu Gln His Pro Gln Pro Ala Pro Gln Gln Gly Gln Leu Arg Glu Pro
1               5                   10                  15

Ser Gly Ser Asp Ile
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic

<400> SEQUENCE: 29

Gly Gln Leu Arg Glu Pro Ser Gly Ser Asp Ile Ala Gly Thr Thr Ser
1               5                   10                  15

Ser Val Asp Glu
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic

<400> SEQUENCE: 30

Ser Asp Ile Ala Gly Thr Thr Ser Ser Val Asp Glu Gln Ile Gln Trp
1               5                   10                  15

Met Tyr Arg Gln
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic

<400> SEQUENCE: 31

Ser Val Asp Glu Gln Ile Gln Trp Met Tyr Arg Gln Gln Asn Pro Ile
1               5                   10                  15

Pro Val Gly Asn
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic

<400> SEQUENCE: 32

Met Tyr Arg Gln Gln Asn Pro Ile Pro Val Gly Asn Ile Tyr Arg Arg
1               5                   10                  15

Trp Ile Gln Leu
            20
```

<210> SEQ ID NO 33
<211> LENGTH: 20
<212> TYPE: PRT
<213> ORGANISM: Artificial Sequence
<220> FEATURE:
<223> OTHER INFORMATION: Synthetic

<400> SEQUENCE: 33

Pro Val Gly Asn Ile Tyr Arg Arg Trp Ile Gln Leu Gly Leu Gln Lys
1               5                   10                  15

Cys Val Arg Met
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic

<400> SEQUENCE: 34

Trp Ile Gln Leu Gly Leu Gln Lys Cys Val Arg Met Tyr Asn Pro Thr
1               5                   10                  15

Asn Ile Leu Asp
            20

<210> SEQ ID NO 35
<211> LENGTH: 19
<212> TYPE: PRT
<213> ORGANISM: Artificial Sequence
<220> FEATURE:
<223> OTHER INFORMATION: Synthetic

<400> SEQUENCE: 35

Cys Val Arg Met Tyr Asn Pro Thr Asn Ile Leu Asp Val Lys Gln Gly
1               5                   10                  15

Pro Lys Glu

<210> SEQ ID NO 36
<211> LENGTH: 20
<212> TYPE: PRT
<213> ORGANISM: Artificial Sequence
<220> FEATURE:
<223> OTHER INFORMATION: Synthetic

<400> SEQUENCE: 36

Thr Asn Ile Leu Asp Val Lys Gln Gly Pro Lys Glu Pro Phe Gln Ser
1               5                   10                  15

Tyr Val Asp Arg
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic

<400> SEQUENCE: 37

Gly Pro Lys Glu Pro Phe Gln Ser Tyr Val Asp Arg Phe Tyr Lys Ser
1               5                   10                  15

Leu Arg Ala Glu
            20

```
<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Tyr Val Asp Arg Phe Tyr Lys Ser Leu Arg Ala Glu Gln Thr Asp Ala
1               5                   10                  15

Ala Val Lys Asn
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic

<400> SEQUENCE: 39

Leu Arg Ala Glu Gln Thr Asp Ala Ala Val Lys Asn Trp Met Thr Gln
1               5                   10                  15

Thr Leu Leu Ile
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic

<400> SEQUENCE: 40

Ala Val Lys Asn Trp Met Thr Gln Thr Leu Leu Ile Gln Asn Ala Asn
1               5                   10                  15

Pro Asp Cys Lys
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic

<400> SEQUENCE: 41

Thr Leu Leu Ile Gln Asn Ala Asn Pro Asp Cys Lys Leu Val Leu Lys
1               5                   10                  15

Gly Leu Gly Val
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic

<400> SEQUENCE: 42

Pro Asp Cys Lys Leu Val Leu Lys Gly Leu Gly Val Asn Pro Thr Leu
1               5                   10                  15

Glu Glu Met Leu
            20
```

```
<210> SEQ ID NO 43
<211> LENGTH: 20
<212> TYPE: PRT
<213> ORGANISM: Artificial Sequence
<220> FEATURE:
<223> OTHER INFORMATION: Synthetic

<400> SEQUENCE: 43

Gly Leu Gly Val Asn Pro Thr Leu Glu Glu Met Leu Thr Ala Cys Gln
1               5                   10                  15

Gly Val Gly Gly
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic

<400> SEQUENCE: 44

Glu Glu Met Leu Thr Ala Cys Gln Gly Val Gly Gly Pro Gly Gln Lys
1               5                   10                  15

Ala Arg Leu Met
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic

<400> SEQUENCE: 45

Gly Val Gly Gly Pro Gly Gln Lys Ala Arg Leu Met Ala Glu Ala Leu
1               5                   10                  15

Lys Glu Ala Leu
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic

<400> SEQUENCE: 46

Ala Arg Leu Met Ala Glu Ala Leu Lys Glu Ala Leu Ala Pro Val Pro
1               5                   10                  15

Ile Pro Phe Ala
            20

<210> SEQ ID NO 47
<211> LENGTH: 21
<212> TYPE: PRT
<213> ORGANISM: Artificial Sequence
<220> FEATURE:
<223> OTHER INFORMATION: Synthetic

<400> SEQUENCE: 47

Lys Glu Ala Leu Ala Pro Val Pro Ile Pro Phe Ala Ala Ala Gln Gln
1               5                   10                  15

Arg Gly Pro Arg Lys
```

```
<210> SEQ ID NO 48
<211> LENGTH: 20
<212> TYPE: PRT
<213> ORGANISM: Artificial Sequence
<220> FEATURE:
<223> OTHER INFORMATION: Synthetic

<400> SEQUENCE: 48

Pro Phe Ala Ala Ala Gln Gln Arg Gly Pro Arg Lys Pro Ile Lys Cys
1               5                   10                  15

Trp Asn Cys Gly
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic

<400> SEQUENCE: 49

Gly Pro Arg Lys Pro Ile Lys Cys Trp Asn Cys Gly Lys Glu Gly His
1               5                   10                  15

Ser Ala Arg Gln
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic

<400> SEQUENCE: 50

Trp Asn Cys Gly Lys Glu Gly His Ser Ala Arg Gln Cys Arg Ala Pro
1               5                   10                  15

Arg Arg Gln Gly
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic

<400> SEQUENCE: 51

Ser Ala Arg Gln Cys Arg Ala Pro Arg Arg Gln Gly Cys Trp Lys Cys
1               5                   10                  15

Gly Lys Met Asp
            20

<210> SEQ ID NO 52
<211> LENGTH: 21
<212> TYPE: PRT
<213> ORGANISM: Artificial Sequence
<220> FEATURE:
<223> OTHER INFORMATION: Synthetic

<400> SEQUENCE: 52

Arg Arg Gln Gly Cys Trp Lys Cys Gly Lys Met Asp His Val Met Ala
1               5                   10                  15
```

```
Lys Cys Pro Thr Ala
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Lys Met Asp His Val Met Ala Lys Cys Pro Asp Arg Gln Ala Gly Phe
1               5                   10                  15

Leu Gly Leu Gly
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic

<400> SEQUENCE: 54

Cys Pro Asp Arg Gln Ala Gly Phe Leu Gly Leu Gly Pro Trp Gly Lys
1               5                   10                  15

Lys Pro Arg Asn
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic

<400> SEQUENCE: 55

Leu Gly Leu Gly Pro Trp Gly Lys Lys Pro Arg Asn Phe Pro Met Ala
1               5                   10                  15

Gln Val His Gln
            20

<210> SEQ ID NO 56
<211> LENGTH: 18
<212> TYPE: PRT
<213> ORGANISM: Artificial Sequence
<220> FEATURE:
<223> OTHER INFORMATION: Synthetic

<400> SEQUENCE: 56

Lys Pro Arg Asn Phe Pro Met Ala Gln Val His Gln Gly Leu Met Pro
1               5                   10                  15

Thr Ala

<210> SEQ ID NO 57
<211> LENGTH: 20
<212> TYPE: PRT
<213> ORGANISM: Artificial Sequence
<220> FEATURE:
<223> OTHER INFORMATION: Synthetic

<400> SEQUENCE: 57

Met Ala Gln Val His Gln Gly Leu Met Pro Thr Ala Pro Pro Glu Asp
1               5                   10                  15
```

-continued

```
Pro Ala Val Asp
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic

<400> SEQUENCE: 58

Met Pro Thr Ala Pro Pro Glu Asp Pro Ala Val Asp Leu Leu Lys Asn
1               5                   10                  15

Tyr Met Gln Leu
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic

<400> SEQUENCE: 59

Pro Ala Val Asp Leu Leu Lys Asn Tyr Met Gln Leu Gly Lys Gln Gln
1               5                   10                  15

Arg Glu Lys Gln
            20

<210> SEQ ID NO 60
<211> LENGTH: 21
<212> TYPE: PRT
<213> ORGANISM: Artificial Sequence
<220> FEATURE:
<223> OTHER INFORMATION: Synthetic

<400> SEQUENCE: 60

Tyr Met Gln Leu Gly Lys Gln Gln Arg Glu Lys Gln Arg Glu Ser Arg
1               5                   10                  15

Glu Lys Pro Tyr Lys
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic

<400> SEQUENCE: 61

Glu Lys Gln Arg Glu Ser Arg Glu Lys Pro Tyr Lys Glu Val Thr Glu
1               5                   10                  15

Asp Leu Leu His
            20

<210> SEQ ID NO 62
<211> LENGTH: 21
<212> TYPE: PRT
<213> ORGANISM: Artificial Sequence
<220> FEATURE:
<223> OTHER INFORMATION: Synthetic

<400> SEQUENCE: 62

Lys Pro Tyr Lys Glu Val Thr Glu Asp Leu Leu His Leu Asn Ser Leu
1               5                   10                  15
```

Phe Gly Gly Asp Gln
        20

<210> SEQ ID NO 63
<211> LENGTH: 510
<212> TYPE: PRT
<213> ORGANISM: Simian Immunodeficiency Virus

<400> SEQUENCE: 63

Met Gly Val Arg Asn Ser Val Leu Ser Gly Lys Lys Ala Asp Glu Leu
1               5                   10                  15

Glu Lys Ile Arg Leu Arg Pro Asn Gly Lys Lys Lys Tyr Met Leu Lys
            20                  25                  30

His Val Val Trp Ala Ala Asn Glu Leu Asp Arg Phe Gly Leu Ala Glu
        35                  40                  45

Ser Leu Leu Glu Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Thr Glu Thr Met Pro Lys Thr Ser Arg Pro Thr Ala Pro Ser
        115                 120                 125

Ser Gly Arg Gly Gly Asn Tyr Pro Val Gln Gln Ile Gly Gly Asn Tyr
    130                 135                 140

Val His Leu Pro Leu Ser Pro Arg Thr Leu Asn Ala Trp Val Lys Leu
145                 150                 155                 160

Ile Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
            180                 185                 190

Val Gly Asp His Gln Ala Ala Met Gln Ile Ile Arg Asp Ile Ile Asn
        195                 200                 205

Glu Glu Ala Ala Asp Trp Asp Leu Gln His Pro Gln Pro Ala Pro Gln
    210                 215                 220

Gln Gly Gln Leu Arg Glu Pro Ser Gly Ser Asp Ile Ala Gly Thr Thr
225                 230                 235                 240

Ser Ser Val Asp Glu Gln Ile Gln Trp Met Tyr Arg Gln Gln Asn Pro
                245                 250                 255

Ile Pro Val Gly Asn Ile Tyr Arg Arg Trp Ile Gln Leu Gly Leu Gln
            260                 265                 270

Lys Cys Val Arg Met Tyr Asn Pro Thr Asn Ile Leu Asp Val Lys Gln
        275                 280                 285

Gly Pro Lys Glu Pro Phe Gln Ser Tyr Val Asp Arg Phe Tyr Lys Ser
    290                 295                 300

Leu Arg Ala Glu Gln Thr Asp Ala Ala Val Lys Asn Trp Met Thr Gln
305                 310                 315                 320

Thr Leu Leu Ile Gln Asn Ala Asn Pro Asp Cys Lys Leu Val Leu Lys
                325                 330                 335

Gly Leu Gly Val Asn Pro Thr Leu Glu Glu Met Leu Thr Ala Cys Gln
            340                 345                 350

Gly Val Gly Gly Pro Gly Gln Lys Ala Arg Leu Met Ala Glu Ala Leu

```
                355                 360                 365
Lys Glu Ala Leu Ala Pro Val Pro Ile Pro Phe Ala Ala Ala Gln Gln
            370                 375                 380
Arg Gly Pro Arg Lys Pro Ile Lys Cys Trp Asn Cys Gly Lys Glu Gly
385                 390                 395                 400
His Ser Ala Arg Gln Cys Arg Ala Pro Arg Arg Gln Gly Cys Trp Lys
                405                 410                 415
Cys Gly Lys Met Asp His Val Met Ala Lys Cys Pro Asp Arg Gln Ala
            420                 425                 430
Gly Phe Leu Gly Leu Gly Pro Trp Gly Lys Lys Pro Arg Asn Phe Pro
            435                 440                 445
Met Ala Gln Val His Gln Gly Leu Met Pro Thr Ala Pro Pro Glu Asp
            450                 455                 460
Pro Ala Val Asp Leu Leu Lys Asn Tyr Met Gln Leu Gly Lys Gln Gln
465                 470                 475                 480
Arg Glu Lys Gln Arg Glu Ser Arg Glu Lys Pro Tyr Lys Glu Val Thr
                485                 490                 495
Glu Asp Leu Leu His Leu Asn Ser Leu Phe Gly Gly Asp Gln
            500                 505                 510

<210> SEQ ID NO 64
<211> LENGTH: 25
<212> TYPE: PRT
<213> ORGANISM: Artificial Sequence
<220> FEATURE:
<223> OTHER INFORMATION: Synthetic

<400> SEQUENCE: 64

Met Gly Cys Leu Gly Asn Gln Leu Leu Ile Ala Ile Leu Leu Leu Ser
1               5                   10                  15
Val Tyr Gly Ile Tyr Cys Thr Leu Tyr
            20                  25

<210> SEQ ID NO 65
<211> LENGTH: 25
<212> TYPE: PRT
<213> ORGANISM: Artificial Sequence
<220> FEATURE:
<223> OTHER INFORMATION: Synthetic

<400> SEQUENCE: 65

Leu Leu Leu Ser Val Tyr Gly Ile Tyr Cys Thr Leu Tyr Val Thr Val
1               5                   10                  15
Phe Tyr Gly Val Pro Ala Trp Arg Asn
            20                  25

<210> SEQ ID NO 66
<211> LENGTH: 25
<212> TYPE: PRT
<213> ORGANISM: Artificial Sequence
<220> FEATURE:
<223> OTHER INFORMATION: Synthetic

<400> SEQUENCE: 66

Tyr Val Thr Val Phe Tyr Gly Val Pro Ala Trp Arg Asn Ala Thr Ile
1               5                   10                  15
Pro Leu Phe Cys Ala Thr Lys Asn Arg
            20                  25

<210> SEQ ID NO 67
```

```
<211> LENGTH: 25
<212> TYPE: PRT
<213> ORGANISM: Artificial Sequence
<220> FEATURE:
<223> OTHER INFORMATION: Synthetic

<400> SEQUENCE: 67

Asn Ala Thr Ile Pro Leu Phe Cys Ala Thr Lys Asn Arg Asp Thr Trp
1               5                   10                  15

Gly Thr Thr Gln Cys Leu Pro Asp Asn
            20                  25

<210> SEQ ID NO 68
<211> LENGTH: 25
<212> TYPE: PRT
<213> ORGANISM: Artificial Sequence
<220> FEATURE:
<223> OTHER INFORMATION: Synthetic

<400> SEQUENCE: 68

Arg Asp Thr Trp Gly Thr Thr Gln Cys Leu Pro Asp Asn Gly Asp Tyr
1               5                   10                  15

Ser Glu Val Ala Leu Asn Val Thr Glu
            20                  25

<210> SEQ ID NO 69
<211> LENGTH: 25
<212> TYPE: PRT
<213> ORGANISM: Artificial Sequence
<220> FEATURE:
<223> OTHER INFORMATION: Synthetic

<400> SEQUENCE: 69

Asn Gly Asp Tyr Ser Glu Val Ala Leu Asn Val Thr Glu Ser Phe Asp
1               5                   10                  15

Ala Trp Asn Asn Thr Val Thr Glu Gln
            20                  25

<210> SEQ ID NO 70
<211> LENGTH: 25
<212> TYPE: PRT
<213> ORGANISM: Artificial Sequence
<220> FEATURE:
<223> OTHER INFORMATION: Synthetic

<400> SEQUENCE: 70

Glu Ser Phe Asp Ala Trp Asn Asn Thr Val Thr Glu Gln Ala Ile Glu
1               5                   10                  15

Asp Val Trp Gln Leu Phe Glu Thr Ser
            20                  25

<210> SEQ ID NO 71
<211> LENGTH: 25
<212> TYPE: PRT
<213> ORGANISM: Artificial Sequence
<220> FEATURE:
<223> OTHER INFORMATION: Synthetic

<400> SEQUENCE: 71

Gln Ala Ile Glu Asp Val Trp Gln Leu Phe Glu Thr Ser Ile Lys Pro
1               5                   10                  15

Cys Val Lys Leu Ser Pro Leu Cys Ile
            20                  25
```

```
<210> SEQ ID NO 72
<211> LENGTH: 25
<212> TYPE: PRT
<213> ORGANISM: Artificial Sequence
<220> FEATURE:
<223> OTHER INFORMATION: Synthetic

<400> SEQUENCE: 72

Ser Ile Lys Pro Cys Val Lys Leu Ser Pro Leu Cys Ile Thr Met Arg
1               5                   10                  15

Cys Asn Lys Ser Glu Thr Asp Arg Trp
            20                  25

<210> SEQ ID NO 73
<211> LENGTH: 24
<212> TYPE: PRT
<213> ORGANISM: Artificial Sequence
<220> FEATURE:
<223> OTHER INFORMATION: Synthetic

<400> SEQUENCE: 73

Thr Met Arg Cys Asn Lys Ser Glu Thr Asp Arg Trp Gly Leu Thr Lys
1               5                   10                  15

Ser Ile Thr Thr Thr Ala Ser Thr
            20

<210> SEQ ID NO 74
<211> LENGTH: 25
<212> TYPE: PRT
<213> ORGANISM: Artificial Sequence
<220> FEATURE:
<223> OTHER INFORMATION: Synthetic

<400> SEQUENCE: 74

Trp Gly Leu Thr Lys Ser Ile Thr Thr Ala Ser Thr Thr Ser Thr
1               5                   10                  15

Thr Ala Ser Ala Lys Val Asp Met Val
            20                  25

<210> SEQ ID NO 75
<211> LENGTH: 25
<212> TYPE: PRT
<213> ORGANISM: Artificial Sequence
<220> FEATURE:
<223> OTHER INFORMATION: Synthetic

<400> SEQUENCE: 75

Thr Thr Ser Thr Thr Ala Ser Ala Lys Val Asp Met Val Asn Glu Thr
1               5                   10                  15

Ser Ser Cys Ile Ala Gln Asp Asn Cys
            20                  25

<210> SEQ ID NO 76
<211> LENGTH: 25
<212> TYPE: PRT
<213> ORGANISM: Artificial Sequence
<220> FEATURE:
<223> OTHER INFORMATION: Synthetic

<400> SEQUENCE: 76

Val Asn Glu Thr Ser Ser Cys Ile Ala Gln Asp Asn Cys Thr Gly Leu
1               5                   10                  15

Glu Gln Glu Gln Met Ile Ser Cys Lys
            20                  25
```

```
<210> SEQ ID NO 77
<211> LENGTH: 25
<212> TYPE: PRT
<213> ORGANISM: Artificial Sequence
<220> FEATURE:
<223> OTHER INFORMATION: Synthetic

<400> SEQUENCE: 77

Cys Thr Gly Leu Glu Gln Glu Gln Met Ile Ser Cys Lys Phe Asn Met
1               5                   10                  15

Thr Gly Leu Lys Arg Asp Lys Lys Lys
            20                  25

<210> SEQ ID NO 78
<211> LENGTH: 25
<212> TYPE: PRT
<213> ORGANISM: Artificial Sequence
<220> FEATURE:
<223> OTHER INFORMATION: Synthetic

<400> SEQUENCE: 78

Lys Phe Asn Met Thr Gly Leu Lys Arg Asp Lys Lys Lys Glu Tyr Asn
1               5                   10                  15

Glu Thr Trp Tyr Ser Ala Asp Leu Val
            20                  25

<210> SEQ ID NO 79
<211> LENGTH: 25
<212> TYPE: PRT
<213> ORGANISM: Artificial Sequence
<220> FEATURE:
<223> OTHER INFORMATION: Synthetic

<400> SEQUENCE: 79

Lys Glu Tyr Asn Glu Thr Trp Tyr Ser Ala Asp Leu Val Cys Glu Gln
1               5                   10                  15

Gly Asn Asn Thr Gly Asn Glu Ser Arg
            20                  25

<210> SEQ ID NO 80
<211> LENGTH: 25
<212> TYPE: PRT
<213> ORGANISM: Artificial Sequence
<220> FEATURE:
<223> OTHER INFORMATION: Synthetic

<400> SEQUENCE: 80

Val Cys Glu Gln Gly Asn Asn Thr Gly Asn Glu Ser Arg Cys Tyr Met
1               5                   10                  15

Asn His Cys Asn Thr Ser Val Ile Gln
            20                  25

<210> SEQ ID NO 81
<211> LENGTH: 25
<212> TYPE: PRT
<213> ORGANISM: Artificial Sequence
<220> FEATURE:
<223> OTHER INFORMATION: Synthetic

<400> SEQUENCE: 81

Arg Cys Tyr Met Asn His Cys Asn Thr Ser Val Ile Gln Glu Ser Cys
1               5                   10                  15

Asp Lys His Tyr Trp Asp Ala Ile Arg
            20                  25
```

<210> SEQ ID NO 82
<211> LENGTH: 25
<212> TYPE: PRT
<213> ORGANISM: Artificial Sequence
<220> FEATURE:
<223> OTHER INFORMATION: Synthetic

<400> SEQUENCE: 82

Gln Glu Ser Cys Asp Lys His Tyr Trp Asp Ala Ile Arg Phe Arg Tyr
1               5                   10                  15

Cys Ala Pro Pro Gly Tyr Ala Leu Leu
            20                  25

<210> SEQ ID NO 83
<211> LENGTH: 25
<212> TYPE: PRT
<213> ORGANISM: Artificial Sequence
<220> FEATURE:
<223> OTHER INFORMATION: Synthetic

<400> SEQUENCE: 83

Arg Phe Arg Tyr Cys Ala Pro Pro Gly Tyr Ala Leu Leu Arg Cys Asn
1               5                   10                  15

Asp Thr Asn Tyr Ser Gly Phe Met Pro
            20                  25

<210> SEQ ID NO 84
<211> LENGTH: 25
<212> TYPE: PRT
<213> ORGANISM: Artificial Sequence
<220> FEATURE:
<223> OTHER INFORMATION: Synthetic

<400> SEQUENCE: 84

Leu Arg Cys Asn Asp Thr Asn Tyr Ser Gly Phe Met Pro Lys Cys Ser
1               5                   10                  15

Lys Val Val Val Ser Ser Cys Thr Arg
            20                  25

<210> SEQ ID NO 85
<211> LENGTH: 25
<212> TYPE: PRT
<213> ORGANISM: Artificial Sequence
<220> FEATURE:
<223> OTHER INFORMATION: Synthetic

<400> SEQUENCE: 85

Pro Lys Cys Ser Lys Val Val Val Ser Ser Cys Thr Arg Met Met Glu
1               5                   10                  15

Thr Gln Thr Ser Thr Trp Phe Gly Phe
            20                  25

<210> SEQ ID NO 86
<211> LENGTH: 25
<212> TYPE: PRT
<213> ORGANISM: Artificial Sequence
<220> FEATURE:
<223> OTHER INFORMATION: Synthetic

<400> SEQUENCE: 86

Arg Met Met Glu Thr Gln Thr Ser Thr Trp Phe Gly Phe Asn Gly Thr
1               5                   10                  15

Arg Ala Glu Asn Arg Thr Tyr Ile Tyr

-continued

```
                20                  25

<210> SEQ ID NO 87
<211> LENGTH: 25
<212> TYPE: PRT
<213> ORGANISM: Artificial Sequence
<220> FEATURE:
<223> OTHER INFORMATION: Synthetic

<400> SEQUENCE: 87

Phe Asn Gly Thr Arg Ala Glu Asn Arg Thr Tyr Ile Tyr Trp His Gly
1               5                   10                  15

Arg Asp Asn Arg Thr Ile Ile Ser Leu
            20                  25

<210> SEQ ID NO 88
<211> LENGTH: 25
<212> TYPE: PRT
<213> ORGANISM: Artificial Sequence
<220> FEATURE:
<223> OTHER INFORMATION: Synthetic

<400> SEQUENCE: 88

Tyr Trp His Gly Arg Asp Asn Arg Thr Ile Ile Ser Leu Asn Lys Tyr
1               5                   10                  15

Tyr Asn Leu Thr Met Lys Cys Arg Arg
            20                  25

<210> SEQ ID NO 89
<211> LENGTH: 25
<212> TYPE: PRT
<213> ORGANISM: Artificial Sequence
<220> FEATURE:
<223> OTHER INFORMATION: Synthetic

<400> SEQUENCE: 89

Leu Asn Lys Tyr Tyr Asn Leu Thr Met Lys Cys Arg Arg Pro Gly Asn
1               5                   10                  15

Lys Thr Val Leu Pro Val Thr Ile Met
            20                  25

<210> SEQ ID NO 90
<211> LENGTH: 25
<212> TYPE: PRT
<213> ORGANISM: Artificial Sequence
<220> FEATURE:
<223> OTHER INFORMATION: Synthetic

<400> SEQUENCE: 90

Arg Pro Gly Asn Lys Thr Val Leu Pro Val Thr Ile Met Ser Gly Leu
1               5                   10                  15

Val Phe His Ser Gln Pro Ile Asn Asp
            20                  25

<210> SEQ ID NO 91
<211> LENGTH: 25
<212> TYPE: PRT
<213> ORGANISM: Artificial Sequence
<220> FEATURE:
<223> OTHER INFORMATION: Synthetic

<400> SEQUENCE: 91

Met Ser Gly Leu Val Phe His Ser Gln Pro Ile Asn Asp Arg Pro Lys
1               5                   10                  15
```

```
Gln Ala Trp Cys Trp Phe Gly Gly Lys
            20                  25

<210> SEQ ID NO 92
<211> LENGTH: 25
<212> TYPE: PRT
<213> ORGANISM: Artificial Sequence
<220> FEATURE:
<223> OTHER INFORMATION: Synthetic

<400> SEQUENCE: 92

Asp Arg Pro Lys Gln Ala Trp Cys Trp Phe Gly Gly Lys Trp Lys Asp
1               5                   10                  15

Ala Ile Lys Glu Val Lys Gln Thr Ile
            20                  25

<210> SEQ ID NO 93
<211> LENGTH: 25
<212> TYPE: PRT
<213> ORGANISM: Artificial Sequence
<220> FEATURE:
<223> OTHER INFORMATION: Synthetic

<400> SEQUENCE: 93

Lys Trp Lys Asp Ala Ile Lys Glu Val Lys Gln Thr Ile Val Lys His
1               5                   10                  15

Pro Arg Tyr Thr Gly Thr Asn Asn Thr
            20                  25

<210> SEQ ID NO 94
<211> LENGTH: 25
<212> TYPE: PRT
<213> ORGANISM: Artificial Sequence
<220> FEATURE:
<223> OTHER INFORMATION: Synthetic

<400> SEQUENCE: 94

Ile Val Lys His Pro Arg Tyr Thr Gly Thr Asn Asn Thr Asp Lys Ile
1               5                   10                  15

Asn Leu Thr Ala Pro Gly Gly Gly Asp
            20                  25

<210> SEQ ID NO 95
<211> LENGTH: 25
<212> TYPE: PRT
<213> ORGANISM: Artificial Sequence
<220> FEATURE:
<223> OTHER INFORMATION: Synthetic

<400> SEQUENCE: 95

Thr Asp Lys Ile Asn Leu Thr Ala Pro Gly Gly Gly Asp Pro Glu Val
1               5                   10                  15

Thr Phe Met Trp Thr Asn Cys Arg Gly
            20                  25

<210> SEQ ID NO 96
<211> LENGTH: 25
<212> TYPE: PRT
<213> ORGANISM: Artificial Sequence
<220> FEATURE:
<223> OTHER INFORMATION: Synthetic

<400> SEQUENCE: 96

Asp Pro Glu Val Thr Phe Met Trp Thr Asn Cys Arg Gly Glu Phe Leu
1               5                   10                  15
```

-continued

```
Tyr Cys Lys Met Asn Trp Phe Leu Asn
            20                  25

<210> SEQ ID NO 97
<211> LENGTH: 25
<212> TYPE: PRT
<213> ORGANISM: Artificial Sequence
<220> FEATURE:
<223> OTHER INFORMATION: Synthetic

<400> SEQUENCE: 97

Gly Glu Phe Leu Tyr Cys Lys Met Asn Trp Phe Leu Asn Trp Val Glu
1               5                   10                  15

Asp Arg Asn Thr Ala Asn Gln Lys Pro
            20                  25

<210> SEQ ID NO 98
<211> LENGTH: 25
<212> TYPE: PRT
<213> ORGANISM: Artificial Sequence
<220> FEATURE:
<223> OTHER INFORMATION: Synthetic

<400> SEQUENCE: 98

Asn Trp Val Glu Asp Arg Asn Thr Ala Asn Gln Lys Pro Lys Glu Gln
1               5                   10                  15

His Lys Arg Asn Tyr Val Pro Cys His
            20                  25

<210> SEQ ID NO 99
<211> LENGTH: 25
<212> TYPE: PRT
<213> ORGANISM: Artificial Sequence
<220> FEATURE:
<223> OTHER INFORMATION: Synthetic

<400> SEQUENCE: 99

Pro Lys Glu Gln His Lys Arg Asn Tyr Val Pro Cys His Ile Arg Gln
1               5                   10                  15

Ile Ile Asn Thr Trp His Lys Val Gly
            20                  25

<210> SEQ ID NO 100
<211> LENGTH: 25
<212> TYPE: PRT
<213> ORGANISM: Artificial Sequence
<220> FEATURE:
<223> OTHER INFORMATION: Synthetic

<400> SEQUENCE: 100

His Ile Arg Gln Ile Ile Asn Thr Trp His Lys Val Gly Lys Asn Val
1               5                   10                  15

Tyr Leu Pro Pro Arg Glu Gly Asp Leu
            20                  25

<210> SEQ ID NO 101
<211> LENGTH: 25
<212> TYPE: PRT
<213> ORGANISM: Artificial Sequence
<220> FEATURE:
<223> OTHER INFORMATION: Synthetic

<400> SEQUENCE: 101

Gly Lys Asn Val Tyr Leu Pro Pro Arg Glu Gly Asp Leu Thr Cys Asn
```

```
                   1               5                  10                  15
Ser Thr Val Thr Ser Leu Ile Ala Asn
                  20                  25

<210> SEQ ID NO 102
<211> LENGTH: 25
<212> TYPE: PRT
<213> ORGANISM: Artificial Sequence
<220> FEATURE:
<223> OTHER INFORMATION: Synthetic

<400> SEQUENCE: 102

Leu Thr Cys Asn Ser Thr Val Thr Ser Leu Ile Ala Asn Ile Asp Trp
1               5                  10                  15

Ile Asp Gly Asn Gln Thr Asn Ile Thr
                  20                  25

<210> SEQ ID NO 103
<211> LENGTH: 25
<212> TYPE: PRT
<213> ORGANISM: Artificial Sequence
<220> FEATURE:
<223> OTHER INFORMATION: Synthetic

<400> SEQUENCE: 103

Asn Ile Asp Trp Ile Asp Gly Asn Gln Thr Asn Ile Thr Met Ser Ala
1               5                  10                  15

Glu Val Ala Glu Leu Tyr Arg Leu Glu
                  20                  25

<210> SEQ ID NO 104
<211> LENGTH: 25
<212> TYPE: PRT
<213> ORGANISM: Artificial Sequence
<220> FEATURE:
<223> OTHER INFORMATION: Synthetic

<400> SEQUENCE: 104

Thr Met Ser Ala Glu Val Ala Glu Leu Tyr Arg Leu Glu Leu Gly Asp
1               5                  10                  15

Tyr Lys Leu Val Glu Ile Thr Pro Ile
                  20                  25

<210> SEQ ID NO 105
<211> LENGTH: 25
<212> TYPE: PRT
<213> ORGANISM: Artificial Sequence
<220> FEATURE:
<223> OTHER INFORMATION: Synthetic

<400> SEQUENCE: 105

Glu Leu Gly Asp Tyr Lys Leu Val Glu Ile Thr Pro Ile Gly Leu Ala
1               5                  10                  15

Pro Thr Asp Val Lys Arg Tyr Thr Thr
                  20                  25

<210> SEQ ID NO 106
<211> LENGTH: 25
<212> TYPE: PRT
<213> ORGANISM: Artificial Sequence
<220> FEATURE:
<223> OTHER INFORMATION: Synthetic

<400> SEQUENCE: 106
```

-continued

Ile Gly Leu Ala Pro Thr Asp Val Lys Arg Tyr Thr Thr Gly Gly Thr
1               5                   10                  15

Ser Arg Asn Lys Arg Gly Val Phe Val
            20                  25

<210> SEQ ID NO 107
<211> LENGTH: 25
<212> TYPE: PRT
<213> ORGANISM: Artificial Sequence
<220> FEATURE:
<223> OTHER INFORMATION: Synthetic

<400> SEQUENCE: 107

Thr Gly Gly Thr Ser Arg Asn Lys Arg Gly Val Phe Val Leu Gly Phe
1               5                   10                  15

Leu Gly Phe Leu Ala Thr Ala Gly Ser
            20                  25

<210> SEQ ID NO 108
<211> LENGTH: 25
<212> TYPE: PRT
<213> ORGANISM: Artificial Sequence
<220> FEATURE:
<223> OTHER INFORMATION: Synthetic

<400> SEQUENCE: 108

Val Leu Gly Phe Leu Gly Phe Leu Ala Thr Ala Gly Ser Ala Met Gly
1               5                   10                  15

Ala Ala Ser Leu Thr Leu Thr Ala Gln
            20                  25

<210> SEQ ID NO 109
<211> LENGTH: 25
<212> TYPE: PRT
<213> ORGANISM: Artificial Sequence
<220> FEATURE:
<223> OTHER INFORMATION: Synthetic

<400> SEQUENCE: 109

Ser Ala Met Gly Ala Ala Ser Leu Thr Leu Thr Ala Gln Ser Arg Thr
1               5                   10                  15

Leu Leu Ala Gly Ile Val Gln Gln Gln
            20                  25

<210> SEQ ID NO 110
<211> LENGTH: 25
<212> TYPE: PRT
<213> ORGANISM: Artificial Sequence
<220> FEATURE:
<223> OTHER INFORMATION: Synthetic

<400> SEQUENCE: 110

Gln Ser Arg Thr Leu Leu Ala Gly Ile Val Gln Gln Gln Gln Gln Leu
1               5                   10                  15

Leu Asp Val Val Lys Arg Gln Gln Glu
            20                  25

<210> SEQ ID NO 111
<211> LENGTH: 25
<212> TYPE: PRT
<213> ORGANISM: Artificial Sequence
<220> FEATURE:
<223> OTHER INFORMATION: Synthetic

<400> SEQUENCE: 111

Gln Gln Gln Leu Leu Asp Val Val Lys Arg Gln Gln Glu Leu Leu Arg
1               5                   10                  15

Leu Thr Val Trp Gly Thr Lys Asn Leu
            20                  25

<210> SEQ ID NO 112
<211> LENGTH: 25
<212> TYPE: PRT
<213> ORGANISM: Artificial Sequence
<220> FEATURE:
<223> OTHER INFORMATION: Synthetic

<400> SEQUENCE: 112

Glu Leu Leu Arg Leu Thr Val Trp Gly Thr Lys Asn Leu Gln Thr Arg
1               5                   10                  15

Val Thr Ala Ile Glu Lys Tyr Leu Lys
            20                  25

<210> SEQ ID NO 113
<211> LENGTH: 25
<212> TYPE: PRT
<213> ORGANISM: Artificial Sequence
<220> FEATURE:
<223> OTHER INFORMATION: Synthetic

<400> SEQUENCE: 113

Leu Gln Thr Arg Val Thr Ala Ile Glu Lys Tyr Leu Lys Asp Gln Ala
1               5                   10                  15

Gln Leu Asn Ala Trp Gly Cys Ala Phe
            20                  25

<210> SEQ ID NO 114
<211> LENGTH: 25
<212> TYPE: PRT
<213> ORGANISM: Artificial Sequence
<220> FEATURE:
<223> OTHER INFORMATION: Synthetic

<400> SEQUENCE: 114

Lys Asp Gln Ala Gln Leu Asn Ala Trp Gly Cys Ala Phe Arg Gln Val
1               5                   10                  15

Cys His Thr Thr Val Pro Trp Pro Asn
            20                  25

<210> SEQ ID NO 115
<211> LENGTH: 25
<212> TYPE: PRT
<213> ORGANISM: Artificial Sequence
<220> FEATURE:
<223> OTHER INFORMATION: Synthetic

<400> SEQUENCE: 115

Phe Arg Gln Val Cys His Thr Thr Val Pro Trp Pro Asn Ala Ser Leu
1               5                   10                  15

Thr Pro Lys Trp Asn Asn Glu Thr Trp
            20                  25

<210> SEQ ID NO 116
<211> LENGTH: 25
<212> TYPE: PRT
<213> ORGANISM: Artificial Sequence
<220> FEATURE:
<223> OTHER INFORMATION: Synthetic -continued

```
<400> SEQUENCE: 116

Asn Ala Ser Leu Thr Pro Lys Trp Asn Asn Glu Thr Trp Gln Glu Trp
1               5                   10                  15

Glu Arg Lys Val Asp Phe Leu Glu Glu
            20                  25

<210> SEQ ID NO 117
<211> LENGTH: 25
<212> TYPE: PRT
<213> ORGANISM: Artificial Sequence
<220> FEATURE:
<223> OTHER INFORMATION: Synthetic

<400> SEQUENCE: 117

Trp Gln Glu Trp Glu Arg Lys Val Asp Phe Leu Glu Glu Asn Ile Thr
1               5                   10                  15

Ala Leu Leu Glu Glu Ala Gln Ile Gln
            20                  25

<210> SEQ ID NO 118
<211> LENGTH: 25
<212> TYPE: PRT
<213> ORGANISM: Artificial Sequence
<220> FEATURE:
<223> OTHER INFORMATION: Synthetic

<400> SEQUENCE: 118

Glu Asn Ile Thr Ala Leu Leu Glu Glu Ala Gln Ile Gln Gln Glu Lys
1               5                   10                  15

Asn Met Tyr Glu Leu Gln Lys Leu Asn
            20                  25

<210> SEQ ID NO 119
<211> LENGTH: 25
<212> TYPE: PRT
<213> ORGANISM: Artificial Sequence
<220> FEATURE:
<223> OTHER INFORMATION: Synthetic

<400> SEQUENCE: 119

Gln Gln Glu Lys Asn Met Tyr Glu Leu Gln Lys Leu Asn Ser Trp Asp
1               5                   10                  15

Val Phe Gly Asn Trp Phe Asp Leu Ala
            20                  25

<210> SEQ ID NO 120
<211> LENGTH: 25
<212> TYPE: PRT
<213> ORGANISM: Artificial Sequence
<220> FEATURE:
<223> OTHER INFORMATION: Synthetic

<400> SEQUENCE: 120

Asn Ser Trp Asp Val Phe Gly Asn Trp Phe Asp Leu Ala Ser Trp Ile
1               5                   10                  15

Lys Tyr Ile Gln Tyr Gly Val Tyr Ile
            20                  25

<210> SEQ ID NO 121
<211> LENGTH: 25
<212> TYPE: PRT
<213> ORGANISM: Artificial Sequence
<220> FEATURE:
<223> OTHER INFORMATION: Synthetic
```

```
<400> SEQUENCE: 121

Ala Ser Trp Ile Lys Tyr Ile Gln Tyr Gly Val Tyr Ile Val Val Gly
1               5                   10                  15

Val Ile Leu Leu Arg Ile Val Ile Tyr
            20                  25

<210> SEQ ID NO 122
<211> LENGTH: 25
<212> TYPE: PRT
<213> ORGANISM: Artificial Sequence
<220> FEATURE:
<223> OTHER INFORMATION: Synthetic

<400> SEQUENCE: 122

Ile Val Val Gly Val Ile Leu Leu Arg Ile Val Ile Tyr Ile Val Gln
1               5                   10                  15

Met Leu Ala Lys Leu Arg Gln Gly Tyr
            20                  25

<210> SEQ ID NO 123
<211> LENGTH: 25
<212> TYPE: PRT
<213> ORGANISM: Artificial Sequence
<220> FEATURE:
<223> OTHER INFORMATION: Synthetic

<400> SEQUENCE: 123

Tyr Ile Val Gln Met Leu Ala Lys Leu Arg Gln Gly Tyr Arg Pro Val
1               5                   10                  15

Phe Ser Ser Pro Pro Ser Tyr Phe Gln
            20                  25

<210> SEQ ID NO 124
<211> LENGTH: 25
<212> TYPE: PRT
<213> ORGANISM: Artificial Sequence
<220> FEATURE:
<223> OTHER INFORMATION: Synthetic

<400> SEQUENCE: 124

Tyr Arg Pro Val Phe Ser Ser Pro Pro Ser Tyr Phe Gln Gln Thr His
1               5                   10                  15

Ile Gln Gln Asp Pro Ala Leu Pro Thr
            20                  25

<210> SEQ ID NO 125
<211> LENGTH: 25
<212> TYPE: PRT
<213> ORGANISM: Artificial Sequence
<220> FEATURE:
<223> OTHER INFORMATION: Synthetic

<400> SEQUENCE: 125

Gln Gln Thr His Ile Gln Gln Asp Pro Ala Leu Pro Thr Arg Glu Gly
1               5                   10                  15

Lys Glu Arg Asp Gly Gly Glu Gly Gly
            20                  25

<210> SEQ ID NO 126
<211> LENGTH: 25
<212> TYPE: PRT
<213> ORGANISM: Artificial Sequence
<220> FEATURE:
```

<223> OTHER INFORMATION: Synthetic

<400> SEQUENCE: 126

Thr Arg Glu Gly Lys Glu Arg Asp Gly Gly Glu Gly Gly Gly Asn Ser
1               5                   10                  15

Ser Trp Pro Trp Gln Ile Glu Tyr Ile
            20                  25

<210> SEQ ID NO 127
<211> LENGTH: 25
<212> TYPE: PRT
<213> ORGANISM: Artificial Sequence
<220> FEATURE:
<223> OTHER INFORMATION: Synthetic

<400> SEQUENCE: 127

Gly Gly Asn Ser Ser Trp Pro Trp Gln Ile Glu Tyr Ile His Phe Leu
1               5                   10                  15

Ile Arg Gln Leu Ile Arg Leu Leu Thr
            20                  25

<210> SEQ ID NO 128
<211> LENGTH: 25
<212> TYPE: PRT
<213> ORGANISM: Artificial Sequence
<220> FEATURE:
<223> OTHER INFORMATION: Synthetic

<400> SEQUENCE: 128

Ile His Phe Leu Ile Arg Gln Leu Ile Arg Leu Leu Thr Trp Leu Phe
1               5                   10                  15

Ser Asn Cys Arg Thr Leu Leu Ser Arg
            20                  25

<210> SEQ ID NO 129
<211> LENGTH: 25
<212> TYPE: PRT
<213> ORGANISM: Artificial Sequence
<220> FEATURE:
<223> OTHER INFORMATION: Synthetic

<400> SEQUENCE: 129

Thr Trp Leu Phe Ser Asn Cys Arg Thr Leu Leu Ser Arg Val Tyr Gln
1               5                   10                  15

Ile Leu Gln Pro Ile Leu Gln Arg Leu
            20                  25

<210> SEQ ID NO 130
<211> LENGTH: 25
<212> TYPE: PRT
<213> ORGANISM: Artificial Sequence
<220> FEATURE:
<223> OTHER INFORMATION: Synthetic

<400> SEQUENCE: 130

Arg Val Tyr Gln Ile Leu Gln Pro Ile Leu Gln Arg Leu Ser Ala Thr
1               5                   10                  15

Leu Gln Arg Ile Arg Glu Val Leu Arg
            20                  25

<210> SEQ ID NO 131
<211> LENGTH: 25
<212> TYPE: PRT
<213> ORGANISM: Artificial Sequence

```
<220> FEATURE:
<223> OTHER INFORMATION: Synthetic

<400> SEQUENCE: 131

Leu Ser Ala Thr Leu Gln Arg Ile Arg Glu Val Leu Arg Thr Glu Leu
1               5                   10                  15

Thr Tyr Leu Gln Tyr Gly Trp Ser Tyr
            20                  25

<210> SEQ ID NO 132
<211> LENGTH: 25
<212> TYPE: PRT
<213> ORGANISM: Artificial Sequence
<220> FEATURE:
<223> OTHER INFORMATION: Synthetic

<400> SEQUENCE: 132

Arg Thr Glu Leu Thr Tyr Leu Gln Tyr Gly Trp Ser Tyr Phe His Glu
1               5                   10                  15

Ala Val Gln Ala Val Trp Arg Ser Ala
            20                  25

<210> SEQ ID NO 133
<211> LENGTH: 25
<212> TYPE: PRT
<213> ORGANISM: Artificial Sequence
<220> FEATURE:
<223> OTHER INFORMATION: Synthetic

<400> SEQUENCE: 133

Tyr Phe His Glu Ala Val Gln Ala Val Trp Arg Ser Ala Thr Glu Thr
1               5                   10                  15

Leu Ala Gly Ala Trp Gly Asp Leu Trp
            20                  25

<210> SEQ ID NO 134
<211> LENGTH: 25
<212> TYPE: PRT
<213> ORGANISM: Artificial Sequence
<220> FEATURE:
<223> OTHER INFORMATION: Synthetic

<400> SEQUENCE: 134

Ala Thr Glu Thr Leu Ala Gly Ala Trp Gly Asp Leu Trp Glu Thr Leu
1               5                   10                  15

Arg Arg Gly Gly Arg Trp Ile Leu Ala
            20                  25

<210> SEQ ID NO 135
<211> LENGTH: 27
<212> TYPE: PRT
<213> ORGANISM: Artificial Sequence
<220> FEATURE:
<223> OTHER INFORMATION: Synthetic

<400> SEQUENCE: 135

Trp Glu Thr Leu Arg Arg Gly Gly Arg Trp Ile Leu Ala Ile Pro Arg
1               5                   10                  15

Arg Ile Arg Gln Gly Leu Glu Leu Thr Leu Leu
            20                  25

<210> SEQ ID NO 136
<211> LENGTH: 7
<212> TYPE: PRT
```

-continued

```
<213> ORGANISM: Artificial Sequence
<220> FEATURE:
<223> OTHER INFORMATION: Synthetic

<400> SEQUENCE: 136

Ser Tyr Asn Phe Glu Lys Leu
1               5
```

METHOD OF MAKING MODIFIED IMMUNODEFICIENCY VIRUS PARTICLES

RELATED APPLICATIONS

The present application claims the benefit of U.S. provisional patent application Ser. No. 60/670,574, filed Apr. 11, 2005, U.S. provisional patent application Ser. No. 60/669,738, filed Apr. 8, 2005, and is a continuation-in-part of U.S. non-provisional patent application Ser. No. 10/873,015, filed Jun. 21, 2004, now U.S. Pat. No. 7,407,662, which is a continuation in part of U.S. non-provisional patent application Ser. No. 10/601,656 filed Jun. 20, 2003, now U.S. Pat. No. 7,407,663, which is a continuation-in-part of U.S. non-provisional patent application Ser. No. 10/311,679, filed Dec. 18, 2002, now abandoned, which is a U.S. national phase from PCT patent application number PCT/IB01/01099, filed Jun. 21, 2001, which claims the benefit of Australian patent application PQ8469, filed Jun. 29, 2000, and PCT patent application Ser. No. PCT/AU00/01603 filed Dec. 28, 2000. U.S. patent application Ser. No. 10/601,656, filed Jun. 20, 2003, also claims the benefit of U.S. provisional patent application Ser. No. 60/390,066, filed Jun. 20, 2002. U.S. non-provisional patent application Ser. No. 10/873,015, filed Jun. 21, 2004, also claims the benefit of U.S. provisional patent application Ser. No. 60/491,928 filed Aug. 1, 2003, 60/533,542 filed Dec. 31, 2003, and 60/542,947 filed Feb. 9, 2004.

FIELD OF THE INVENTION

The present invention relates to a delipidation method employing a solvent system useful for extracting lipids from a virus, thereby creating a modified viral particle. The solvent system of the present invention is optimally designed such that upon delipidation of the virus, the viral particle remains substantially intact. By dissolving the lipid envelope surrounding the viral particle using the method of the present invention, the resultant modified viral particle has exposed antigens (or epitopes), which foster and promote cellular responses and antibody production when introduced into a human or an animal. The resulting modified viral particle of the present invention initiates a positive immunogenic response in the species into which it is re-introduced. The present invention can be applied to delipidating viruses from a specific patient for future reintroduction into the patient, to delipidating stock viruses, or non-patient specific viruses, for use as a vaccine, or to delipidating and combining both non-patient specific viruses and patient specific viruses to create a therapeutic cocktail.

BACKGROUND OF THE INVENTION

Introduction

Viruses, of varied etiology, affect billions of animals and humans each year and inflict an enormous economic burden on society. Many viruses contain lipid as a major component of the membrane that surrounds them. Viruses affect animals and humans causing extreme suffering, morbidity, and mortality. These viruses travel throughout the body in biological fluids such as blood, peritoneal fluid, lymphatic fluid, pleural fluid, pericardial fluid, cerebrospinal fluid, and in various fluids of the reproductive system. Fluid contact at any site promotes transmission of disease. Other viruses reside primarily in different organ systems and in specific tissues, proliferate and then enter the circulatory system to gain access to other tissues and organs at remote sites. If the body does not exhibit a positive immune response against these pathogens, they infect many cell types within the body, inhibiting these cells from performing their normal functions.

The human immune system is composed of various cell types that collectively protect the body from different viruses. The immune system provides multiple means for targeting and eliminating foreign elements, including humoral and cellular immune responses, participating primarily in antigen recognition and elimination. An immune response to foreign elements requires the presence of B-lymphocytes (B cells) or T-lymphocytes (T cells) in combination with antigen-presenting cells (APC), which are usually macrophage or dendrite cells. The APCs are specialized immune cells that capture antigens. Once inside an APC, antigens are broken down into smaller fragments called epitopes—the unique markers carried by the antigen surface. These epitopes are subsequently displayed on the surface of the APCs and are responsible for triggering an antibody response in defense of the infection.

In a humoral immune response, when an APC displaying antigens (in the form of unique epitope markers) foreign to the body are recognized, B cells are activated, proliferating and producing antibodies. These antibodies specifically bind to the antigens present on the virus. After the antibody attaches, the APC engulfs the entire antigen and kills it. This type of antibody immune response is primarily involved in the prevention of viral infection.

In a cellular immune response, T cells are activated on recognizing the antigen displayed on the APC. There are two steps in the cellular immune response. The first step involves activation of cytotoxic T cells (CTL) or $CD8^+$ T killer cells that proliferate and kill target cells that specifically present antigens. The second involves helper T cells (HTL) or $CD4^+$ T cells that regulate the production of antibodies and the activity of $CD8^+$ cells. The $CD4^+$ T cells provide growth factors to $CD8^+$ T cells that allow them to proliferate and function efficiently.

Certain infective pathogens are deemed "chronic" due to their structure. For example, some viruses are able to evade an immune response because of their ability to hide some of their antigens from the immune system. Viruses contain an outer envelope made up of lipids and fats derived from the host cell membrane during the budding process. Viruses are comprised of virions, non-cellular infectious agents consisting of a single type of nucleic acid (either RNA or DNA), surrounded by a protein coat. The outer protein covering of viruses is called a capsid, made up of repeating subunits called capsomeres.

Since viruses are non-metabolic, they only reproduce within living host cells. The virus codes the proteins of the viral envelope while the host cell codes the lipids and carbohydrates. Therefore, the lipid and carbohydrate content within a given viral envelope is dependent on the particular host. The enveloped viral particles therefore partially adopt the identity of the host cell, via lipid and carbohydrate content, and are able to conceal antigens associated with them, which would normally have initiated an immune response. Instead, the viral particle confuses the host immune system by presenting it with an antigenic complex that contains components of host tissues, and is perceived by the host immune system as partly "self" and partly "foreign". The immune system is forced to produce the "compromise", ineffective antibodies which do not destroy the viral particles, allowing them to proliferate and slowly cause severe damage to the body, while destroying host cells.

Recent epidemics affecting the immune system include acquired immune deficiency syndrome (AIDS), believed to be caused by the human immunodeficiency virus (HIV). Related viruses affect animal species, for example, simians and felines (SIV and FIV, respectively). Other major viral infections include, but are not limited to, meningitis, cytomegalovirus, and hepatitis in its various forms.

Current Methods of Treatment

One prior art method of treating viruses of varied etiology is via drug therapy. Most anti-viral drug therapies are directed toward preventing or inhibiting viral replication and appear to focus on the initial attachment of the virus to the T4 lymphocyte or macrophage, the transcription of viral RNA to viral DNA and the assembly of new virus during replication. The high mutation rate of the virus, especially in the case of HIV, is a major difficulty with existing treatments because the various strains become resistant to anti-viral drug therapy. Furthermore, anti-viral drug therapy treatment may cause the evolution of resistant strains of the virus. Other drawbacks to drug therapies are the undesirable side effects and patient compliance requirements. In addition, many individuals are afflicted with multiple viral infections such as a combination of HIV and hepatitis. Such individuals require even more aggressive and expensive drug regimens to counteract disease progression, which in turn cause greater side effects and a greater likelihood of multiple drug resistance. The most effective approach to date for treating HIV is the use of highly active antiretroviral therapy (HAART) which is expensive, toxic to the patient, and does not eradicate the virus. Strict adherence to HAART regimen remains a major hurdle, and lapses in compliance lead to bursts of viral replication, and selection of drug resistant strains. Additionally, long-term use of HAART is associated with side effects such as lipodystrophies, altered glucose metabolism and elevated cholesterol and triglycerides in plasma. There is, therefore, a pressing need for additional therapies, either in form of preventative and therapeutic vaccines, or development of immunomodulating agents to augment HAART. The current approaches to HIV vaccine development are reviewed by Mwau et al (2003. A review of vaccines for HIV prevention. *J Gene Med* 5:3.). Briefly, strategies include a variety of expression vectors, DNA based recombinant vaccines, combinations of DNA based vaccines and viral protein boosts with or without adjuvant. A recent Phase III clinical trial using recombinant gp120 vaccine in Thailand, for example, ended without success (Cohen, J. 2003. Public health. AIDS vaccine still alive as booster after second failure in Thailand. *Science* 302:1309), possibly because recombinant viral proteins need to be in the correct configuration for appropriate immune responses to be generated. Clearly, other novel approaches to enhancing immune responses to viral antigens need to be evaluated.

Also known in the prior art is prevention of disease via the use of vaccinations. Vaccines have been singularly responsible for conferring immune response against several human pathogens. They are designed to stimulate the immune system to protect against various viral infections. In general, a vaccine is produced from an antigen, isolated or produced from the disease-causing microorganism, which can elicit an immune response. When a vaccine is injected into the blood stream as a preventive measure to create an effective immune response, the B cells in the blood stream perceive the antigens contained by the vaccine as foreign or "non-self" and respond by producing antibodies, which bind to the antigens and inactivate them. Memory cells are thereby produced and remain ready to mount a quick protective immune response against subsequent infection with the same disease-causing agent. Thus when an infective pathogen containing similar antigens as the vaccine enters the body, the immune system will recognize the protein and instigate an effective defense against infection.

The current methods of vaccination do have drawbacks, making them less than optimally desirable for immunizing individuals against particular pathogens, especially HIV. The existing vaccine strategies aim to expose the body to the antigens associated with infective pathogens so that the body builds an immune response against these pathogens. For example, hepatitis B and HIV pathogens are able to survive and proliferate in the human body despite the immune response. One explanation offered in the prior art is that the antigens of these microorganisms change constantly so the antibodies produced in response to a particular antigen are no longer effective when the antigen mutates. The AIDS virus is believed to undergo this antigenic variation. Although antigenic variation has been addressed via the attempted use of combination drugs or antigens, no prior art vaccine has succeeded in addressing chronic infections such as HIV.

Another approach to treating viruses of varied etiology is to inactivate the virus. Prior art methods of inactivating viruses using chemical agents have relied on organic solvents such as chloroform or glutaraldehyde. Viral inactivation does present problems since inactivation of a virus does not provide a protective immune response against viral infection. In addition, it is largely geared towards denaturing viral proteins, thereby destroying the structure of the viral particle. In sum, prior art methods have largely focused on destroying, yet not suitably modifying, viral particles to produce an immune response.

Current Methods of Manufacture of Viral Treatments and Medicaments Viral Inactivation (or Chemical Kill)

Described in the prior art are methods of treating viral particles with organic solvents and high temperatures thus dissolving the lipid envelopes and subsequently inactivating the virus. In those methods, blood is withdrawn from the patient and separated into two phases—the first phase including red cells and platelets and the second phase containing plasma, white cells, and cell-free virus (virion). The second phase is treated with an organic solvent, thereby killing the infected cells and virions, and subsequently reintroduced into the patient. In addition to dissolving the lipid envelope of the virus, the high organic solvent concentrations cause cell death and damage to the antigens. Essentially, this method results in a "chemical kill" of the cell.

Glutaraldehyde is one such solvent whereby cell inactivation is achieved as known by those of ordinary skill in the art by fixation with a dilute solution of glutaraldehyde at about 1:250. Although treating the virus with glutaraldehyde effectively delipidates the virus, it also destroys the core. Destruction of the core is not desirable for producing a modified viral particle useful for inducing an immune response in a recipient.

Chloroform is another such solvent. Chloroform, however, denatures many plasma proteins and is not suitable for use with biological fluids, which will be reintroduced into the animal or human. These plasma proteins deleteriously affected by chloroform serve important biological functions including coagulation, hormonal response, and immune response. These functions are essential to life and thus damage to these proteins may have an adverse effect on a patient's health, possibly leading to death.

Other solvents or detergents such as B-propiolactone, TWEEN-80, and dialkyl or trialkyl phosphates have been used, either alone or in combination. Many of these methods, especially those involving detergents, require tedious procedures to ensure removal of the detergent before reintroduction of the treated plasma sample into the animal or human. Further, many of the methods described in the prior art involve extensive exposure to elevated temperature in order to kill free virus and infected cells. Elevated temperatures have deleterious effects on the proteins contained in biological fluids, such as plasma.

Current Methods of Manufacturing Vaccines

To date, several manufacturing methods have been employed in search of safe and effective vaccines for immunizing individuals against infective pathogenic agents. To protect an individual from a specific pathogenic infection, a target protein or antigen associated with the infective pathogen is administered to the individual. This includes presenting the protein as part of a non-infective (inactivated) or less infective (attenuated) agent or as a discrete protein composition. Known to one of ordinary skill in the art are the following different types of vaccines: live attenuated vaccines, whole inactivated vaccines, DNA vaccines, combination vaccines, recombinant vaccines, live recombinant vector vaccines, virus like particles and synthetic peptide vaccines.

In live attenuated vaccines, the viruses are rendered less pathogenic to the host, either by specific genetic manipulation of the virus genome or by passage in some type of tissue culture system. In order to achieve genetic manipulation, an inessential gene is deleted or one or more essential genes in the virus are partially damaged. Upon genetic manipulation, the viral particles become less virulent yet retain antigenic features. Live attenuated vaccines can also be used as "vaccine vectors" for other genes, wherein they act as carriers of genes from a second virus (or other pathogen) against which protection is required. Attenuated vaccines (less infective and not inactivated), however, pose several problems. First, it is difficult to ascertain when the attenuated vaccine is no longer pathogenic. The risk of viral infection from the vaccine is too great to properly test for effective attenuation. In addition, attenuated vaccines carry the risk of reverting into a virulent form of the pathogen.

Whole inactivated vaccines are known in the art for immunizing against infection by introducing killed or inactivated viruses to introduce pathogen proteins to an individual's immune system. The administration of killed or inactivated pathogens, via heat or chemical means, into an individual introduces the pathogens to the individual's immune system in a non-infective form thereby initiating an immune response defense. Wholly inactivated vaccines provide protection by directly generating cellular and humoral immune responses against the pathogenic immunogens. There is little threat of infection, because the viral pathogen is killed or otherwise inactivated.

Subunit vaccines are yet another form of vaccination well known to one of ordinary skill in the art. These consist of one or more isolated proteins derived from the pathogen. These proteins act as target antigens against which an immune response is exhibited. The proteins selected for the subunit vaccine are displayed by the pathogen so that upon infection of an individual by the pathogen, the individual's immune system recognizes the pathogen and instigates an immune response. Subunit vaccines are not whole infective agents and are therefore incapable of becoming infective. Subunit vaccines are the basis of AIDSVAX, the first vaccine for HIV being tested for effectiveness in humans and which contains a portion of HIV's outer surface (envelope) protein, called gp120.

DNA vaccine is another type known in the art and uses actual genetic material of pathogens. In addition, synthetic peptide vaccines are made up of parts of synthetic, chemically engineered HIV proteins called peptides. They comprise portions of HIV proteins chosen specifically to achieve an anti-HIV immune response. Also mentioned in the prior art are combination vaccines that, when used in conjunction with one another, generate a broad spectrum of immune responses. One example of a combination virus is SHIV, which is a synthetic virus made from the HIV envelope and SIV core.

What is needed is a therapeutic method and system for providing patients with patient-specific viral antigens capable of initiating a protective immune response. Accordingly, what is needed is a simple, effective method that does not appreciably denature or extract proteins from the biological sample being treated. What is also needed is an effective delipidation process via which a viral particle is modified, rather than destroyed, thereby both reducing and/or eliminating infectivity of the viral particle and invoking a patient specific, autologous immune response to further reduce viral infection and prevent further infection.

What is also needed is an effective means to immunize individuals against viral pathogen infection that is unique to the individual due to viral mutations. Preferably the means would elicit a broad protective immune response with minimized risk of infecting the individual.

SUMMARY OF THE INVENTION

The present invention solves the problems described above by providing a simple, effective and efficient method for treating and preventing viral infection. The method of the present invention affects the lipid envelope of a virus by utilizing an efficient solvent system, which does not denature or destroy the virus. The present invention employs an optimal solvent and energy system to create, via delipidation, a non-synthetic, host-derived or non host-derived modified viral particle that has its lipid envelope at least partially removed, generating a positive immunologic response when administered to a patient, thereby providing that patient with some degree of protection against the virus. It is believed that these modified viral particles have at least one antigen exposed that was not exposed prior to the delipidation process.

The present invention is also effective in producing an autologous, patient-specific therapeutic vaccine against the virus, by treating a biological fluid containing the virus such that the virus is present in a modified form, with reduced infectivity, and such that an immune response is initiated upon reintroduction of the fluid with reduced lipid content into the patient. This autologous method ensures that patient specific antigens, for example patient specific viral antigens, are introduced into the same patient from which they were obtained to induce an immune response. This is an important feature since a patient's physiology may modify the antigens present in an infectious organism such as a virus. To create the vaccine, a biological fluid (for example, blood) is removed from the patient, the plasma is separated from the blood and treated to reduce the lipid content of the virus in the plasma using an optimal solvent system. A lipid-containing virus, treated in this manner in order to reduce its infectivity and create a modified viral particle with reduced lipid content is administered to a patient, such as an animal or a human, optionally together with a pharmaceutically acceptable carrier, in order to initiate an immune response in the animal or human and create antibodies that bind the exposed epitopes of the modified viral particle. Adjuvants may also be administered with the modified viral particle in the pharmaceutically acceptable carrier or separately.

The present method is also employed to produce non-autologous vaccines, wherein biological fluids with lipid containing viruses from at least one animal or human are treated to produce a modified viral particle for administration into a different (non-autologous) animal or human. The present invention is also effective in producing an non-autologous, vaccine against the virus, by treating a biological fluid such as plasma obtained from an animal or a human with the present method to reduce lipid levels in the fluid and in the virus within the fluid. Such treated fluid with reduced lipid levels and containing modified virus with reduced lipid levels may be introduced into another animal or human which was not the source of the treated biological fluid. This non-autologous method is employed to vaccinate a recipient animal or human against one or more infectious organisms such as viruses. Biological fluids may be used from animals or humans infected with one or more infectious organisms such as viruses, and treated with the present methods to produce a vaccine for administration to a recipient animal or human.

Alternatively, or in addition, various stock supplies of virus may be added to a biological fluid before treating the fluid with the method of the present invention to create a vaccine.

The present invention encompasses vaccines made with the delipidation method of the present invention that include more than one strain of the same infectious organism, for example more than one lade of HIV virus (e.g., HIV-1 and HIV-2). Such vaccines provide an immune response to more than one strain of the same infectious organism. Any number of different infectious strains or clades of the same virus may be chosen and treated with the delipidation method of the present invention to form numerous vaccines. Alternatively, or in addition, various stock supplies of different strains or clades of virus may be added to a biological fluid before treating the fluid with the method of the present invention to create a vaccine capable of generating an immune response. Stocks of one or more viral preparation may be employed to make a non-autologous vaccine directed to one or more viruses. In this manner combination vaccines are produced which provide protection against multiple strains or clades of a virus or against multiple viruses.

The present invention encompasses vaccines made with the delipidation method of the present invention that include more than one infectious organism, such as more than one virus. Such combination vaccines provide an immune response to more than one infectious organism, for example, HIV and hepatitis. Any number of different infectious organisms may be chosen and treated with the delipidation method of the present invention to form numerous combination vaccines.

Thus an effective method is presented, by which new vaccines can be developed from lipid containing viruses by removing lipid from the lipid envelope and exposing antigens hidden within the lipid envelope or beneath the surface of the lipid envelope, in turn generating an immune response when re-introduced into the patient.

The present invention provides a modified viral particle comprising at least a partially delipidated viral particle, wherein the partially delipidated viral particle initiates an immune response in a patient and incites protection against an infectious organism in the patient.

The present invention provides a method for creating a modified viral particle comprising the steps of: receiving a plurality of viral particles, each having a viral envelope, in a fluid; exposing the viral particles to a delipidation process; and, partially delipidating the viral particles wherein the delipidation process at least partially removes the viral envelopes to create the modified viral particle and wherein the modified viral particle is capable of provoking a positive immune response in a patient.

The present invention also provides an antigen delivery vehicle and a method for creating an antigen delivery vehicle comprising the steps of: receiving a plurality of viral particles, each having a viral envelope, in a fluid; exposing the viral particles to a delipidation process; and, partially delipidating the viral particles to create modified viral particles that act as antigen delivery vehicles, wherein the delipidation process at least partially removes the viral envelopes to expose at least one antigen and wherein the at least one antigen is capable of provoking a positive immune response in a patient.

The modified viral particles of the present invention comprise at least a partially delipidated viral particle, wherein the partially delipidated viral particle is produced by exposing a non-delipidated viral particle to a delipidation process and wherein the partially delipidated viral particle comprises at least one exposed patient specific antigen that was not exposed in the non-delipidated viral particle.

The present invention also provides a vaccine composition, comprising at least a partially delipidated viral particle having patient-specific viral antigens and optionally a pharmaceutically acceptable carrier, wherein the partially delipidated viral particle is capable of provoking a positive immune response when the composition is administered to a patient.

The present invention also provides a method for making a vaccine comprising: contacting a lipid-containing viral particle in a fluid with a first organic solvent capable of extracting lipid from the lipid-containing viral particle; mixing the fluid and the first organic solvent for a time sufficient to extract lipid from the lipid-containing viral particle; permitting organic and aqueous phases to separate; and collecting the aqueous phase containing a modified viral particle with reduced lipid content wherein the modified viral particle is capable of provoking a positive immune response when administered to a patient.

The present invention also provides a method to protect a patient against an infectious viral particle comprising administering to the patient an effective amount of a composition comprising a modified viral particle, wherein the modification comprises at least partial removal of a lipid envelope of the infectious viral particle, and optionally a pharmaceutically acceptable carrier, wherein the amount is effective to provide a protective effect against infection by the infectious viral particle in the animal or the human.

The present invention also provides a method for provoking a positive immune response in a patient having a plurality of lipid-containing viral particles, comprising the steps of: obtaining a fluid containing the lipid-containing viral particles from the patient; contacting the fluid containing the lipid-containing viral particles with a first organic solvent capable of extracting lipid from the lipid-containing viral particles; mixing the fluid and the first organic solvent; permitting organic and aqueous phases to separate; collecting the aqueous phase containing modified viral particles with reduced lipid content; and introducing the aqueous phase containing the modified viral particles with reduced lipid content into the animal or the human wherein the modified viral particles with reduced lipid content provoke a positive immune response in the animal or the human.

The present invention also provides a method for treating a viral infection in a patient comprising: removing blood containing a plurality of lipid-containing infectious viral particles from the patient; obtaining plasma from the blood, the plasma containing the lipid-containing infectious viral particles; contacting the plasma containing the lipid-containing infectious viral particles with a first organic solvent capable of extracting lipid from the lipid-containing infectious viral particles to produce modified viral particles having reduced lipid content; mixing the plasma and the first organic solvent; permitting organic and aqueous phases to separate; collecting the aqueous phase containing the modified viral particles; removing residual solvent from the aqueous phase; and, introducing the aqueous phase containing the modified viral particles into the patient wherein the modified viral particles have at least one exposed patient-specific antigen that was not exposed in the plurality of lipid-containing infectious viral particles. Introduction of these modified viral particles into the patient produces an immune response to treat or lessen the severity of the viral infection.

The present invention also provides a method for treating a viral infection in a patient comprising: obtaining a fluid comprising plurality of lipid-containing infectious viral particles from a plurality of patients; optionally combining the lipid-containing infectious viral particles with a suitable biologically acceptable carrier; contacting the fluid containing lipid-containing infectious viral particles with a first organic solvent capable of extracting lipid from the lipid-containing infectious viral particles to produce modified viral particles having reduced lipid content; mixing the carrier and the first organic solvent; permitting organic and aqueous phases to separate; collecting the aqueous phase containing the modified viral particles; and introducing the aqueous phase containing the modified viral particles into a different patient wherein the modified viral particles have at least one exposed antigen that was not exposed in the plurality of lipid-containing infectious viral particles. In this embodiment, the lipid-containing infectious viral particles represent one or more viral strains or one or more types of virus and are not patient specific. Introduction of these modified viral particles into the patient produces an immune response to treat or lessen the severity of the viral infection.

As shown below, the characteristics of the modified viral particle are exhibited in experimental data, showing mice having a positive immunogenic response when vaccinated as compared with a wholly inactivated vaccine. In addition, data exhibiting protein recovery indicate retention of the structural integrity of the viral particle, removing only its lipid-containing envelope.

Fluids which may be treated with the method of the present invention include but are not limited to the following: plasma; serum; lymphatic fluid; cerebrospinal fluid; peritoneal fluid; pleural fluid; pericardial fluid; various fluids of the reproductive system including but not limited to semen, ejaculatory fluids, follicular fluid and amniotic fluid; cell culture reagents such as normal sera, fetal calf serum or serum derived from any other animal or human; and immunological reagents such as various preparations of antibodies and cytokines.

The method of the present invention may be used to treat viruses containing lipid in the viral envelope. Preferred viruses to be treated with the method of the present invention include the various immunodeficiency viruses including but not limited to human (HIV) and subtypes and clades such as HIV-1 and HIV-2, simian (SIV), feline (FIV), as well as any other form of immunodeficiency virus. Other preferred viruses to be treated with the method of the present invention include but are not limited to hepatitis in its various forms. Another preferred virus treated with the method of the present invention is the bovine pestivirus. Another preferred virus treated with the method of the present invention is the coronavirus SARS. It is to be understood that the present invention is not limited to the viruses provided in the list above. Additional specific viruses are described in the detailed description of this application. All viruses containing lipid, especially in their viral envelope, are included within the scope of the present invention.

Accordingly, it is an object of the present invention to provide a method for treating lipid containing virus in order to create modified viral particles.

It is an object of the present invention to provide a method for treating lipid containing virus in order to create modified viral particles with reduced lipid content while substantially unaffecting protein levels when compared to unmodified viral particles.

Yet another object of the present invention is to provide a method for treating lipid containing virus in order to create modified viral particles with reduced lipid content, with substantially unaffected protein levels when compared to unmodified viral particles, and with at least one exposed antigen associated with the viral particles that was substantially unexposed in unmodified viral particles.

It is another object of the present invention to provide a method for treating or preventing viral disease by administering to a patient modified viral particles with reduced lipid content and at least one exposed antigen associated with the viral particles that was substantially unexposed in unmodified viral particles.

Another object of the present invention is to provide a method for treating a biological fluid in order to reduce or eliminate the infectivity of infectious viral organisms contained therein.

Yet another object of the present invention is to provide a method for creating, in a biological fluid, a plurality of modified lipid containing viral particles having a distribution of reduced lipid content, with a substantial percentage of viral particles having substantially unaffected protein levels when compared to unmodified viral particles.

It is further an object of the present invention to provide a method for treatment of lipid-containing viruses within a fluid, which minimizes deleterious effects on proteins contained within the fluid, thereby creating a modified viral particle with properties that are capable of initiating a positive immune response in a patient.

It is a further object of the present invention to provide a method for treatment of lipid-containing viruses within a fluid, which minimizes deleterious effects on proteins contained within the fluid, thereby creating a modified viral particle with patient-specific viral antigens.

It is another object of the present invention to provide a method for reducing the infectivity of viruses, wherein the method exposes antigenic determinants on the modified viral particle.

Another object of the present invention is to completely or partially delipidate viral particles, wherein the viral particles comprise immunodeficiency virus, hepatitis in its various forms, coronavirus, or any other lipid-containing virus, thereby creating a modified viral particle.

It is a further object of the present invention to completely or partially delipidate viral particles, wherein the viral particles comprise immunodeficiency virus, hepatitis in its various forms, coronavirus, or any other lipid-containing virus, while retaining the structural protein core of the virus.

It is another object of the present invention to provide a method for reducing the infectivity of viruses, wherein the newly formed viral particle can be used as an antigen delivery vehicle.

Yet another object of the present invention is to treat infectious organisms with the method of the present invention in order to reduce their infectivity and provide a vaccine comprising a modified viral particle with reduced lipid content which may be administered to an animal or a human, optionally with a pharmaceutically acceptable carrier and optionally an immunostimulant compound, to prevent or minimize clinical manifestation of disease in a patient following exposure to the virus.

Still another object of the present invention is to treat infectious organisms with the method of the present invention in order to reduce their infectivity and provide a vaccine comprising a modified viral particle with reduced lipid content which may be administered to an animal or a human optionally with a pharmaceutically acceptable carrier and optionally an immunostimulant compound, to initiate a positive immunogenic response in the animal or human.

It is another specific object of the present invention to provide an anti-viral vaccine.

Another specific object of the present invention is to provide an anti-viral vaccine that induces cellular responses in cells of the immune system, wherein the cellular responses include but are not limited to proliferation of cells and production of immune system molecules such as interferon gamma.

It is a further specific object of the present invention to lessen the severity of a disease caused by a lipid-containing virus in an animal or human receiving a vaccine comprising a composition comprising a virus treated with the method of the present invention, optionally combined with a pharmaceutically acceptable carrier.

It is another object of the present invention to combine viral particles with reduced lipid content having patient specific antigens with delipidated stock viral particles with reduced lipid content to create a therapeutic combination vaccine for the treatment or prevention of more than one viral disease.

These and other features and advantages of the present invention will become apparent after review of the following drawings and detailed description of the disclosed embodiments. Various modifications to the stated embodiments will be readily apparent to those of ordinary skill in the art, and the disclosure set forth herein may be applicable to other embodiments and applications without departing from the spirit and scope of the present invention.

BRIEF DESCRIPTION OF THE DRAWINGS

The accompanying drawings, which are incorporated in and form a part of the specification, illustrate preferred embodiments of the present invention.

DETAILED DESCRIPTION OF THE INVENTION

Definitions

Figure 1:
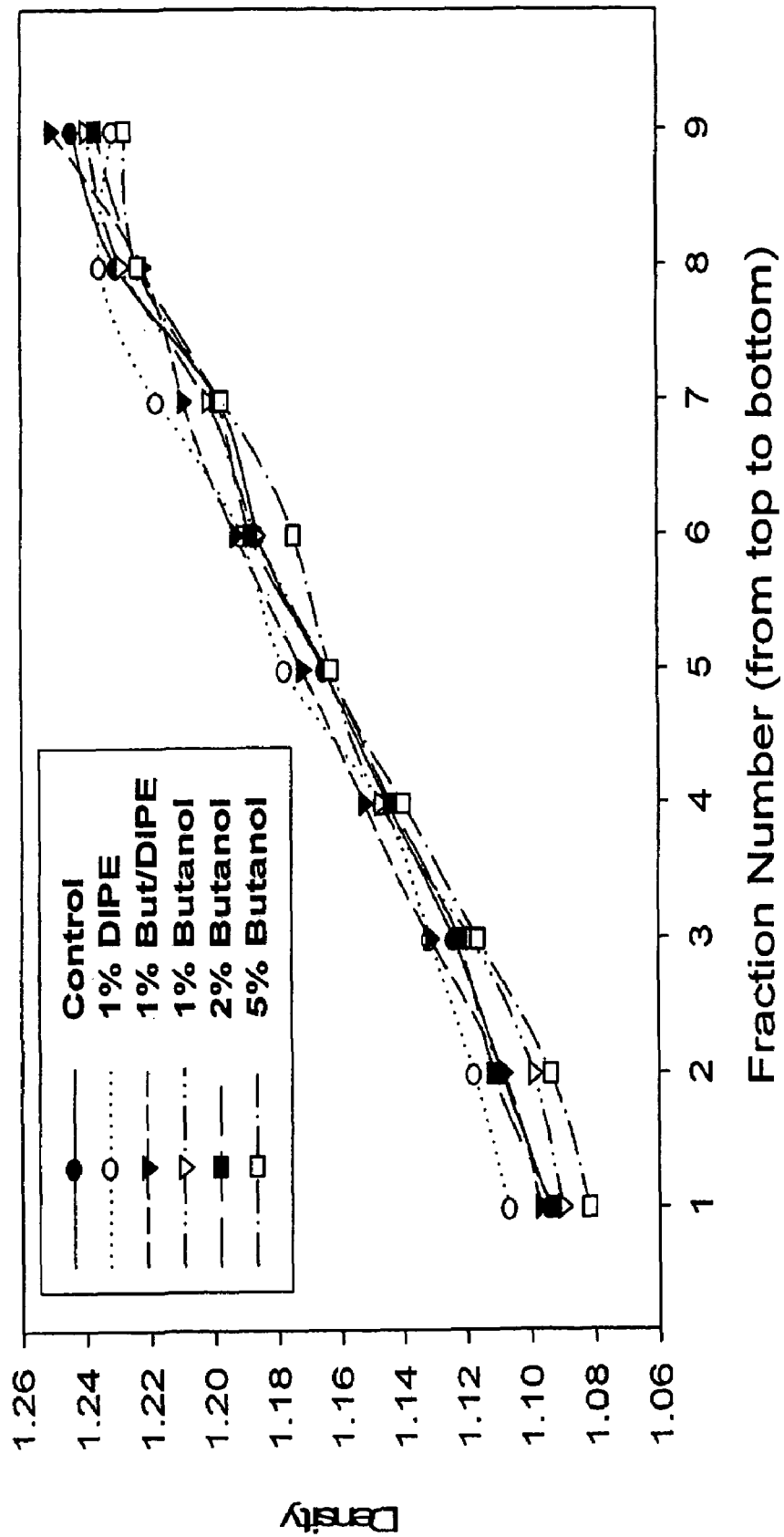
FIG. 1 depicts the density of sucrose gradient fractions as indicated by the graphing of density against fraction number for HIV viral particles subjected to delipidation using 1% DIPE, 1% butanol/DIPE, 1% butanol, 2% butanol, and 5% butanol, along with a control group.

By the term "fluid" is meant any fluid containing an infectious organism, including but not limited to, a biological fluid obtained from an organism such as an animal or human. Preferred infectious organisms treated with the method of the present invention are viruses. Such biological fluids obtained from an organism include but are not limited to blood, plasma, serum, cerebrospinal fluid, lymphatic fluid, peritoneal fluid, follicular fluid, amniotic fluid, pleural fluid, pericardial fluid, reproductive fluids and any other fluid contained within the organism. Other fluids may include laboratory samples containing infectious organisms suspended in any chosen fluid. Other fluids include cell culture reagents, many of which include biological compounds such as fluids obtained from living organisms, including but not limited to "normal serum" obtained from various animals and used as growth medium in cell and tissue culture applications.

By the terms "first solvent" or "first organic solvent" "or first extraction solvent" are meant a solvent, comprising one or more solvents, used to facilitate extraction of lipid from a fluid or from a lipid-containing biological organism in the fluid. This solvent will enter the fluid and remain in the fluid until being removed. Suitable first extraction solvents include solvents that extract or dissolve lipid, including but not limited to alcohols, hydrocarbons, amines, ethers, and combinations thereof. First extraction solvents may be combinations of alcohols and ethers. First extraction solvents include, but are not limited to n-butanol, di-isopropyl ether (DIPE), diethyl ether, and combinations thereof.

The term "second extraction solvent" is defined as one or more solvents that may be employed to facilitate the removal of a portion of the first extraction solvent. Suitable second extraction solvents include any solvent that facilitates removal of the first extraction solvent from the fluid. Second extraction solvents include any solvent that facilitates removal of the first extraction solvent including but not limited to ethers, alcohols, hydrocarbons, amines, and combinations thereof. Preferred second extraction solvents include diethyl ether and di-isopropyl ether, which facilitate the removal of alcohols, such as n-butanol, from the fluid. The term "de-emulsifying agent" is a second extraction solvent that assists in the removal of the first solvent which may be present in an emulsion in an aqueous layer.

The term "delipidation" refers to the process of removing at least a portion of a total concentration of lipids in a fluid or in a lipid-containing organism. Lipid-containing organisms may be found within fluids which may or may not contain additional lipids.

The terms "pharmaceutically acceptable carrier" or "pharmaceutically acceptable vehicle" are used herein to mean any liquid including but not limited to water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The term "patient" refers to animals and humans.

The term "patient specific antigen" refers to an antigen that is capable of inducing a patient specific immune response when introduced into that patient. Such patient specific antigens may be viral antigens. A patient specific antigen includes any antigen, for example a viral antigen, that has been modified or influenced within the patient.

A Modified Viral Particle

Figure 21:
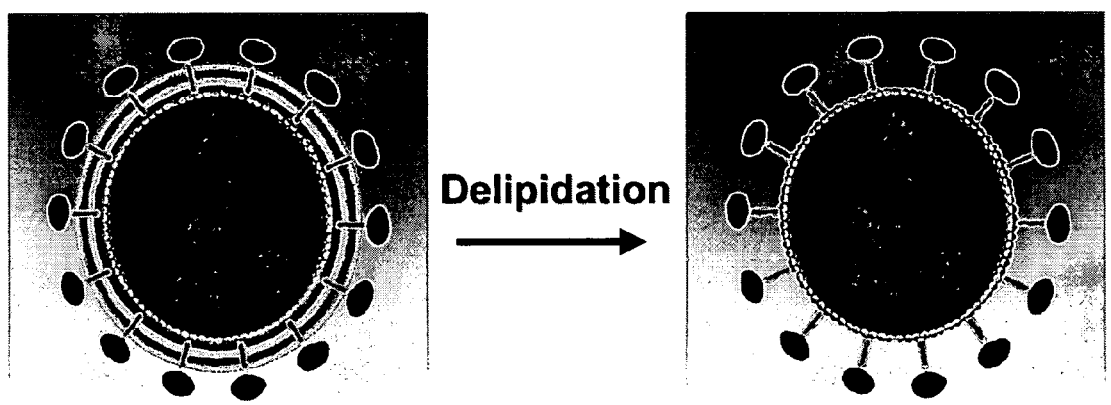
FIG. 21 is a schematic illustration of a modified, partially delipidated viral particle.

Practice of the method of the present invention to reduce the lipid content of a virus creates a modified viral particle. These modified viral particles have lower levels of cholesterol and are immunogenic. The present methods expose epitopes that are not usually presented to the immune system by untreated virus. A structural change occurs in the modified viral particles, and proteins on, in, or near the surface of the virus are modified such that a conformational change occurs. Some of these proteins may also separate from the modified viral particle. A schematic representation of HIV viral particles contain the lipid containing envelope or bilayer derived from a host cell, surface glycoproteins, transmembrane proteins, the capsid, capsid proteins and nuclear material is presented on page 238 of Robbins Pathologic Basis of Disease (Cotran et al. eds $6^{th}$ edition, W. B. Saunders Co., 1999). The delipidation process of the present invention modifies the viral particle as schematically illustrated in FIG. 21. The modified viral particle has a lower lipid content in the envelope, displays modified proteins, reduced infectivity and is immunogenic. Several embodiments of the delipidation methods provided herein do not lead to destruction of the viral envelope of the modified, partially delipidated immunogenic viral particles. A significant proportion of the viral envelopes are present following the partial delipidation. Thus, some embodiments of the partial delipidation methods provided herein result in partially delipidated particles comprising viral envelopes, including envelope proteins.

Modified Viral Particle Resulting from Removal of Lipid from Lipid-Containing Organisms Methods of the present invention solve numerous problems encountered with prior art methods. By substantially removing the lipid envelope of the virus, and keeping the viral particle intact, the method of the present invention exposes additional antigens. The host immune system recognizes the viral particle as foreign. Using the method of the present invention, what is created is a modified viral particle in which the antigenic core remains intact, thereby using the epitopes of the actual viral particle to initiate a positive immunogenic response in the patient into which it is reintroduced. In addition, the method of the present invention reduces the deleterious effect on the other plasma proteins, measured by protein recovery, such that the plasma can be reintroduced into the patient.

In creating this modified viral particle what is also created is a patient-specific antigen that induces protection against the viral particle in the species in which it is introduced. The method of the present invention creates an effective means to immunize individuals against viral pathogen infection and elicit a broad, biologically active protective immune response without risk of infecting the individual. New vaccines may be developed from certain lipid containing viruses by removing the lipid envelope and exposing antigens hidden beneath the envelope, in turn generating a positive immune response.

These "autologous vaccines" can be created by the partial removal of the lipid envelope using suitable solvent systems (one which would not damage the antigens contained in the particle) exposing antigens and/or forcing a structural modification in the viral protein structures, which when introduced into the body, would provoke an effective immune response. Non-autologous vaccines are also created in the present invention which are administered to patients that are different from the source of the virus to be delipidated. Combination vaccines directed against multiple viruses are also within the scope of the present invention. Such combination vaccines may be made from various biological fluids, from stock supplies of multiple viruses (e.g., HIV, hepatitis and SARS) and/or from multiple strains or clades of a virus (e.g., HIV-1 and HIV-2).

Modified, partially delipidated viral particles obtained with some embodiments of the methods disclosed herein represent, in some aspects, new therapeutic vaccine compositions for therapeutic immunization and induction of an immune response in animals or humans. In one aspect, modified, partially delipidated viral particles obtained with the methods disclosed herein are useful for therapeutic immunization and induction of an immune response in animals or humans infected by immunodeficiency viruses. In one embodiment of the present invention, administration of the modified, partially delipidated viral particles and compositions comprising such particles provides a new method of treatment, alleviation, or attenuation of immunodeficiency virus infections, conditions or clinical symptoms associated with these infections.

Partially delipidated immunodeficiency viral particles obtained according to some of aspects of the present invention possess at least some structural characteristics that distinguish them from the conventional delipidated viruses. Such characteristics include, but are not limited to, the content of viral proteins, including viral envelope proteins or host viral membrane associated proteins, the cholesterol content of the partially delipidated viral particles, or the ratio of cholesterol content to viral protein. For example, a partially delipidated immunodeficiency viral particle according to some embodiments of the present invention has a lower cholesterol content than the cholesterol content of the non-delipidated immunodeficiency viral particle. In one embodiment, the lower cholesterol content of the partially delipidated immunodeficiency viral particle can be at least 20% to 30% lower than the cholesterol content of the non-delipidated immunodeficiency viral particle. In other embodiments, the cholesterol content in the modified, partially delipidated viral particle is reduced, for example, no more than 80%, 60%, 56%, or 50% as compared to the unmodified viral particle. According to other embodiments, the modified, partially delipidated immunodeficiency viral particle has a ratio of μg of cholesterol relative to μg of total protein of at least 0.06. Modified, partially delipidated viral particles can also be characterized, for example, as retaining >70-95% of the host proteins, such as MHC-I, CD63, CD59 or gp41.

Infectious Organisms Treated with the Present Invention

Viruses are the preferred infectious organism treated with the method of the present invention. Viral infectious organisms which may be delipidated by the present invention to form modified viral particles include, but are not limited to the lipid-containing viruses of the following genuses: Alphavirus (alphaviruses), Rubivurus(rubella virus), Flavivirus(Flaviviruses), Pestivirus (mucosal disease viruses), (unnamed, hepatitis C virus), Coronavirus, (Coronaviruses) severe acute respiratory syndrome (SARS), Torovirus, (toroviruses), Arteivirus, (arteriviruses), Paramyxovirus, (Paramyxoviruses), Rubulavirus(rubulavriuses), Morbillivirus(morbillivuruses), Pneumoviridae(the pneumoviruses), Pneumovirus (pneumoviruses), Vesiculovirus(vesiculoviruses), Lyssavirus (lyssaviruses), Ephemerovirus(ephemeroviruses), Cytorhabdovirus (plant rhabdovirus group A), Nucleorhabdovirus (plant rhabdovirus group B), Filovirus(filoviruses), Influenzavirus A, B (influenza A and B viruses), Influenza virus C (influenza C virus), (unnamed, Thogoto-like viruses), Bunyavirus (bunyaviruses), Phlebovirus(phleboviruses), Nairovirus(nairoviruses), Hantavirus(hantaviruses), Tospovirus(tospoviruses), Arenavirus(arenaviruses), unnamed mammalian type B retroviruses, unnamed, mammalian and reptilian type C retroviruses, unnamed, type D retroviruses, Lentivirus(lentiviruses), Spumavirus(spumaviruses), Orthohepadnavirus(hepadnaviruses of mammals), Avihepadnavirus(hepadnaviruses of birds), Simplexvirus (simplexviruses), Varicellovirus(varicelloviruses), Betaherpesvirinae(the cytomegaloviruses), Cytomegalovirus(cytomegaloviruses), Muromegalovirus(murine cytomegaloviruses), Roseolovirus(human herpes virus 6, 7, 8), Gammaherpesvirinae(the lymphocyte-associated herpes viruses), Lymphocryptovirus(Epstein-Barr-like viruses), Rhadinovirus(saimiriateles-like herpes viruses), Orthopoxvirus(orthopox viruses), Parapoxvirus (parapoxviruses), Avipoxvirus(fowlpox viruses), Capripoxvirus(sheeppox-like viruses), Leporipoxvirus(myxomaviruses), Suipoxvirus(swine-pox viruses), Molluscipoxvirus(molluscum contagiosum viruses), Yatapoxyvirus(yabapox and tanapox viruses), Unnamed, African swine fever-like viruses, Iridovirus(small iridescent insect viruses), Ranavirus(front iridoviruses), Lymphocystivirus (lymphocystis viruses of fish), Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxyviridae, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses, California encephalitis virus, St. Louis encephalitis virus, sand fly fever virus, human coronaviruses 229-E and OC43 and others causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, Arenavirus: lymphocytic choriomeningitis (LCM) virus; Lassa virus, human immunodeficiency viruses 1 and 2, or any other immunodeficiency virus, hepatitis B virus, hepatitis C virus, hepatitis G virus, Subfamily: human herpes viruses 1 and 2, herpes virus B, Epstein-Barr virus), (smallpox) virus, cowpox virus, monkeypox virus, molluscum contagiosum virus, yellow fever virus, poliovirus, Norwalk virus, orf virus, and any other lipid-containing virus.

Methods of Manufacture of the Modified Viral Particle

One of ordinary skill in the art would appreciate that there may be multiple delipidation processes employed under the scope of this invention. In a preferred embodiment, a solvent system together with applied energy, for example a mechanical mixing system, is used to substantially delipidate the viral particle. The delipidation process is dependent upon the total amount of solvent and energy input into a system. Various solvent levels and mixing methods, as described below, may be used depending upon the overall framework of the process. Although a single solvent or multiple solvents may be used for delipidation of virus, it is to be understood that a single solvent is preferred since there is less probability of destroying and denaturing the viral particle.

Exemplary Solvent Systems for Use in Removal of Lipid from Viruses and Effective in Maintaining Integrity of the Viral Particle The solvent or combinations of solvents to be employed in the process of partially or completely delipidating lipid-containing organisms may be any solvent or combination thereof effective in solubilizing lipids in the viral envelope while retaining the structural integrity of the modified viral particle, which can be measured, in one embodiment, via protein recovery. A delipidation process falling within the scope of the present invention uses an optimal combination of energy input and solvent to delipidate the viral particle, while still keeping it intact. Suitable solvents comprise hydrocarbons, ethers, alcohols, phenols, esters, halohydrocarbons, halocarbons, amines, and mixtures thereof. Aromatic, aliphatic, or alicyclic hydrocarbons may also be used. Other suitable solvents, which may be used with the present invention, include amines and mixtures of amines. One solvent system is DIPE, either concentrated or diluted in water or a buffer such as a physiologically acceptable buffer. One solvent combination comprises alcohols and ethers. Another solvent comprises ether or combinations of ethers, either in the form of symmetrical ethers, asymmetrical ethers or halogenated ethers.

The optimal solvent systems are those that accomplish two objectives: first, at least partially delipidating the infectious organism or viral particle and second, employing a set of conditions such that there are few or no deleterious effects on the other plasma proteins. In addition, the solvent system should maintain the integrity of the viral particle such that it can be used to initiate an immune response in the patient. It should therefore be noted that certain solvents, solvent combinations, and solvent concentrations may be too harsh to use in the present invention because they result in a chemical kill.

It is preferred that the solvent or combination of solvents has a relatively low boiling point to facilitate removal through a vacuum and possibly heat without destroying the antigenic core of the viral particle. It is also preferred that the solvent or combination of solvents be employed at a low temperature because heat has deleterious effects on the proteins contained in biological fluids such as plasma. It is also preferred that the solvent or combination of solvents at least partially delipidate the viral particle.

Liquid hydrocarbons dissolve compounds of low polarity such as the lipids found in the viral envelopes of the infectious organisms. Particularly effective in disrupting the lipid membrane of a viral particle are hydrocarbons which are substantially water immiscible and liquid at about 37° C. Suitable hydrocarbons include, but are not limited to the following: $C_5$ to $C_{20}$ aliphatic hydrocarbons such as petroleum ether, hexane, heptane, octane; haloaliphatic hydrocarbons such as chloroform, 1,1,2-trichloro-1,2,2-trifluoroethane, 1,1,1-trichloroethane, trichloroethylene, tetrachloroethylene, dichloromethane and carbon tetrachloride; thioaliphatic hydrocarbons each of which may be linear, branched or cyclic, saturated or unsaturated; aromatic hydrocarbons such as benzene; ketones; alkylarenes such as toluene; haloarenes; haloalkylarenes; and thioarenes. Other suitable solvents may also include saturated or unsaturated heterocyclic compounds such as pyridine and aliphatic, thio- or halo- derivatives thereof.

Suitable esters for use in the present invention include, but are not limited to, ethyl acetate, propylacetate, butylacetate and ethylpropionate. Suitable detergents/surfactants that may be used include but are not limited to the following: sulfates, sulfonates, phosphates (including phospholipids), carboxylates, and sulfosuccinates. Some anionic amphiphilic materials useful with the present invention include but are not limited to the following: sodium dodecyl sulfate (SDS), sodium decyl sulfate, bis-(2-ethylhexyl) sodium sulfosuccinate (AOT), cholesterol sulfate and sodium laurate.

Solvents may be removed from delipidated viral mixtures through the use of additional solvents. For example, demulsifying agents such as ethers may be used to remove a first solvent such as an alcohol from an emulsion. Removal of solvents may also be accomplished through other methods, which do not employ additional solvents, including but not limited to the use of charcoal. Charcoal may be used in a slurry or alternatively, in a column to which a mixture is applied. Charcoal is a preferred method of removing solvents. Pervaporation may also be employed to remove one or more solvents from delipidated viral mixtures.

Examples of suitable amines for use in removal of lipid from lipid-containing organisms in the present invention are those which are substantially immiscible in water. Typical amines are aliphatic amines—those having a carbon chain of at least 6 carbon atoms. A non-limiting example of such an amine is $C_6H_{13}NH_2$.

Ether is a preferred solvent for use in the method of the present invention. Particularly preferred are the $C_4$-$C_8$ containing-ethers, including but not limited to ethyl ether, diethyl ether, and propyl ethers (including but not limited to di-isopropyl ether). Asymmetrical ethers may also be employed. Halogenated symmetrical and asymmetrical ethers may also be employed.

Low concentrations of solvents, such as ethers, may be employed to remove lipids when used alone and not in combination with other solvents. For example, a low concentration range of solvents, such as ethers include, includes but is not limited to 0.5% to 30%, 0.01% to 10%, 0.01% to 5%, 0.1% to 5%, 0.01% to 2%, or 0.1% to 2% Specific concentrations of solvents, such as ethers, that may be employed include, but are not limited to the following: 0.1%, 0.625%, 1.0% 1.25%, 2%, 2.5%, 5.0% and 10% or higher. It has been observed that dilute solutions of solvents, such as ethers, are effective. Such solutions may be aqueous solutions or solutions in aqueous buffers, such as phosphate buffered saline (PBS). Other physiological buffers may be used, including but not limited to bicarbonate, citrate, Tris, Tris/EDTA, and Trizma. Preferred ethers are diisopropyl ether (DIPE) and diethyl ether (DEE). Low concentrations of ethers may also be used in combination with alcohols, for example, n-butanol.

When used in the present invention, appropriate alcohols are those which are not appreciably miscible with plasma or other biological fluids. Such alcohols include, but are not limited to, straight chain and branched chain alcohols, including pentanols, hexanols, heptanols, octanols and those alcohols containing higher numbers of carbons.

When alcohols are used in combination with another solvent, for example, an ether, a hydrocarbon, an amine, or a combination thereof, $C_1$-$C_8$ containing alcohols may be used. Alcohols for use in combination with another solvent include $C_4$-$C_8$ containing alcohols. Accordingly, alcohols that fall within the scope of the present invention are butanols, pentanols, hexanols, heptanols and octanols, and iso forms thereof, in particular, $C_4$ alcohols or butanols (1-butanol and 2-butanol). The specific alcohol choice is dependent on the second solvent employed.

Ethers and alcohols can be used in combination as a first solvent for treating the fluid containing the lipid-containing virus, or viral particle. Any combination of alcohol and ether may be used provided the combination is effective to at least partially remove lipid from the infectious organism, without having deleterious effects on the plasma proteins. In one embodiment, lipid is removed from the viral envelope of the infectious organism. When alcohols and ether are combined as a first solvent for treating the infectious organism contained in a fluid, ratios of alcohol to ether in this solvent range from about 0.01 parts alcohol to 99.99 parts ether to 60 parts alcohol to 40 parts ether, with a specific ratio range of about 10 parts alcohol to 90 parts ether to 5 parts alcohol to 95 parts ether, with a specific ratio range of about 10 parts alcohol to 90 parts ether to 50 parts alcohol to 50 parts ether, with a specific ratio range of about 20 parts alcohol to 80 parts ether to 45 parts alcohol to 55 parts ether, with a specific range of about 25 parts alcohol to 75 parts ether.

One combination of alcohol and ether is the combination of butanol and di-isopropyl ether (DIPE). When butanol and DIPE are combined as a first solvent for treating the infectious organism contained in a fluid, ratios of butanol to DIPE in this solvent are about 0.01 parts butanol to 99.99 parts DIPE to 60 parts butanol to 40 parts DIPE, with a specific ratio range of about 10 parts butanol to 90 parts DIPE to 5 parts butanol to 95 parts DIPE, with a specific ratio range of about 10 parts butanol to 90 parts DIPE to 50 parts butanol to 50 parts DIPE, with a specific ratio range of about 20 parts butanol to 80 parts DIPE to 45 parts butanol to 55 parts DIPE, with a specific range of about 25 parts butanol to 75 parts DIPE.

Another combination of alcohol and ether is the combination of butanol with diethyl ether (DEE). When butanol is used in combination with DEE as a first solvent, ratios of butanol to DEE are about 0.01 parts butanol to 99.99 parts DEE to 60 parts butanol to 40 parts DEE, with a specific ratio range of about 10 parts butanol to 90 parts DEE to 5 parts butanol to 95 parts DEE with a specific ratio range of about 10 parts butanol to 90 parts DEE to 50 parts butanol to 50 parts DEE, with a specific ratio range of about 20 parts butanol to 80 parts DEE to 45 parts butanol to 55 parts DEE, with a specific range of about 40 parts butanol to 60 parts DEE. This combination of about 40% butanol and about 60% DEE (vol:vol) has been shown to have no significant effect on a variety of biochemical and hematological blood parameters, as shown for example in U.S. Pat. No. 4,895,558.

Biological Fluids and Treatment Thereof for Reducing Infectivity of Infectious, Lipid-Containing Organisms As stated above, various biological fluids may be treated with the method of the present invention in order to reduce the levels of infectivity of the lipid-containing organism in the biological fluid and to create modified viral particles. In a preferred embodiment, plasma obtained from an animal or human is treated with the method of the present invention in order to reduce the concentration and/or infectivity of lipid-containing infectious organisms within the plasma and to create modified viral particles. In this embodiment, plasma may be obtained from an animal or human patient by withdrawing blood from the patient using well-known methods and treating the blood in order to separate the cellular components of the blood (red and white cells) from the plasma. Such methods for treating the blood are known to one of ordinary skill in the art and include but are not limited to centrifugation and filtration. One of ordinary skill in the art understands the proper centrifugation conditions for separating such lipid-containing organisms from the red and white cells. Use of the present invention permits treatment of lipid-containing organisms, for example those found within plasma, without having deleterious effects on other plasma proteins and maintaining the integrity of the viral core.

Viruses in the plasma are affected by the treatment of the plasma with the method of the present invention. The lipid-containing viral organism may be separated from the red and white cells using techniques known to one of ordinary skill in the art.

Biological fluids include stocks of viral preparations including various strains of viruses as well as different types of viruses. Treatment of such biological fluids with the method of the present invention produces modified viral particles that may be administered to a patient as a non-autologous vaccine. Such non-autologous vaccines provide protection in the patient against more than strain of a virus and/or against more than one type of virus. Treatment of lipid-containing organisms may occur in biological fluids other than blood and plasma. For example, peritoneal fluid may be treated with the present invention to affect the levels and infectivity of lipid-containing organisms without deleterious effects on protein components. The treated fluid may subsequently be reintroduced into the animal or human from which it was obtained. Treatment of non-blood types of fluids affects the lipid-containing organisms in the fluid, such as the virus.

Once a biological fluid, such as plasma, is obtained either in this manner, or for example, from a storage facility housing bags of plasma, the plasma is contacted with a first organic solvent, as described above, capable of solubilizing lipid in the lipid-containing infectious organism. The first organic solvent is combined with the plasma in a ratio wherein the first solvent is present in an amount effective to substantially solubilize the lipid in the infectious organism, for example, dissolve the lipid envelope that surrounds the virus. Exemplary ratios of first solvent to plasma (expressed as a ratio of first organic solvent to plasma) are described in the following ranges: 0.5-4.0:0.5-4.0; 0.8-3.0:0.8-3.0; and 1-2:0.8-1.5. Various other ratios may be applied, depending on the nature of the biological fluid. For example, in the case of cell culture fluid, the following ranges may be employed of first organic solvent to cell culture fluid: 0.5-4.0:0.5-4.0; 0.8-3.0:0.8-3.0; and 1-2:0.8-1.5.

After contacting the fluid containing the infectious organism with the first solvent as described above, the first solvent and fluid are mixed, using methods including but not limited to one of the following suitable mixing methods: gentle stirring; vigorous stirring; vortexing; swirling; homogenization; and, end-over-end rotation.

The amount of time required for adequate mixing of the first solvent with the fluid is related to the mixing method employed. Fluids are mixed for a period of time sufficient to permit intimate contact between the organic and aqueous phases, and for the first solvent to at least partially or completely solubilize the lipid contained in the infectious organism. Typically, mixing will occur for a period of about 10 seconds to about 24 hours, possibly about 10 seconds to about 2 hours, possibly approximately 10 seconds to approximately 10 minutes, or possibly about 30 seconds to about 1 hour, depending on the mixing durations method employed. Non-limiting examples of mixing durations associated with different methods include 1) gentle stirring and end-over-end rotation for a period of about 10 seconds to about 24 hours, 2) vigorous stirring and vortexing for a period of about 10 seconds to about 30 minutes, 3) swirling for a period of about 10 seconds to about 2 hours, or 4) homogenization for a period of about 10 seconds to about 10 minutes.

Separation of Solvents

After mixing of the first solvent with the fluid, the solvent is separated from the fluid being treated. The organic and aqueous phases may be separated by any suitable manner known to one of ordinary skill in the art. Since the first solvent is typically immiscible in the aqueous fluid, the two layers are permitted to separate and the undesired layer is removed. The undesired layer is the solvent layer containing dissolved lipids and its identification, as known to one of ordinary skill in the art, depends on whether the solvent is more or less dense than the aqueous phase. An advantage of separation in this manner is that dissolved lipids in the solvent layer may be removed.

In addition, separation may be achieved through means, including but not limited to the following: removing the undesired layer via pipetting; centrifugation followed by removal of the layer to be separated; creating a path or hole in the bottom of the tube containing the layers and permitting the lower layer to pass through; utilization of a container with valves or ports located at specific lengths along the long axis of the container to facilitate access to and removal of specific layers; and any other means known to one of ordinary skill in the art. Another method of separating the layers, especially when the solvent layer is volatile, is through distillation under reduced pressure or evaporation at room temperature, optionally combined with mild heating. In one embodiment employing centrifugation, relatively low g forces are employed, such as 900×g for about 5 to 15 minutes to separate the phases.

A preferred method of removing solvent is through the use of charcoal, preferably activated charcoal. This charcoal is optionally contained in a column. Alternatively the charcoal may be used in slurry form. Various biocompatible forms of charcoal may be used in these columns. Pervaporation methods and use of charcoal to remove solvents are preferred methods for removing solvent.

Following separation of the first solvent from the treated fluid, some of the first solvent may remain entrapped in the aqueous layer as an emulsion. A preferred method of removing a first solvent or a demulsifying agent is through the use of adsorbants, such as charcoal. The charcoal is preferably activated charcoal. This charcoal is optionally contained in a column, as described above. Still another method of removing solvent is the use of hollow fiber contactors. Pervaporation methods and charcoal adsorbant methods of removing solvents are preferred. In yet another embodiment, a de-emulsifying agent is employed to facilitate removal of the trapped first solvent. The de-emulsifying agent may be any agent effective to facilitate removal of the first solvent. A preferred de-emulsifying agent is ether and a more preferred de-emulsifying agent is diethyl ether. The de-emulsifying agent may be added to the fluid or in the alternative the fluid may be dispersed in the de-emulsifying agent. In vaccine preparation, alkanes in a ratio of about 0.5 to 4.0 to about 1 part of emulsion (vol:vol) may be employed as a de-emulsifying agent, followed by washing to remove the residual alkane from the remaining delipidated organism used for preparing the vaccine. Preferred alkanes include, but are not limited to, pentane, hexane and higher order straight and branched chain alkanes.

The de-emulsifying agent, such as ether, may be removed through means known to one of skill in the art, including such means as described in the previous paragraph. One convenient method to remove the de-emulsifying agent, such as ether, from the system, is to permit the ether to evaporate from the system in a running fume hood or other suitable device for collecting and removing the de-emulsifying agent from the environment. In addition, de-emulsifying agents may be removed through application of higher temperatures, for example from about 24 to 37° C. with or without pressures of about 10 to 20 mbar. Another method to remove the de-emulsifying agent involves separation by centrifugation, followed by removal of organic solvent through aspiration, further followed by evaporation under reduced pressure (for example 50 mbar) or further supply of an inert gas, such as nitrogen, over the meniscus to aid in evaporation.

Methods of Treating Biological Fluids (Delipidation)

It is to be understood that the method of the present invention may be employed in either a continuous or discontinuous manner. That is, in a continuous manner, a fluid may be fed to a system employing a first solvent which is then mixed with the fluid, separated, and optionally further removed through application of a de-emulsifying agent. The continuous method also facilitates subsequent return of the fluid containing delipidated infectious organism to a desired location. Such locations may be containers for receipt and/or storage of such treated fluid, and may also include the vascular system of a human or animal or some other body compartment of a human or animal, such as the pleural, pericardial, peritoneal, and abdominopelvic spaces.

In one embodiment of the continuous method of the present invention, a biological fluid, for example, blood, is removed from an animal or a human through means known to one of ordinary skill in the art, such as a catheter. Appropriate anti-clotting factors as known to one of ordinary skill in the art are employed, such as heparin, ethylenediaminetetraacetic acid (EDTA) or citrate. This blood is then separated into its cellular and plasma components through the use of a centrifuge. The plasma is then contacted with the first solvent and mixed with the first solvent to effectuate lipid removal from the infectious organism contained within the plasma. Following separation of the first solvent from the treated plasma, charcoal, pervaporation or a de-emulsifying agent is optionally employed to remove entrapped first solvent. After ensuring that acceptable levels (non-toxic) of first solvent or de-emulsifying agent, if employed, are found within the plasma containing the delipidated infectious organism, the plasma is then optionally combined with the cells previously separated from the blood to form a new blood sample containing at least partially delipidated viral particles, also called modified viral particles herein.

Through the practice of this method, the infectivity of the infectious organism is greatly reduced or eliminated. Following recombination with the cells originally separated from the blood, the fluid with reduced lipid levels and containing virus with reduced lipid levels may be reintroduced into either the vascular system or some other system of the human or animal. The effect of such treatment of plasma removed from the human or animal and return of the sample containing the partially or completely delipidated infectious organism, or modified viral particle, to the human or animal causes a net decrease in the infectivity of the infectious organism contained within the vascular system of the human or animal. The modified viral particle also serves to initiate an autologous immune response in the patient when administered to the patient. In this mode of operation, the method of the present invention is employed to treat body fluids in a continuous manner—while the human or animal is connected to an extracorporeal device for such treatment.

In yet another embodiment, the discontinuous or batch mode, the human or animal is not connected to an extracorporeal device for processing bodily fluids with the method of the present invention. In a discontinuous mode of operation, the present invention employs a fluid previously obtained from a human or animal, which may include, but is not limited to plasma, lymphatic fluid, or follicular fluid. The fluid may be contained within a blood bank or in the alternative, drawn from a human or animal prior to application of the method. The fluid may be a reproductive fluid or any fluid used in the process of artificial insemination or in vitro fertilization. The fluid may also be one not directly obtained from a human or animal but rather any fluid containing a potentially infectious organism, such as cell culture fluid. Stocks of various strains or clades of a virus and also stocks of multiple viruses may be used in the present method to produce vaccines. In this mode of operation, this fluid is treated with the method of the present invention to produce a new fluid with reduced lipid levels which contains at least partially or completely delipidated infectious organisms, or modified viral particles. One embodiment of this mode of the present invention is to treat plasma samples previously obtained from other animals or humans and stored in a blood bank for subsequent transfusion. This is a non-autologous method of providing vaccine protection. These samples may be treated with the method of the present invention to treat or prevent one or more infectious disease, such as HIV, hepatitis, and/or cytomegalovirus, from the biological sample.

Delipidation of an infectious organism can be achieved by various means. A batch method can be used for fresh or stored biological fluids, for example, fresh frozen plasma. In this case a variety of the described organic solvents or mixtures thereof can be used for viral inactivation. Extraction time depends on the solvent or mixture thereof and the mixing procedure employed.

Through the use of the methods of the present invention, levels of lipid in lipid-containing viruses in a fluid are reduced, and the fluid, for example, delipidated plasma containing the modified viral particles may be administered to the patient. Such fluid contains modified viral particles with reduced infectivity, act as a vaccine and provide protection in the patient against the virus or provide a treatment in an infected patient by generating an immune response and decreasing the severity of the disease. These modified viral particles induce an immune response in the recipient to exposed epitopes on the modified viral particles. Alternatively the modified viral particles may be combined with a pharmaceutically acceptable carrier, and optionally an adjuvant, and administered as a vaccine composition to a human or an animal to induce an immune response in the recipient.

Vaccine Production

In one embodiment, the modified viral particle, which is at least partially or substantially delipidated and has immunogenic properties, is optionally combined with a pharmaceutically acceptable carrier to make a composition comprising a vaccine. In a preferred embodiment, the modified viral particle is retained in the biological fluid, such as plasma, with reduced lipid levels and is administered to a patient as a vaccine. This vaccine composition is optionally combined with an adjuvant or an immunostimulant and administered to an animal or a human. Both autologous and non-autologous vaccines, including combination vaccines, are within the scope of the present invention. It is to be understood that vaccine compositions may contain more than one type of modified viral particle or component thereof, in order to provide protection against more than one strain of a virus or more than one viral disease after vaccination. Such combinations may be selected according to the desired immunity. For example, preferred combinations include, but are not limited to HIV and hepatitis or influenza and hepatitis. More specifically, the vaccine can comprise a plurality of modified viral particles having patient-specific antigens and modified viral particles having non-patient specific antigens or stock viral particles that have undergone the delipidation process of the present invention. The remaining modified viral particles of the organism are retained in the delipidated biological fluid, and when reintroduced into the animal or human, are presumably ingested by phagocytes and generate an immune response.

Administration of Vaccine Produced With the Method of the Present Invention

When a delipidated infectious organism, for example one in the form of a modified viral particle with exposed antigenic determinants, is administered to an animal or a human, it is optionally combined with a pharmaceutically acceptable carrier to produce a vaccine, and optionally combined with an adjuvant or an immunostimulant as known to one of ordinary skill in the art. The vaccine formulations may conveniently be presented in unit dosage form and may be prepared by conventional pharmaceutical techniques known to one of ordinary skill in the art. Such techniques include uniformly and intimately bringing into association the active ingredient and the liquid carriers (pharmaceutical carrier(s) or excipient(s)). Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers—for example, sealed ampules and vials—and may be stored in a freeze-dried (lyophilized) condition requiring only the addition of the sterile liquid carrier, for example, water for injections, immediately prior to use. The vaccine may be stored at temperatures of from about 4° C. to −100° C. The vaccine may also be stored in a lyophilized state at different temperatures including room temperature. Extemporaneous injection solutions and suspensions may be prepared from sterile powders, granules and tablets commonly used by one of ordinary skill in the art. The vaccine may be sterilized through conventional means known to one of ordinary skill in the art. Such means include, but are not limited to filtration, radiation and heat. The vaccine of the present invention may also be combined with bacteriostatic agents, such as thimerosal, to inhibit bacterial growth.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, intravenous, intraperitoneal, and topical. The vaccine may also be administered in the vicinity of lymphatic tissue, for example through administration to the lymph nodes such as axillary, inguinal or cervical lymph nodes.

The vaccine of the present invention may be administered in different forms, including but not limited to solutions, emulsions and suspensions, microspheres, particles, microparticles, nanoparticles, and liposomes. It is expected that from about 1 to 5 dosages may be required per immunization regimen. One of ordinary skill in the medical or veterinary arts of administering vaccines will be familiar with the amount of vaccine to be administered in an initial injection and in booster injections, if required, taking into consideration, for example, the age and size of a patient. Initial injections may range from about less than 1 ng to 1 gram based on total viral protein. A non-limiting range may be 1 ml to 10 ml. The volume of administration may vary depending on the administration route.

Vaccination Schedule

The vaccines of the present invention may be administered before, during or after an infection. The vaccine of the present invention may be administered to either humans or animals. In one embodiment, the viral load (one or more viruses) of a human or an animal may be reduced by delipidation treatment of the plasma. The same individual may receive a vaccine directed to the one or more viruses, thereby stimulating the immune system to combat against the virus that remains in the individual. The time for administration of the vaccine before initial infection is known to one of ordinary skill in the art. However, the vaccine may also be administered after initial infection to ameliorate disease progression or to treat the disease.

Adjuvants

A variety of adjuvants known to one of ordinary skill in the art may be administered in conjunction with the modified viral particles in the vaccine composition. Such adjuvants include, but are not limited to the following: polymers, co-polymers such as polyoxyethylene-polyoxypropylene co-polymers, including block co-polymers; polymer P1005; monotide ISA72; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; water-in-oil mixtures, water-in-oil-in-water mixtures or combinations thereof.

Suspending Fluids and Carriers

A variety of suspending fluids or carriers known to one of ordinary skill in the art may be employed to suspend the vaccine composition. Such fluids include without limitation: sterile water, saline, buffer, or complex fluids derived from growth medium or other biological fluids. Preservatives, stabilizers and antibiotics known to one of ordinary skill in the art may be employed in the vaccine composition.

The following experimental examples are illustrative in showing that a delipidation process of the viral particle occurred and in particular, that the viral particle was modified and noted to exhibit a positive immunogenic response in the species from which it was derived. It will be appreciated that other embodiments and uses will be apparent to those skilled in the art and that the invention is not limited to these specific illustrative examples or preferred embodiments.

EXAMPLE 1

A. Delipidation of Serum Produces Duck Hepatitis B virus (DHBV) Having Reduced Infectivity A standard duck serum pool (Camden) containing $10^6$ $ID_{50}$ doses of DHBV was used. $ID_{50}$ is known to one of ordinary skill in the art as the infective dosage (ID) effective to infect 50% of animals treated with the dose. Twenty-one ducklings were obtained from a DHBV negative flock on day of hatch. These ducklings were tested at purchase and shown to be DHBV DNA negative by dot-blot hybridization.

The organic solvent system was mixed in the ratio of 40 parts butanol to 60 parts diisopropyl ether. The mixed organic solvent system (4 ml) was mixed with the standard serum pool (2 ml) and gently rotated for 1 hour at room temperature. The mixture was centrifuged at 400×g for 10 minutes and the lower aqueous phase (containing the plasma) removed at room temperature. The aqueous phase was then mixed with an equal volume of diethyl ether and centrifuged as before to remove any remaining lipid/solvent mixture. The aqueous phase was again removed and mixed with an equal volume of diethyl ether and re-centrifuged. The aqueous phase was removed and any residual diethyl ether was removed by airing in a fume cabinet at room temperature for about 1 hour. The delipidated plasma, with or without viral particles was stored at −20° C.

The positive and negative control duck sera were diluted in phosphate buffered saline (PBS). Positive controls: 2 ml of pooled serum containing $10^6 ID_{50}$ doses of DHBV was mixed with 4 ml of PBS. Negative controls: 2 ml of pooled DHBV negative serum was mixed with 4 ml of PBS. Residual infectivity was tested by inoculation of 100 μl of either test sample (n=7), negative (n=7) or positive (n=7) controls into the peritoneal cavities of day-old ducks. Controls were run with DHBV negative serum treated with organic solvents and subsequently mixed with PBS and injected into recipient ducks.

One of the positive control ducks died between 4 and 6 days of age and was excluded from further analysis. A further 3 positive control ducks died between 9 and 10 days of age, and two treatment and one negative control died on day 11. It was decided to terminate the experiment. The remaining ducklings were euthanized on day 12 with sodium pentibarbitone, i.v., and their livers removed for DHBV DNA analysis as described by Deva et al (*J. Hospital Infection* 33:119-130, 1996). All seven negative control ducks remained DHBV negative. Livers of all six positive control ducks were DHBV positive. All seven test ducks remained negative for DHBV DNA in their liver.

Delipidation of serum using the above solvent system resulted in DHBV having reduced infectivity. None of the ducklings receiving treated serum became infected. Although the experiment had to be terminated on day 12 instead of day 14, the remaining positive control ducks were positive for DHBV (3/3 were DHBV positive by day 10). This suggests that sufficient time had elapsed for the treated ducks to become DHBV positive in the liver and that the premature ending of the experiment had no bearing on the results.

B. Delipidated DHBV Positive Serum as a Vaccine to Prevent DHBV Infection

The efficacy of the delipidation procedure to provide a patient specific "autologous" vaccine against Duck Hepatitis B Virus (DHBV) was examined. Approximately 16 Pekin cross ducklings were obtained from a DHBV negative flock of ducklings on the day of hatch. The ducklings were tested and determined to be DHBV negative by analysis of DHBV DNA using dot-blot hybridization. The ducks were divided into the following three groups:

TABLE 1

| | # of Ducks | Vaccine Administered | Results |
|---|---|---|---|
| GROUP 1 | 6 | Test Vaccine | 5/6 ducks remained DHBV negative following challenge |

TABLE 1-continued

| | # of Ducks | Vaccine Administered | Results |
|---|---|---|---|
| GROUP 2 | 4 | Sham Vaccine [Glutaraldehyde-inactivated DHBV (chemical kill)] | 4/4 ducks became DHBV positive following challenge. |
| GROUP 3 (Control) | 6 | Mock Vaccine [Phosphate Buffered Saline (PBS)] | 6/6 ducks became DHBV positive following challenge. |

1. Glutaraldehyde Inactivation

Glutaraldehyde inactivation was achieved as known by those of ordinary skill in the art by fixation with a dilute solution of glutaraldehyde at about 1:250. Glutaraldehyde is a well known cross linking agent.

2. Delipidation Procedure

An organic solvent system was employed to perform delipidation of serum. The solvent system consisted of 40% butanol (analytical reagent grade) and 60% diisopropyl ether and was mixed with the serum in a 2:1 ratio. Accordingly, 4 ml of the organic solvent was mixed with 2 ml of the serum and rotated for 1 hour. This mixture was centrifuged at approximately 400×g for 10 minutes followed by removal of the aqueous phase. The aqueous phase was then mixed with an equal volume of diethyl ether and centrifuged at 400×g for 10 minutes. Next, the aqueous phase was removed and mixed with an equal volume of diethyl ether and rotated end-over-end at 30 rpm for about 1 hour, and centrifuged at 400×g for 10 minutes. The aqueous phase was removed and the residual diethyl ether was removed through evaporation in a fume cabinet for approximately 10 to 30 minutes. The treated serum remained following removal of diethyl ether and was used to produce the vaccine. The delipidation procedure control involved subjecting the DHBV negative serum to the same delipidation procedure as the DHBV positive serum.

3. Vaccine Production

TABLE 2

| Vaccine Type | First Dose (injected with 200 µl of respective vaccine into peritoneal cavity on Day 8 post-hatch) | Second Dose (injected with 300 µl of respective vaccine intramuscularly on Day 16 post-hatch) | Third Dose (injected with 300 µl of respective vaccine intramuscularly on Day 22 post-hatch) |
|---|---|---|---|
| TEST | A 40 µl aliquot of the delipidated serum was mixed with 1960 µl of phosphate buffered saline (PBS) | A 40 µl aliquot of the delipidated serum was mixed with 1960 µl of PBS and then emulsified in 1000 µl of Freund's Incomplete Adjuvant. | A 200 µl aliquot of the delipidated serum was mixed with 1800 µl of PBS and then emulsified in 1000 µl of Freund Incomplete Adjuvant. |
| SHAM (DHBV SERUM CONTROL) | A 200 µl aliquot of DHBV positive serum pool #4 (20.4.99) was mixed with 300 µl of PBS and 100 µl of a 2% glutaraldehyde solution (Aidal Plus from Whiteley Chemicals) and incubated for 10 minutes to inactivate the DHBV. A 40 µl aliquot of the inactivated serum/PBS mixture was added to 1960 µl PBS. | A 200 µl aliquot of DHBV positive serum pool #4 (20.4.99) was mixed with 300 µl of PBS and 100 µl Aidal Plus (Whiteley Chemicals) and incubated for 10 minutes to inactivate the DHBV. A 40 µl aliquot of the inactivated serum/PBS mixture was added to 1960 µl PBS and emulsified in 1000 µl Freunds Incomplete Adjuvant. | A 200 µl aliquot of DHBV positive serum pool #4 (20.4.99) was mixed with 300 µl of PBS and 100 µl Aidal Plus (Whiteley Chemical and incubated for 10 minutes to inactivate the DHBV. A 40 µl aliquot of the inactivated serum/PBS mixture was added 1960 µl PBS and emulsified in 1000 µl Freunds Incomplete Adjuvant. |
| MOCK (DHBV NEGATIVE CONTROL) | PBS | A 2000 µl aliquot of PBS was emulsified in 1000 µl Freunds Incomplete Adjuvant. | A 2000 µl aliquot of PBS was emulsified in 1000 µl Freunds Incomplete Adjuvant. |

4. Experimental Procedure

Ducks were challenged with 1000 µl of DHBV positive serum (serum pool 20.1.97) on day 29, post-hatch. Serum pool 20.1.97 was shown to have $1.8 \times 10^{10}$ genome equivalent (gev)/ml by dot-blot hybridization. One genome equivalent (gev) is approximately one viral particle. Ducks were bled prior to full vaccination on days 1 and 10, prior to challenge on days 17 and 3, and post challenge on days 37, 43 and 52. Their serum was tested for DHBV DNA by dot-blot hybridization as described by Deva et al. (1995). Ducks were euthanized on day 58 and their livers removed, the DNA extracted and tested for the presence of DHBV by dot-blot hybridization as described by Deva et al. (1995).

5. Analysis of Results
   a. Test ducks. Five of the 6 test ducks vaccinated with the test vaccine remained negative for DHBV DNA in the serum and liver following challenge. One test duck became positive for DHBV following challenge.
   b. Sham vaccinated ducks. All 4 of the ducks vaccinated with glutaraldehyde inactivated serum became DHBV positive following challenge with DHBV.
   c. Mock vaccinated ducks. All 6 of the 6 mock-vaccinated negative control ducks became DHBV positive following challenge.

The Chi-square analysis was used to compare differences between treatments. Significantly more control ducks (mock vaccinated) became DHBV positive following challenge than the ducks vaccinated with delipidated serum ($p<0.05$).

Vaccination of ducklings with delipidated DHBV positive serum using the above protocol resulted in prevention of DHBV infection following challenge with DHBV positive serum in 5 of 6 ducklings. This suggests that the delipidated serum vaccine is capable of inducing a positive immunogenic response in vaccinated ducks. It is further believed that the delipidation process exposed patient-specific antigens that were previously unexposed and/or caused a structural change in the viral particle structure to enable the positive immunogenic response. In comparison 6 of 6 mock vaccinated and 4 of 4 sham-vaccinated ducks became DHBV positive following vaccination suggesting no induction of immunity in these ducks due to lack of immune response.

EXAMPLE 2

A. Delipidation of Cattle Pestivirus (bovine viral diarrhea virus, BVDV), as a Model for Hepatitis C A standard cattle pestivirus isolate (BVDV) was used in these experiments. This isolate, "Numerella" BVD virus, was isolated in 1987 from a diagnostic specimen submitted from a typical case of 'Mucosal Disease' on a farm in the Bega district of New South Wales (NSW), Australia. This virus is non-cytopathogenic, and reacts with all 12 of a panel of monoclonal antibodies raised at the Elizabeth Macarthur Agricultural Institute (EMAI), NSW, Australia, as typing reagents. Therefore, this virus represents a 'standard strain' of Australian BVD viruses.

The Numerella virus was grown in bovine MDBK cells tested free of adventitious viral agents, including BVDV. The medium used for viral growth contained 10% adult bovine serum derived from EMAI cattle, all of which tested free of BVDV virus and BVDV antibodies. This serum supplement has been employed for years to exclude the possibility of adventitious BVDV contamination of test systems, a common failing in laboratories worldwide that do not take precautions to ensure the test virus is the only one in the culture system. Using these tested culture systems ensured high-level replication of the virus and a high yield of infectious virus. Titration of the final viral yield after 5 days growth in MDBK cells showed a titer of $10^{6.8}$ infectious viral particles per ml of clarified (centrifuged) culture medium.

1. Treating Infectious BVDV 100 ml of tissue-culture supernatant, containing $10^{6.8}$ viral particles/ml, was harvested from a 150 cm$^2$ tissue-culture flask. The supernatant was clarified by centrifugation (cell debris pelleted at 3000 rpm, 10 min, 4° C.) and 10 ml set aside as a positive control for animal inoculation (non-treated virus). The remaining 90 ml, containing $10^{7.75}$ infectious virus, was treated using the following protocol: 180 ml of a solvent mixture butanol:diisopropyl ether (DIPE) (2:1) was added to a 500 ml conical flask and mixed by swirling. The mixture was then shaken for 60 min at 30 rpm at room temperature on an orbital shaker. It was then centrifuged for 10 min at 400×g at 4° C., after which the organic solvent phase was removed and discarded. In subsequent steps, the bottom layer (aqueous phase) was removed from beneath the organic phase, improving yields considerably.

The aqueous phase, after the butanol:DIPE treatment, was washed four times with an equal volume of fresh diethyl ether (DEE) to remove all contaminating traces of butanol. After each washing, the contents of the flask was swirled to ensure even mixing of both aqueous and solvent phases before centrifugation as above (400×g, 10 min, 4° C.). After four washes, the aqueous phase was placed in a sterile beaker covered with a sterile tissue fixed to the top of the beaker with a rubber band to prevent contamination and placed in a fume hood running continuously overnight (16 hr) to remove all remaining volatile ether residue from the inactivated viral preparation. Subsequent culture of the treated material demonstrated no contamination. The treated viral preparation was then stored at 4° C. under sterile conditions until inoculation into tissue culture or animals to test for any remaining infectious virus.

2. Testing of Treated BVDV Preparation
   a. Tissue-culture Inoculation

Two milliliters of the solvent-treated virus preparation, expected to contain about $10^{7.1}$ viral equivalents, was mixed with 8 ml tissue-culture medium Minimal Eagles Medium (MEM) containing 10% tested-free adult bovine serum and adsorbed for 60 min onto a monolayer of MDBK cells in a 25 cm$^2$ tissue-culture flask. As a positive control, 2 ml of non-treated or substantially lipid-containing infectious virus (also containing about $10^{7.1}$ viral equivalents) was similarly adsorbed on MDBK cells in a 25 cm$^2$ tissue-culture flask. After 60 min, the supernatant was removed from both flasks and replaced with normal growth medium (+10% ABS). The cells were then grown for 5 days under standard conditions before the MDBK cells were fixed and stained using a standard immunoperoxidase protocol with a mixture of 6 BVDV-specific monoclonal antibodies (EMAI panel, reactive with 2 different BVD viral proteins).

There were no infected cells in the monolayer of MDBK cells that was inoculated with the organic solvent treated virus. In contrast, approximately 90% of the cells in the control flask (that was inoculated with non-inactivated BVDV) were positive for virus as shown by heavy, specific, immunoperoxidase staining. These results showed that, under in vitro testing conditions, no infectious virus remained in the treated, at least partially delipidated BVDV preparation.

b. Animal Inoculation

An even more sensitive in vivo test is to inoculate naïve (antibody negative) cattle with the at least partially delipidated virus preparation. As little as one infectious viral particle injected subcutaneously in such animals is considered to be an infectious cow dose, given that entry into cells and replication of the virus is extremely efficient for BVDV. A group of 10 antibody-negative steers (10-12 months of age) were randomly allocated to 3 groups.

The first group of 6 steers was used to test whether BVDV had reduced infectivity. The same at least partially delipidated preparation of BVDV described above was used in this example. Two steers were inoculated with a vaccine having at least partially delipidated viral particles to act as a positive control for the vaccine group. These two positive control animals were run under separate, quarantined conditions to prevent them from infecting other animals when they developed a transient viraemia after infection (normally at 4-7 days after receiving live BVDV virus). The two remaining steers acted as negative "sentinel" animals to ensure there was no naturally-occurring pestivirus transmission within the vaccinated group of animals. Antibody levels were measured in all 10 animals using a validated, competitive ELISA developed at EMAI. This test has been independently validated by CSL Ltd and is marketed by IDEXX Scandinavia in Europe.

The six animals in the first group each received a subcutaneous injection of 4.5 ml of the at least partially delipidated BVDV preparation, incorporated in a commercial adjuvant. Since each ml of the at least partially delipidated preparation contained $10^{6.8}$ viral equivalents, the total viral load before the delipidation process was $10^{7.4}$ tissue culture infectious doses $(TCID)_{50}$. The positive-control animals received 5 ml each of the non-delipidated preparation, that is, $10^{7.5}$ $TCID_{50}$ injected subcutaneously in the same way as for the first group. The remaining two 'sentinel' animals were not given any viral antigens, having been grazed with the first group of animals throughout the trial to ensure there was no natural pestivirus activity occurring in the group while the trial took place.

There was no antibody development in any of the vaccinated steers receiving the at least partially delipidated BVD virus preparation until a second dose of vaccine was given. Thus, at 2 and 4 weeks after a single dose, none of the 6 steers seroconverted showing that there was no infectious virus left in a total volume of 27 ml of the at least partially delipidated virus preparation. This is the equivalent of a total inactivation of $10^{8.2}$ $TCID_{50}$. In contrast, there were high levels of both anti-E2 antibodies (neutralizing antibodies) and anti-NS3 antibodies at both 2 and 4 weeks after inoculation in the two steers receiving 5 ml each of the viral preparation prior to delipidation. This confirmed the infectious nature of the virus prior to delipidation. These in vivo results confirm the findings of the in vitro tissue-culture test. The two 'sentinel' animals remained seronegative throughout, showing the herd remained free of natural pestivirus infections.

The panel of monoclonal antibodies used detected host antibodies directed against the major envelope glycoprotein (E2), which is a glycoprotein incorporated in the lipid envelope of the intact virus. The test systems also detected antibodies directed against the non-structural protein, NS3 that is made within cells infected by the virus. This protein has major regulatory roles in viral replication and is not present within the infectious virus. There was no evidence in the vaccinated cattle that infectious virus was present, indicating all infectious viral particles had been destroyed. All pestiviruses are RNA viruses. Therefore, there was no viral DNA present in the delipidated preparation. These results demonstrate the efficacy of the present method to at least partially delipidate virus such that substantially no infectious virus is found in animals receiving the delipidated virus.

B. Delipidated BVDV Preparation as a Vaccine in Steers

All six steers that had received an initial dose of 4.5 ml of the at least partially delipidated BVDV preparation described in above in Section A were again injected subcutaneously with a similar dose at 4 weeks after the first priming dose. At this time there were no antibody responses after the initial dose. It is normal for an animal to react after the second dose. Strong secondary immune responses for anti-E2 antibody levels (equivalent to serum neutralizing antibodies SNT) were observed in 3 of the 6 steers at 2 weeks after the second dose of the at least partially delipidated virus. This response was more than 70% inhibition in a competitive ELISA. The remaining 3 animals showed weak antibody responses (23-31% inhibition).

In contrast to the anti-E2 antibody responses, only one animal developed a strong anti-NS3 antibody response (93% inhibition) at 2 weeks after the second dose of at least partially delipidated BVDV. A second animal had a weak anti-NS3 response (29% inhibition) and four animals showed no antibody following administration of 2 doses. This was not unexpected since similar responses following administration of at least partially delipidated BVDV vaccines have been observed previously. The antibody levels in steers following 2 doses of the at least partially delipidated BVDV preparation demonstrate its potential as a vaccine since antiE2 antibody levels were measurable in all 6 vaccinated steers at 2 weeks after the second dose.

EXAMPLE 3

Use of Delipidated SIV to Induce or Augment SIV Specific Humoral and CD4+ T Cell Memory Responses in Mice—a Model for a New Auto-vaccination Strategy against Lentiviral Infection The following studies focused on the simian equivalent of human HIV, termed SIV. The purpose was to utilize delipidated SIVmac251 (an uncloned highly pathogenic isolate of SIV) to carry out studies to determine the relative immunogenicity of the delipidated virus in mice. The complete nucleotide sequence of an infectious clone of simian immunodeficiency virus of macaques, SIVmac239, has been determined. Virus produced from this molecular clone causes AIDS in rhesus monkeys in a time frame suitable for laboratory investigation. The proviral genome including both long terminal repeats is 10,279 base pairs in length and contains open reading frames for gag, pol, vif, vpr, vpx, tat, rev, and env. The nef gene contains an in-frame premature stop after the 92nd codon. At the nucleotide level, SIVmac239 is closely related to SIVmac251 (98%) and SIVmac142 (96%). (Regier D A, Desrosiers Annual Review Immunology. 1990; 8:557-78.)

Experiments were performed to determine the minimal dose of delipidated simian immunodeficiency virus (SIV) that would produce a readily recognizable boosting of the virus specific humoral and/or cellular immune response in previously primed Balb/c mice. All experiments were carried out in a BSL3 facility.

The immunogenicity of the delipidated virus preparation was compared with an aliquot of the same virus in its native form. The quality (titer of antibody, the conformational and linear epitope specificity of the antibody, the isotype content of the antibody and the function of the antibody) and quantity of antibody induced by immunization of mice with equivalent protein amounts of the non-delipidated and delipidated virus preparation were ascertained as described below. Total protein from an aliquot of wild type virus and total protein recovered following delipidation of the same aliquot of virus were determined using standard quantitative protein assay (Biorad, BCA kit assay, Rockford, Ill.). The total protein profile was determined using SDS-PAGE analysis of the wild type virus and the delipidated virus preparation and the relative epitope preservation was ascertained by Western Blot comparison of wild type with delipidated virus.

Equivalent protein amounts of the chemically treated wild type and the delipidated virus were analyzed for their ability to boost virus specific immune response in groups of mice.

The sera from these immunized mice were assayed by ELISA and Western Blot analysis for reactivity against native wild type and for comparison the delipidated virus preparation. Spleen cells were assayed for their CD4 and CD8 SIV virus env and gag specific immune response enhancing capacity as outlined below. Standard statistical analyses were performed for the analysis of the data.

Four to six week old healthy female Balb/c mice from the Jackson labs, Bar Harbor, Me. were purchased and housed in the BSL2/3 mouse housing facility at Emory University. Twenty Balb/c mice were each immunized subcutaneously with 25 ug of protein of 2-2 dithiopyridine-inactivated SIVmac251 incorporated in an equal volume of Freunds incomplete adjuvant.

A sufficient quantity of SIVmac251 was delipidated to provide the amount needed for boosting these mice per schedule. Delipidation consisted of incubating SIVmac251 with 10% DIPE in phosphate buffered saline (PBS). 1.0 ml of a 10% DIPE solution in PBS was prepared and mixed on a vortexer until it appeared cloudy.

The virus preparation: A 1 ml tube from Advanced Biotechnologies SIVmac251 was used as seed stock (Sucrose Gradient Purified Virus 1 mg/ml). The supplier reported a titer of $10^{6.7}$ with total protein of 1.074 mg/mL (Pierce BCA protein method) and virus particle count of $6.95^{10}$/ml (EM). It was confirmed that the virus had a titer of $10^{7.0}$ using CEM× 174, the first time as a rapid assay, and the second time in quadruplicate cultures/dilution. A measurement of p27 in this preparation revealed a value of 106 ug/ml. Next, 25 μl of the undiluted viral stock was introduced into 0.6 ml clear snap-cap polypropylene Eppendorf tube.1 Then, 2.5 μl of 10% DIPE solution was added into the Eppendorf tube containing virus and vortexed for 15 seconds. The tube was spun (using an Eppendorf 5810R centrifuge) at room temp at 1000×g for 2 minutes. No bulk solvent was removed. The solvent was removed by vacuum centrifugation (Speedvac Concentrator Model SVC200H) at 2000 rpm with no heat for 30 minutes. The volume in the tube was adjusted to 25 μl with PBS. Total protein recovery was measured using a Pierce BCA protocol. Gels (12% SDS-PAGE) were employed for specific protein recoveries (env protein, pol protein, gp41, p27 and gag protein) and stained with Coomasie Blue and provided semi-quantitative results using OD. Western blots were run using serum from SIV-infected monkeys to measure envelope protein, gp66, gp41, p27, gag, and p6 gag. The viral infectivity of the preparation was determined using a luciferase assay and CEM-174 cells. The virus titer was 1045, a 2.5 log reduction from that measured in undelipidated stock. This delipidated SIV preparation appears to retain greater than 90% of the major protein constituents of SIVmac251 such as the gag and env proteins.

Next, the immunogenicity of the modified viral preparation was determined in the twenty adult female Balb/c mice described above that were each immunized subcutaneously with 25 ug of protein of 2-2 dithiopyridine-inactivated SIVmac251. On day 14, groups 3-6 were boosted with 10 ug to 0.01 ug (based on total protein of stock) of delipidated virus in 0.5 ml normal saline. The estimated actual virus protein content was equal to 1/10 that of total protein based on the ratio of total protein/p27 protein in stock. The mice were injected with the delipidated vaccine composition as follows:

TABLE 3

| Groups (containing 4 mice each) | Initial Immunization s.c. 2-2 dithiopyridine-inactivated SIVmac251 | Day 14 - Booster Injections i.v. |
| --- | --- | --- |
| GROUP 1 - Control | Non-immunized | Administered - saline without delipidated virus |
| GROUP 2 | Immunized | Not administered |
| GROUP 3 | Immunized | 0.5 ml saline + 10 ug of delipidated virus |
| GROUP 4 | Immunized | 0.5 ml saline + 1.0 ug of delipidated virus |
| GROUP 5 | Immunized | 0.5 ml saline + 0.1 ug of delipidated virus |
| GROUP 6 | Immunized | 0.5 ml saline + 0.01 ug of delipidated virus |

Four days after the booster injection, the mice were anesthetized and blood was collected via retro-orbital puncture and intra-cardiac puncture. About 0.5 ml of blood was collected from each mouse, primarily from intra-cardiac puncture.

The blood was permitted to clot at room temperature. The spleen of each mouse was aseptically removed and transported to the lab under double bag containment. The clotted blood from each mouse was centrifuged at about 450×g at room temperature, and serum was collected from tube, transferred to a sterile tube, and stored at −70° C. until use. ELISA was performed to determine antibody titers against SIV for each serum sample.

SIV ELISA Protocol

Stocks of positive and negative serum and fluids to be tested were frozen in aliquots to be used on every plate to standardize each run.

Coated Corning Easy-Plates were washed with 100 ul per well of poly-1-lysine at a concentration of 10 ug per ml of PBS, pH 7.2-7.4. Plates were covered and incubated overnight at 4° C. Several plates were coated at one time and stored for subsequent use. Next, excess polylysine was removed and the plate dried for a few minutes. About 100 ul of 2% Triton-X was added to 100 ul of the stock ABI SIVmac251 the samples sat for 5 minutes. Next, 50 ul of coating buffer of pH 9.6 was added. Next, 100 ul of the viral antigen was added to each well of 5 plates, which were covered and incubated at 4° C. overnight.

After the overnight incubation, wells were washed 3 times with PBS-T. The wells then received 200 ul per well of 2% nonfat dry milk in PBS for one hour at room temperature to block non-specific binding. Excess fluid was removed. About 100 ul of test or control serum diluted at 1/100 in 10% RPMI 1640 or PBS with 10% calf serum was added to duplicate wells and incubated for 2 hours at 37° C. Wells were washed 4 times with PBS-T. Next 100 ul of Southern Biotech (from Fisher) alkaline phosphatase anti Mouse IgG (diluted 1/800 in media or PBS with 10% calf serum) was added and incubated 1 hour at 37° C. Wells were washed 4 times with PBS-T.

The BIORAD Alkaline Phosphatase Substrate kit was used to develop a reaction product. One substrate tablet was added for each 5 ml of 1X buffer and mixed. Next 100 ul was added per well and evaluated at about 5, 10, 15, 30 and then at 1 hour intervals for color development.

Blank readings were obtained from the media controls when the positive control was above 1.500 and the negative control was 0.100 to 0.200 for the serum. The results were then recorded and the means and the standard deviations of the negative control, positive control and the experimental samples were calculated. The negative cutoff value was the mean of the negative control plus 0.150.

Immunogenicity Results

The immunogenicity of the delipidated SIV virus preparation in mice was examined with an ELISA assay. The mean optical density (O.D.) was examined at 405 nm at various dilutions of serum. Table 4 provides the results of the ELISA test on serum samples.

TABLE 4

| Serum dil. | No boost | 10 ug boost | 1 ug boost | 0.1 ug boost | 0.01 ug boost |
|---|---|---|---|---|---|
| 1/100 | 2.541 | 3.663 | 3.289 | 2.846 | 2.627 |
| 1/500 | 1.035 | 2.86 | 2.055 | 1.458 | 1.257 |
| 1/2500 | 0.449 | 1.239 | 0.855 | 0.601 | 0.445 |
| 1/12500 | 0.194 | 0.463 | 0.304 | 0.229 | 0.181 |
| 1/62500 | 0.127 | 0.151 | 0.153 | 0.129 | 0.123 |
| 1/312500 | 0.11 | 0.116 | 0.108 | 0.108 | 0.107 |

Analysis of Responses of Dissociated Spleen Cells Obtained from Immunized Mice

A single cell suspension of spleen cells was prepared from each individual mouse by gently teasing the splenic capsule and passing the cells through a 25 gauge needle. Spleen cells were dissociated into a single cell suspension in medium (RPMI 1640 supplemented with 100 ug/ml penicillin, 100 ug/ml streptomycin, 2 mM L-glutamine), washed twice in medium and subsequently adjusted to 10 million cells/ml. 0.1 ml of this cell suspension from each mouse was dispensed into each well of a 96 well round bottom microtiter plate containing medium. Remaining cells were cryopreserved. These spleen cell cultures were then assessed for the ability of $CD4^+$ and $CD8^+$ T cells to synthesize IFN-gamma by standard intracellular cytokine staining (ICC) and flow cytometry.

Two individual wells containing the duplicate cell cultures from an individual mouse received either a) 0.1 ml of medium containing 2 ug/ml of each of a pool of SIV envelope (SE) peptides, ranging from 8 to 9 peptides per pool depending on the pool (n=17 pools), or b) 0.1 ml of medium containing 2 ug/ml of each of a pool of SIV gag (SG) peptides, ranging from 7 to 8 peptides per pool depending on the pool (n=16 pools). Controls consisted of spleen cell cultures that received media alone (background control) or a previously determined optimum concentration of phorbol myristic acetate (PMA 1 ug/ml)+ ionomycin (0.25 ug/ml) for maximal EFN-gamma staining (positive control). The SIV env peptides (n=72 individual peptides) were mixed in a grid fashion of an 8×9 matrix and the SIV gag peptides (n=62 peptides with two pools missing a peptide each and one pool missing two peptides) were mixed in a grid fashion of an 8×8 matrix which permitted identification of individual peptide specific immune responses. The SIV gag peptides were generally synthetic 20 mer peptides that overlapped each other by 12 amino acids and encompassed the entire SIV gag sequence. The SIV env peptides were generally synthetic 25 mer peptides that overlapped each other by 13 amino acids and encompassed the entire SIV env sequence. Peptide pools were made to contain 2.0 ug/ml of each peptide. For each spleen cell preparation there were 36 wells of culture. The components of the pools of env and gag overlapping peptides are described below. Shown are the peptides that compose the pools with their respective position within SIVmac239gag (SG) and env (SE).

TABLE 5

Pool arrangement of individual SIV mac 239 gag peptides (20-mers) overlap by 12

| | Pool 1 | Pool 2 | Pool 3 | Pool 4 | Pool 5 | Pool 6 | Pool 7 | Pool 8 |
|---|---|---|---|---|---|---|---|---|
| Pool 9 | Sg 1 | Sg 2 | Sg 3 | Sg 4 | Sg 5 | Sg 6 | Sg 7 | Sg 8 |
| Pool 10 | Sg 9 | Sg 10 | Sg 11 | Sg 12 | Sg 13 | Sg 14 | Sg 15 | Sg 16 |
| Pool 11 | Sg 17 | Sg 18 | Sg 19 | Sg 20 | Sg 21 | Sg 22 | Sg 23 | Sg 24 |
| Pool 12 | Sg 25 | Sg 26 | Sg 27 | Sg 28 | Sg 29 | Sg 30 | Sg 31 | Sg 32 |
| Pool 13 | Sg 33 | Sg 34 | Sg 35 | Sg 36 | Sg 37 | Sg 38 | Sg 39 | Sg 40 |
| Pool 14 | Sg 41 | Sg 42 | Sg 43 | Sg 44 | Sg 45 | Sg 46 | Sg 47 | Sg 48 |
| Pool 15 | Sg 49 | Sg 50 | Sg 51 | Sg 52 | Sg 53 | Sg 54 | Sg 55 | Sg 56 |
| Pool 16 | Sg 57 | Sg 58 | Sg 59 | Sg 60 | Sg 61 | Sg 62 | | |

TABLE 6

Pool arrangement of individual SIV mac239 env peptides (25-mer) overlapping by 13

| | Pool 1 | Pool 2 | Pool 3 | Pool 4 | Pool 5 | Pool 6 | Pool 7 | Pool 8 |
|---|---|---|---|---|---|---|---|---|
| Pool 9 | Se 1 | Se 2 | Se 3 | Se 4 | Se 5 | Se 6 | Se 7 | Se 8 |
| Pool 10 | Se 9 | Se 10 | Se 11 | Se 12 | Se 13 | Se 14 | Se 15 | Se 16 |
| Pool 11 | Se 17 | Se 18 | Se 19 | Se 20 | Se 21 | Se 22 | Se 23 | Se 24 |
| Pool 12 | Se 25 | Se 26 | Se 27 | Se 28 | Se 29 | Se 30 | Se 31 | Se 32 |
| Pool 13 | Se 33 | Se 34 | Se 35 | Se 36 | Se 37 | Se 38 | Se 39 | Se 40 |
| Pool 14 | Se 41 | Se 42 | Se 43 | Se 44 | Se 45 | Se 46 | Se 47 | Se 48 |
| Pool 15 | Se 49 | Se 50 | Se 51 | Se 52 | Se 53 | Se 54 | Se 55 | Se 56 |
| Pool 16 | Se 57 | Se 58 | Se 59 | Se 60 | Se 61 | Se 62 | Se 63 | Se 64 |
| Pool 17 | Se 65 | Se 66 | Se 67 | Se 68 | Se 69 | Se 70 | Se 71 | Se 72 |

TABLE 7

| | SIV mac 239 gag peptides. | | |
|---|---|---|---|
| SEQ ID NO:1 | MGVRNSVLSGKKADELEKIR | SG 1 | 1-20 |
| SEQ ID NO:2 | SGKKADELEKIRLRPNGKKK | SG 2 | 9-28 |
| SEQ ID NO:3 | EKIRLRPNGKKKYMLKHVVW | SG 3 | 17-36 |
| SEQ ID NO:4 | GKKKYMLKHVVWAANELDRF | SG 4 | 25-44 |
| SEQ ID NO:5 | HVVWAANELDRFGLAESLLE | SG 5 | 33-52 |
| SEQ ID NO:6 | LDRFGLAESLLENKEGCQKI | SG 6 | 41-60 |
| SEQ ID NO:7 | SLLENKEGCQKILSVLAPLV | SG 7 | 49-68 |
| SEQ ID NO:8 | CQKILSVLAPLVPTGSENLK | SG 8 | 57-76 |
| SEQ ID NO:9 | APLVPTGSENLKSLYNTVCV | SG 9 | 65-84 |
| SEQ ID NO:10 | ENLKSLYNTVCVIWCIHAEE | SG 10 | 73-92 |
| SEQ ID NO:11 | TVCVIWCIHAEEKVKHTEEA | SG 11 | 81-100 |
| SEQ ID NO:12 | HAEEKVKHTEEAKQIVRHL | SG 12 | 89-108 |
| SEQ ID NO:13 | TEEAKQIVQRHLVVETGTT | SG 13 | 97-115 |
| SEQ ID NO:14 | VQRHLVVETGTTETMPKTSR | SG 14 | 104-123 |
| SEQ ID NO:15 | GTTETMPKTSRPTAPSSGRG | SG 15 | 113-132 |
| SEQ ID NO:16 | TSRPTAPSSGRGGNYPVQQI | SG 16 | 121-140 |
| SEQ ID NO:17 | SCRGGNYPVQQIGGNYVHL | SG 17 | 129-147 |
| SEQ ID NO:18 | PVQQIGGNYVHLPLSPRTLN | SG 18 | 136-155 |
| SEQ ID NO:19 | YVHLPLSPRTLNAWVKLIEE | SG 19 | 144-163 |
| SEQ ID NO:20 | RTLNAWVKLIEEKKFGAEVV | SG 20 | 152-171 |
| SEQ ID NO:21 | LIEEKKFGAEVVPGFQALSE | SG 21 | 160-179 |
| SEQ ID NO:22 | AEVVPGFQALSEGCTPYDIN | SG 22 | 168-187 |
| SEQ ID NO:23 | ALSEGCTPYDINQMLNCVGD * | SG 23 | 176-195 |
| SEQ ID NO:24 | YDINQMLNCVGDHQAAMQII | SG 24 | 184-203 |
| SEQ ID NO:25 | CVGDHQAAMQIIRDIINEEA | SG 25 | 192-211 |
| SEQ ID NO:26 | MQIIRDIINEEAADWDLQH | SG 26 | 200-218 |
| SEQ ID NO:27 | NEEAADWDLQHPQPAPQQGQ | SG 27 | 208-227 |
| SEQ ID NO:28 | LQHPQPAPQQGQLREPSGSDI | SG 28 | 216-236 |
| SEQ ID NO:29 | GQLREPSGSDIAGTTSSVDE | SG 29 | 226-245 |
| SEQ ID NO:30 | SDIAGTTSSVDEQIQWMYRQ | SG 30 | 234-253 |
| SEQ ID NO:31 | SVDEQIQWMYRQQNPIPVGN | SG 31 | 242-261 |
| SEQ ID NO:32 | MYRQQNPIPVGNIYRRWIQL | SG 32 | 250-269 |
| SEQ ID NO:33 | PVGNIYRRWIQLGLQKCVRM | SG 33 | 258-277 |
| SEQ ID NO:34 | WIQLGLQKCVRMYNPTNILD | SG 34 | 266-285 |
| SEQ ID NO:35 | CVRMYNPTNILDVKQGPKE | SG 35 | 274-292 |
| SEQ ID NO:36 | TNILDVKQGPKEPFQSYVDR | SG 36 | 281-300 |
| SEQ ID NO:37 | GPKEPFQSYVDRFYKSLRAE | SG 37 | 289-308 |
| SEQ ID NO:38 | YVDRFYKSLRAEQTDAAVKN | SG 38 | 297-316 |
| SEQ ID NO:39 | LRAEQTDAAVKNWMTQTLLI | SG 39 | 305-324 |

TABLE 7-continued

SIV mac 239 gag peptides.

| | | | |
|---|---|---|---|
| SEQ ID NO:40 | AVKNWMTQTLLIQNANPDCK | SG 40 | 313-332 |
| SEQ ID NO:41 | TLLIQNANPDCKLVLKGLGV | SG 41 | 321-340 |
| SEQ ID NO:42 | PDCKLVLKGLGVNPTLEEML | SG 42 | 329-348 |
| SEQ ID NO:43 | GLGVNPTLEEMLTACQGVCG | SG 43 | 337-356 |
| SEQ ID NO:44 | EEMLTACQGVGGPGQKARLM | SG 44 | 345-364 |
| SEQ ID NO:45 | GVGGPGQKARLMAEALKEAL | SG 45 | 353-372 |
| SEQ ID NO:46 | ARLMAEALKEALAPVPIPFA | SG 46 | 361-380 |
| SEQ ID NO:47 | KEALAPVPIPFAAAQQRGPRK | SG 47 | 369-389 |
| SEQ ID NO:48 | PFAAAQQRGPRKPIKCWNCG | SG 48 | 378-397 |
| SEQ ID NO:49 | GPRKPIKCWNCGKEGHSARQ | SG 49 | 386-405 |
| SEQ ID NO:50 | WNCGKEGHSARQCRAPRRQG | SG 50 | 394-413 |
| SEQ ID NO:51 | SARQCRAPRRQGCWKCGKMD | SG 51 | 402-421 |
| SEQ ID NO:52 | RRQGCWKCGKMDHVMAKCPTA | SG 52 | 410-430 |
| SEQ ID NO:53 | KMDHVMAKCPDRQAGFLGLG | SG 53 | 419-438 |
| SEQ ID NO:54 | CPDRQAGFLGLCPWGKKPRN | SG 54 | 427-446 |
| SEQ ID NO:55 | LGLGPWGKKPRNFPMAQVHQ | SG 55 | 435-454 |
| SEQ ID NO:56 | KPRNFPMAQVHQGLMPTA | SG 56 | 443-460 |
| SEQ ID NO:57 | MAQVHQGLMPTAPPEDPAVD | SG 57 | 449-458 |
| SEQ ID NO:58 | MPTAPPEDPAVDLLKNYMQL | SG 58 | 457-476 |
| SEQ ID NO:59 | PAVDLLKNYMQLGKQQREKQ | SG 59 | 465-484 |
| SEQ ID NO:60 | YMQLGKQQREKQRESREKPYK | SG 60 | 473-493 |
| SEQ ID NO:61 | EKQRESREKPYKEVTEDLLH | SG 61 | 482-501 |
| SEQ ID NO:62 | KPYKEVTEDLLHLNSLFGGDQ | SG 62 | 490-510 |

SEQ ID NO: 63
```
  1 MGVRNSVLSG KKADELEKIR LRPNGKKKYM LKHVVWAANE LDRFGLAESL
 51 LENKEGCQKI LSVLAPLVPT GSENLKSLYN TVCVIWCIHA EEKVKHTEEA
101 KQIVQRHLVV ETGTTETMPK TSRPTAPSSG RGGNYPVQQI GGNYVHLPLS
151 PRTLNAWVKL IEEKKFGAEV VPGFQALSEG CTPYDINQML NCVGDHQAAM
201 QIIRDIINEE AADWDLQHPQ PAPQQGQLRE PSGSDIAGTT SSVDEQIQWM
251 YRQQNPIPVG NIYRRWIQLG LQKCVRMYNP TNILDVKQGP KEPFQSYVDR
301 FYKSLRAEQT DAAVKNWMTQ TLLIQNANPD CKLVLKGLGV NPTLEEMLTA
351 CQGVGGPGQK ARLMAEALKE ALAPVPIPFA AAQQRGPRKP IKCWNCGKEG
401 HSARQCRAPR RQGCWKCGKM DHVMAKCPDR QAGFLGLGPW GKKPRNFPMA
451 QVHQGLMPTA PPEDPAVDLL KNYMQLGKQQ REKQRESREK PYKEVTEDLL
501 HLNSLFGGDQ
```

These peptides are generally 20 mers overlapping by 12 amino acids. They were selected for synthesis, with the proviso that there was no Q at the amino terminus, and no P in last or second to last position at the carboxy terminus).
The amino acid sequence for gag of SIVmac239 is shown in SEQ ID NO:63.

The following peptides are located within SEQ ID NO:63: p. 17 (1-135 SG 1-16); p. 27 (136-354 SG 17-43); x peptide (355-371 SG 44-45); p. 9 (372-447 SG 46-65); and, p. 6 (448-510 SG 56-62).

TABLE 8

Overlapping peptides in Env of SIVmac239 (25-mer with 13-mer overlapping)

| | | | |
|---|---|---|---|
| SEQ ID NO:64 | MGCLGNQLLIAILLLSVYGIYCTLY | SE1 | 1-25 |
| SEQ ID NO:65 | LLLSVYGIYCTLYVTVFYGVPAWRN | SE2 | 13-37 |
| SEQ ID NO:66 | YVTVFYGVPAWRNATIPLFCATKNR | SE3 | 25-49 |
| SEQ ID NO:67 | NATIPLFCATKNRDTWGTTQCLPDN | SE4 | 37-61 |
| SEQ ID NO:68 | RDTWGTTQCLPDNGDYSEVALNVTE | SE5 | 49-73 |
| SEQ ID NO:69 | NGDYSEVALNVTESFDAWNNTVTEQ | SE6 | 61-85 |
| SEQ ID NO:70 | ESFDAWNNTVTEQAIEDVWQLFETS | SE7 | 73-97 |
| SEQ ID NO:71 | QAIEDVWQLFETSIKPCVKLSPLCI | SE8 | 85-109 |
| SEQ ID NO:72 | SIKPCVKLSPLCITMRCNKSETDRW | SE9 | 97-121 |
| SEQ ID NO:73 | TMRCNKSETDRWGLTKSITTTAST | SE10 | 109-133 |
| SEQ ID NO:74 | WGLTKSITTTASTTSTTASAKVDMV | SE11 | 121-145 |
| SEQ ID NO:75 | TTSTTASAKVDMVNETSSCIAQDNC | SE12 | 133-157 |
| SEQ ID NO:76 | VNETSSCIAQDNCTGLEQEQMISCK | SE13 | 145-169 |
| SEQ ID NO:77 | CTGLEQEQMISCKFNMTGLKRDKKK | SE14 | 157-181 |
| SEQ ID NO:78 | KFNMTGLKRDKKKEYNETWYSADLV | SE15 | 169-193 |
| SEQ ID NO:79 | KEYNETWYSADLVCEQGNNTGNESR | SE16 | 181-205 |
| SEQ ID NO:80 | VCEQGNNTGNESRCYMNHCNTSVIQ | SE17 | 193-217 |
| SEQ ID NO:81 | RCYMNHCNTSVIQESCDKHYWDAIR | SE18 | 205-229 |
| SEQ ID NO:82 | QESCDKHYWDAIRFRYCAPPGYALL | SE19 | 217-241 |
| SEQ ID NO:83 | RFRYCAPPGYALLRCNDTNYSGFMP | SE20 | 229-253 |
| SEQ ID NO:84 | LRCNDTNYSGFMPKCSKVVVSSCTR | SE21 | 241-265 |
| SEQ ID NO:85 | PKCSKVVVSSCTRMMETQTSTWFGF | SE22 | 253-277 |
| SEQ ID NO:86 | RMMETQTSTWFGFNGTRAENRTYIY | SE23 | 265-289 |
| SEQ ID NO:87 | FNGTRAENRTYIYWHGRDNRTIISL | SE24 | 277-301 |
| SEQ ID NO:88 | YWHGRDNRTIISLNKYYNLTMKCRR | SE25 | 289-313 |
| SEQ ID NO:89 | LNKYYNLTMKCRRPGNKTVLPVTIM | SE26 | 301-325 |
| SEQ ID NO:90 | RPGNKTVLPVTIMSGLVFHSQPIND | SE27 | 313-337 |
| SEQ ID NO:91 | MSGLVFHSQPINDRPKQAWCWFGGK | SE28 | 325-349 |
| SEQ ID NO:92 | DRPKQAWCWFGGKWKDAIKEVKQTI | SE29 | 337-361 |
| SEQ ID NO:93 | KWKDAIKEVKQTIVKHPRYTGTNNT | SE30 | 349-373 |
| SEQ ID NO:94 | IVKHPRYTGTNNTDKINLTAPGGGD | SE31 | 361-385 |
| SEQ ID NO:95 | TDKINLTAPGGGDPEVTFMWTNCRG | SE32 | 373-397 |
| SEQ ID NO:96 | DPEVTFMWTNCRGEFLYCKMNWFLN | SE33 | 385-409 |
| SEQ ID NO:97 | GEFLYCKMNWFLNWVEDRNTANQKP | SE34 | 397-421 |
| SEQ ID NO:98 | NWVEDRNTANQKPKEQHKRNYVPCH | SE35 | 409-433 |

TABLE 8-continued

Overlapping peptides in Env of SIVmac239
(25-mer with 13-mer overlapping)

| | | | |
|---|---|---|---|
| SEQ ID NO:99 | PKEQHKRNYVPCHIRQIINTWHKVG | SE36 | 421-445 |
| SEQ ID NO:100 | HIRQIINTWHKVGKNVYLPPREGDL | SE37 | 433-457 |
| SEQ ID NO:101 | GKNVYLPPREGDLTCNSTVTSLIAN | SE38 | 445-469 |
| SEQ ID NO:102 | LTCNSTVTSLIANIDWIDGNQTNIT | SE39 | 457-481 |
| SEQ ID NO:103 | NIDWIDGNQTNITMSAEVAELYRLE | SE40 | 469-493 |
| SEQ ID NO:104 | TMSAEVAELYRLELGDYKLVEITPI | SE41 | 481-505 |
| SEQ ID NO:105 | ELGDYKLVEITPIGLAPTDVKRYTT | SE42 | 493-517 |
| SEQ ID NO:106 | IGLAPTDVKRYTTGGTSRNKRGVFV | SE43 | 505-529 |
| SEQ ID NO:107 | TGGTSRNKRGVFVLGFLGFLATAGS | SE44 | 517-541 |
| SEQ ID NO:108 | VLGFLGFLATAGSAMGAASLTLTAQ | SE45 | 529-553 |
| SEQ ID NO:109 | SAMGAASLTLTAQSRTLLAGIVQQQ | SE46 | 541-565 |
| SEQ ID NO:110 | QSRTLLAGIVQQQQQLLDVVKRQQE | SE47 | 553-577 |
| SEQ ID NO:111 | QQQLLDVVKRQQELLRLTVWGTKNL | SE48 | 565-589 |
| SEQ ID NO:112 | ELLRLTVWGTKNLQTRVTAIEKYLK | SE49 | 577-601 |
| SEQ ID NO:113 | LQTRVTAIEKYLKDQAQLNAWGCAF | SE50 | 589-613 |
| SEQ ID NO:114 | KDQAQLNAWGCAFRQVCHTTVPWPN | SE51 | 601-625 |
| SEQ ID NO:115 | FRQVCHTTVPWPNASLTPKWNNETW | SE52 | 613-637 |
| SEQ ID NO:116 | NASLTPKWNNETWQEWERKVDFLEE | SE53 | 625-649 |
| SEQ ID NO:117 | WQEWERKVDFLEENITALLEEAQIQ | SE54 | 637-661 |
| SEQ ID NO:118 | ENITALLEEAQIQQEKNMYELQKLN | SE55 | 649-673 |
| SEQ ID NO:119 | QQEKNMYELQKLNSWDVFGNWFDLA | SE56 | 661-685 |
| SEQ ID NO:120 | NSWDVFGNWFDLASWIKYIQYGVYI | SE57 | 673-697 |
| SEQ ID NO:121 | ASWIKYIQYGVYIVVGVILLRIVIY | SE58 | 685-709 |
| SEQ ID NO:122 | IVVGVILLRIVIYIVQMLAKLRQGY | SE59 | 697-721 |
| SEQ ID NO:123 | YIVQMLAKLRQGYRPVFSSPPSYFQ | SE60 | 709-733 |
| SEQ ID NO:124 | YRPVFSSPPSYFQQTHIQQDPALPT | SE61 | 721-745 |
| SEQ ID NO:125 | QQTHIQQDPALPTREGKERDGGEGG | SE62 | 733-757 |
| SEQ ID NO:126 | TREGKERDGGEGGGNSSWPWQIEYI | SE63 | 745-769 |
| SEQ ID NO:127 | GGNSSWPWQIEYIHFLIRQLIRLLT | SE64 | 757-781 |
| SEQ ID NO:128 | IHFLIRQLIRLLTWLFSNCRTLLSR | SE65 | 769-793 |
| SEQ ID NO:129 | TWLFSNCRTLLSRVYQILQPILQRL | SE66 | 781-805 |
| SEQ ID NO:130 | RVYQILQPILQRLSATLQRIREVLR | SE67 | 793-817 |
| SEQ ID NO:131 | LSATLQRIREVLRTELTYLQYGWSY | SE68 | 805-829 |
| SEQ ID NO:132 | RTELTYLQYGWSYFHEAVQAVWRSA | SE69 | 817-841 |
| SEQ ID NO:133 | YFHEAVQAVWRSATETLAGAWGDLW | SE70 | 829-853 |
| SEQ ID NO:134 | ATETLAGAWGDLWETLRRGGRWILA | SE71 | 841-865 |
| SEQ ID NO:135 | WETLRRGGRWILAIPRRIRQGLELTLL | SE72 | 853-877 |

The cultures were incubated overnight at 37° C. in a 7% $CO_2$ humidified atmosphere. Cells from each well were gently removed, transferred to 5.0 ml FACS test tubes and washed. One set of cells was stained with anti-CD3+ anti-CD4+. The other duplicate set was stained with anti-CD3+ anti-CD8+ (see below). These cell surface stained cells were then permeabilized and stained for intracellular content of IFN-gamma using an anti-IFN-gamma staining antibody using standard intracellular staining protocols. Each stained cell population (about 10,000 cells from each tube) was then analyzed using a FACS flow cytometer and the frequency of $CD3^+$ $CD4^+$ and $CD3^+$ $CD8+T$ cells synthesizing IFN-gamma was determined. The negative and positive controls were utilized for background control and for positive control references. About 1000 analyses were performed in this manner during this experiment.

The frequency of $CD4^+$ T cells (y axis) that expressed IFN-gamma by spleen cells from the six groups of mice in response to pools of SIV env peptide (17 pools) and SIV gag peptides (16 pools) were determined. Also determined was the frequency of $CD8^+$ T cells (y axis) that express IFN-gamma by spleen cells from the same six groups of mice in response to pools of SIV env peptide and SIV gag peptides. Data were the mean value from 4 mice/group. Results of these initial studies indicated that delipidated SIVmac251 at a dose of 10 ug or 1.0 ug led to marked augmentation of the SIV specific humoral responses in previously primed BALB/c mice. Even a dose of 0.1 ug ($5 \times 10^6$ viral particles) led to detectable enhancement of the SIV specific humoral responses in these mice. A dose of 1.0 ug, but not 10 ug, led to markedly broad breadth of SIV env and SIV gag peptide specific $CD4^+$ T cell responses as measured by IFN-g synthesis in previously primed BALB/c mice.

EXAMPLE 4

Direct Delipidation of HIV-1 and Removal of Solvents with Charcoal Column and Retention of HIV Proteins About 25 ul of 1000×HIV-1 IIIB was mixed with 1) nothing; 2) 12.5 ul butanol/DIPE (25:75); 3) 2.5 ul 100% DIPE; or 4) 12.5 ul 1% DIPE in PBS and the samples were vortexed for 15 seconds. A charcoal column (0.5-ml) was generated by loading 2 ml of PBS-washed Hemasorba charcoal into 3-ml BD LuerLock syringe containing a Whatman filter frit. The column was washed with 5% glucose/PBS (5 to 10 column volumes). The column was incubated in 5% glucose/PBS for 30 min. This column was used to remove solvents from treated plasma. The virus-solvent mixtures were loaded individually onto separate columns. The columns were chased with 1 ml of PBS. The elution volumes were measured and samples assayed for p24 by ELISA, protein, and subjected to Western blotting.

The samples treated with 1% DIPE showed excellent p24 recovery compared to controls. The samples treated with 10% DIPE or butanol/DIPE showed slightly less p24 recovery. The total protein recovery was similar in terms of percentage relative to control, to the p24 results obtained 1% DIPE, 10% DIPE or butanol/DIPE.

Western blot analysis, performed in a similar manner to the protocol provided below in this example, revealed numerous immunoreactive bands when probed with human anti-HIV IgG with butanol/DIPE, 10% DIPE or 1% DIPE solvent treatments. Western blot analysis also revealed positive immunoreactive bands corresponding to p24 with butanol/DIPE, 10% DIPE or 1% DIPE. Positive immunoreactive bands were observed for gp41 using 10% DIPE or 1% DIPE. Additional positive immunoreactive bands were observed for gp120 with butanol/DIPE, 10% DIPE or 1% DIPE, although the intensity of staining was higher with 10% DIPE or 1% DIPE.

SIV and HIV Western Blot Analysis

Reagents for comparison included delipidated SIVmac251, heat inactivated SIV mac251 and a rabbit polyclonal antibody against whole SIV (available through the AIDS reagent repository, Rockville, Md.). About 1 ug of protein was required to visualize most of the SIV bands in the Western blot. SDS-polyacrylamide gel electrophoresis (SDS-PAGE) was performed on the viral lysates (lysate buffer: 50 mM Tris-HCl, pH 7.4; 1% NP-40; 0.25% sodium deoxycholate; 150 mM NaCl; 1 mM EGTA; 1 mM PMSF; 1 ug/ml each of aprotinin, leupeptin and pepstatin; 1 mM sodium vanadate; 1 mM NaF).

A silver stain was used to visualize the bands which reveal the various viral proteins present following delipidation with respect to molecular weight standards. The heat inactivated SIVmac251 proteins were compared with the delipidated SIVmac251 proteins on the gels. A similar SDS-PAGE was run and the proteins are transferred to nitrocellulose. The blotted nitrocellulose was washed twice with water. A minimum of three blots each for the delipidated SIVmac251 and the heat inactivated SIVmac251 were run.

The blotted nitrocellulose was blocked in freshly prepared PBS containing 3% nonfat dry milk (MLK) for 20 min at 20-25° C. with constant agitation. The nitrocellulose strips were incubated with a freshly prepared pre-determined optimum concentration of the rabbit polyclonal anti-SIV antiserum (about 5 ml of a 1:1000 dilution of the antiserum in PBS-MLK) overnight with agitation. The nitrocellulose strips were washed twice with water. The strips were incubated with horseradish peroxidases (HRP)-conjugated goat anti-rabbit IgG 1:3000 dilution in PBS-MLK for 90 min at room temperature with agitation. The nitrocellulose was washed with water twice and then with PBS-0.05% Tween 20 for 3-5 min. The nitrocellulose strips were washed with 4-5 changes of water. Detection of the developed bands was achieved via detection of the developed bands. The bands developed using the heat inactivated SIV with the delipidated SIV were compared.

A similar approach was used for Western blot analysis of solvent treated HIV-1 passed through charcoal columns and probed for p24, gp41, gp120, and also for HIV antigens using an human anti-HIV IgG. Western blotting was performed on SDS-PAGE separated virus samples transferred onto nitrocellulose membranes. The membranes are probed with polyclonal and monoclonal antibodies to viral proteins and developed with secondary antibodies conjugated with peroxidase and enhanced chemiluminescence reagents.

EXAMPLE 5

Development of a Modified SARS Viral Particle for Use as a Vaccine

A. Optimization of a solvent treatment method for SARS virus

Seed virus production of virus. Stock SARS virus (specimen number 809940 strain 200300592) was obtained from the Centers for Disease Control (CDC). The virus is grown in Vero E6 cells (ATCC CRL 1586). The virus sample is thawed and 0.1 ml is inoculated with a pipette into each of 5 test tubes of Vero E6 cells containing about 2 ml outgrowth medium (90% Eagle's minimal essential medium in Earle's balanced salt solution with 10% fetal bovine serum). The remainder of the virus sample is stored at −80° C. When 75-100% of the cell sheet in each tube show cytopathic effects (CPE), the cells are harvested by freezing and scraping, pooled and frozen at −80° C. in 1 ml aliquots. The virus is titered in test tubes of Vero E6 cells by the $TCID_{50}$ method (serial 1:10 dilutions of virus in quadruplicate).

Solvent treatment of virus. SARS virus is solvent-treated by various methods used for SIV, DHBV and BVDV as described herein, to optimize the process for maximum envelope protein recovery and minimum residual infectivity. Parameters explored for SARS virus solvent treatment are: solvent type or combinations; solvent ratios; solvent to virus ratio; treatment time; treatment temperature; mixing method; and solvent removal process. Stock SARS virus preparations in PBS (phosphate buffered saline) are combined with DIPE resulting in about 2000 to 10,000 ppm and mixed by end over end rotation for 20 to 60 minutes followed by centrifugation at 1000×g for 2 minutes. Residual solvent is removed by either vacuum evaporation or adsorption to activated charcoal. In addition, combinations of DIPE and n-Butanol are tested in ratios of 60:40 to 95:5 (vol/vol), resulting in about 200 to 40,000 ppm total solvent concentration, mixed end over end for 20 to 60 minutes followed by centrifugation at 1000×g for 2 minutes. Residual solvent is removed by adsorption to activated charcoal.

All samples from the various treatment methods described above are characterized by PAGE, including Western blot, to determine presence of viral protein and total protein. Quantification of specific viral antigens and proteins are evaluated by immunospecific assay such as ELISA. Infectivity is evaluated using Vero E6 cytopathic assay (Reed and Muench; Am. J. Hygiene 1938; 27:493-497). Selection is made as to the most effective method of solvent treatment based on maximum target viral protein recovered, greatest reduction in infectivity and immunogenicity in mice.

B. Optimization of a Chemical Treatment Method for SARS Based on Known Viral Inactivation Agents In situations where the present treatment method reduces infectivity to a level that is insufficient for a vaccine, chemical inactivation of the solvent-treated virus may be indicated. Chemical inactivation is considered successful if infectivity is reduced by 6 logs.

Methods. The light-activated cross-linking reagent psoralen is used. The psoralen tricyclic planar ring system intercalates into single stranded RNA and is light activated. NHS-psoralen (Pierce Biochemicals, Rockford Ill.) is dissolved in DMSO before adding to aqueous reaction mixture. The NHS ester cross-links to primary amines at pH 7-9. Solvent-treated virus solution is mixed with NHS-psoralen (150 mM) in 0.1M sodium phosphate, 0.15M NaCl, pH 7.2. Photoreactive coupling is achieved by exposure to light>350 nm for 30 minutes or 3 Joules/cm$^2$.

Cytopathic endpoints (CPE) in Vero E6 cells is typically noted on the fifth day post-inoculation. It is focal in appearance, with cell rounding and a refractiveness in the affected cells that is followed by cell detachment. The CPE quickly spreads to involve the entire cell monolayer within 24-48 hours. Thus if cell integrity is destroyed it indicates that the virus is infectious.

C. Evaluation of Native Viral Protein Structure and Viral Envelope Changes Post Treatment To evaluate the effect of the solvent treatment on viral proteins, virus samples are characterized by non-denaturing PAGE including Western Blot to determine presence of native viral protein. Total soluble protein is measured using SDS PAGE. The most effective method of solvent treatment is selected based on maximum target viral protein recovered and greatest reduction in infectivity. A double antibody sandwich ELISA is used to detect SARS antibodies (Current Protocols in Immunology, Vol 1, supp. 8, 1991, John E Coligan, et al. eds.; Richard Coico, series ed., publisher: Current Protocols, John Wiley and Sons). Polyclonal anti-SARS antibody is biotinylated and SARS virus antigen is produced from stock SARS virus.

Native gel electrophoresis. Native gel electrophoresis is performed at room temperature in polyacrylamide gels and proteins are visualized either with silver staining or are transferred to nitrocellulose for detection with labeled goat-anti-mouse antibodies (Western blot). Samples of SARS virus pre and post solvent treatment are analyzed using a pool of SARS virus proteins as a standard.

Western blot. Proteins on gels are transferred to nitrocellulose membranes. For high molecular weight proteins transfer time is at least 90 minutes. After blocking with BSA and milk, nitrocellulose is incubated with polyclonal antibodies to SARS virus spike and membrane proteins. Mouse antibodies are visualized with horseradish peroxidase conjugated goat anti-mouse antibodies. Commercially available SARS virus polyclonal antibodies are purchased. Alternatively, the antibodies are produced in weanling BALB/c mice by the method briefly described below.

Production of mouse anti-SARS antibodies. If SARS polyclonal antibodies are not commercially available, mice are injected with concentrated psoralen-treated stock virus preparation that has been purified by sucrose density gradient centrifugation. Inactivation is confirmed in Vero E6 cells. Twenty-two weanling BALB/c mice are divided into 2 groups of 8 mice each with the remaining 6 mice as controls. The two groups of 8 mice each are inoculated subcutaneously (sc) with 10 ug (low) or 50 ug (high) doses of the virus prep mixed with MPL (monophosphoryl lipid A, synthetic trehalose dicorynomycolate; Ribi Adjuvant System, Corixa Corp. Hamilton, Mont.). The 6 control mice are inoculated with an equivalent amount of the cell culture medium mixed with adjuvant. Inoculations are repeated at 2 and 4 weeks. At 6 weeks mice are anesthetized and exsanguinated by retro-orbital bleeding+intracardiac puncture. The serum from each group is pooled to titer for neutralizing antibody.

If SARS virus spike and membrane proteins are in their native conformation, antibodies raised to these intact proteins in mice are recognized in the Western blot. The silver stained gels are expected to show retention of viral proteins until the point where solvent treatment denatures the proteins such that they can no longer be detected by this method.

Additional and alternative methods. Additional methods are used to confirm results from Western blots. Electron microscopy is used to assess virus structural integrity and to compare changes pre and post solvent treatment (Graham D R, et al., (2003) J Virol. 77(15): 8237-8248). Viruses are inactivated with glutaraldehyde prior to removal from the BSL-3 facility.

EXAMPLE 6

Ability of Solvent and Chemically Treated SARS Viral Particles to Produce an Immune Response in Mice Animals are vaccinated with viral preparations from solvent treatment methods using varying concentrations of solvents, mixing times and energy as well as solvent combinations resulting in low to high degrees of lipid removal. Comparison of results from each method in the vaccinated animals is used to determine which viral prep provides the best immunological response. To be useful as a vaccine the solvent-treated SARS virus must be both antigenic, as evidenced by antibody production and cause increased cytokine production.

A. Injection of Mice with Solvent and Chemically Treated SARS Viral Particles for Antibody Production and to Test for the Elicitation of Neutralizing Antibodies Previously primed Balb/c mice are used to determine the minimal dose of solvent-treated SARS virus that leads to readily recognizable virus specific humoral or cellular immune response in these mice using methods described by Ansari A., et al. (J. Virology 76 (4): 1731-1743, 2002). Twenty adult female Balb/c mice are each injected with 25 ug of chemically inactivated SARS virus protein incorporated in an equal volume of adjuvant subcutaneously. Four mice serve as control non-immunized mice (Group 1).

Sufficient SARS virus is treated according to methods described in Example 5 so that the amount needed for boosting these mice per schedule is available. On day 14 following initial priming, 5 groups of 4 mice per group are treated as follows: Group 2—0.5 ml saline, Group 3—0.5 ml saline containing 10 ug of solvent-treated virus, Group 4—0.5 ml saline containing 1 ug of solvent-treated virus, Group 5—0.5 ml saline containing 0.1 ug of solvent-treated virus, Group 6—0.5 ml saline containing 0.01 ug of solvent-treated virus. Four days after boosting, all mice are anesthetized and blood is collected via retro-orbital puncture. Serum is obtained from the collected blood. Spleens are collected from each test mouse for spleen cell preparation (see below). Serum and spleen cells collected from these mice are used as the basis for the analyses as described below in this example.

B. Test for Production of Mouse Neutralizing Antibodies in Serum Using Vero E6 Cell Cytopathic Assay To determine if the treated virus preparations are capable of raising SARS virus neutralizing antibodies serum samples collected from the mouse immunization are tested to evaluate if they are capable of protecting Vero E6 cells from cytolysis.

Purification of virions. Briefly, viruses are isolated from clarified cell culture supernatants by two successive rounds of ultracentrifugation in 25 to 50% sucrose density gradients. Virus-containing fractions are identified by UV absorption at 254 and 280 nm. Peak UV-absorbing fractions are pooled, diluted to below 20% sucrose with TNE buffer (0.01 M Tris-HCl [pH 7.2], 0.1 M NaCl, and 1 mM EDTA), ultracentrifuged to a pellet, and resuspended in TNE buffer. Samples are stored at −80° C. Treated virus is prepared by incubating virus at the indicated concentration of capsid protein in the presence of the appropriate agent under the appropriate incubation conditions. Virus is then repurified through a 20% sucrose pad by ultracentrifugation for 1 h at 100,000×g at 4° C.

Virus Neutralization Assay. Stock SARS virus obtained from the CDC is titrated in quadruplicate in test tubes of freshly confluent Vero E6 cells for 7 days at 37° C. to obtain the $TCID_{50}/0.01$ ml based on the appearance of CPE. The inactivated mouse anti-SARS antiserum is serially diluted 1:10 using cell culture medium without serum. Equal volumes of diluted specific antiserum are mixed with 100 $TCID_{50}$ of stock SARS virus and incubated for 1 hour. Duplicate tubes of Vero E6 cells are inoculated with 0.2 ml of each virus-antiserum dilution mixture and incubated for 7 days. This titration is repeated with each neutralization assay. The dilution of antiserum that neutralizes at least 100 $TCID_{50}$ of virus, based on the appearance of CPE, represents one antibody unit. In additional neutralization assays, serial 1:10 dilutions of the virus to be confirmed as SARS and twenty antibody units of specific immune serum are employed in equal volumes.

Infectivity assay. Each solvent-treated sample of SARS virus is inoculated into two or four tubes of Vero E6 cells and incubated for at least 7 days to detect the presence of CPE. Non-solvent-treated stock SARS virus is inoculated as above as a control. Virus titers are calculated by $TCID_{50}$. It is expected that the SARS virus causes cells to round up, become refractive and detach in 24-48 hours. If neutralizing antibody is present, the cells remain intact. Neutralizing antibody in the test sera should protect cells from 100 $TCID_{50}$ of virus. If mouse antibodies to Vero cell proteins are produced, serum from mice injected with mock viral preparations starting with Vero E6 cells is used as a control. If necessary, anti-Vero cell antibodies are removed from mouse sera by affinity purification.

C. Evaluate Mouse Cellular Response on Vaccination with Solvent-treated SARS Viral Particles Cytokines are critical in orchestrating immune responses. A cellular response is significant relative to addressing the issue of transient immunity seen with other coronavirus vaccines. As an indication of mouse cellular immune response, the cytokine gamma interferon, and interleukins such as IL-2, are measured as used for retroviruses in vaccinated mice from the method described above in this example.

Collection of Spleen Cells and Intracellular Cytokine Staining Analysis. Spleen cells are collected aseptically and a single cell suspension made, by forcing through a narrow gauge needle. Cell counts are performed. Cells are resuspended at 1 million cells/ml in RPMI 1640 complete media (RPMI 1640+100 U/ml penicillin+100 ug/ml streptomycin+2 mM L-glutamine+10% select lot of fetal calf serum). Cell suspension (100,000 cells) is dispensed into wells of a 96-well plate. Media is added to triplicate wells (negative control) and phorbol myristic acetate (PMA 50 ng/ml)+Ionomycin (1 ug/ml) to 3 additional wells (positive control). The SARS pools of overlapping peptides (set up as a grid) to cover certain SARS coding sequences for viral structural genes (the E, M and S protein sequences) is then added to the appropriate wells. The media cocktail is added and incubated overnight. Add, incubate, remove and wash as appropriate for additions of BrefeldinA solution, antibody cocktail of PerCP-labeled CD4 and FITC-labeled CD8 in FACS wash. The contents of each well are transferred to FACS tubes followed by addition of penn/fix. After wash with Perm Wash, add phycoerythrin (PE) anti human IFN-gamma. Repeat incubation, wash and remove wash solution. Fresh 1% paraformaldehyde is added and samples are refrigerated in the dark until ready to analyze. The data on all samples is collected and the thresholds are drawn based on the signal obtained with the media control and PMA+Ionomycin. Data from on about 100,000 events is collected. The peptides are identified that induce a positive interferon gamma or interleukin response to overlapping peptides. The presence of cytokine positive cells indicate that the solvent-treated SARS virus is effective in eliciting a cellular immune response.

EXAMPLE 7

Delipidated SIV Virus Shows Reduced Infectivity and Causes $CD4^+$ and $CD8^+$ T-Cell Immunological Responses when Administered to Mice A prime-boost immunization strategy using SIV delipidated pursuant to the present invention gives rise to a broader $CD4^+$ and $CD8^+$ T-cell responses (interferon gamma production) in mice than aldrithiol-2 (AT-2) treated or live virus. More specifically, the present invention gives rise to an improved immunological response across a broader array of antigens as compared to non-delipidated viral particles. The present invention specifically encompasses a modified viral particle having an increased immunological response to a wider range of antigens, such as a range of a minimum of 5% more antigens as compared to non-delipidated viral particles.

In the present example, the delipidation of SIVmac251 reduced viral infectivity while retaining the major SIV proteins (env, gag, pol, tat). The studies were carried out in Balb/c mice immunized with AT-2-treated virus subcutaneously (sc) plus adjuvant and boosted with either AT-2-treated virus, live virus or delipidated virus. Routes of administration and intervals between prime and boost and dose levels were evaluated. Spleen cells were collected and cultured with individual pools of overlapping SIV env and gag peptides covering the entire SIV amino acid sequence for env and gag. The ability of the spleen cells to synthesize (interferon) IFN-gamma by standard intracellular cytokine staining (ICC) and flow cytometry was measured. Delipidation was performed using 1% DIPE.

Materials and Methods: SIVmac251 Antigen Treatments

AT-2 inactivation: For the purpose of primary immunization as well as boosting control, aliquots of sucrose banded SIVmac251 were inactivated via treatment with AT-2 as described previously (Rossio et al., J. Virol. 72: 7992, 1998). Briefly, a 100 mM stock solution of AT-2 (Aldrich, Milwaukee, Wis.) was prepared freshly in dimethyl sulfoxide (DMSO). AT-2 was then added directly to the virus at a final concentration of 300 μM and incubated for 1 h at 37° C. before aliquoting the virus and storing it at −70° C., until used for immunization. DIPE solvent treatment: Two hundred μg aliquots of sucrose purified SIVmac251 total protein were diluted in phosphate buffered saline (PBS) and added various amounts of diisopropyl ether (DIPE) (VWR, West Chester, Pa.) to bring the total volume to 1 mL in Eppendorf microfuge tubes to achieve various DIPE concentrations. Solvent treatment of the viral antigen preparation was performed for 20 minutes at room temperature. After a brief centrifugation to collect the sample to the bottom of the tubes, the solvent was evaporated in a Speedvac evaporator (Savant) for 90 minutes at room temperature. At the end of this procedure, the volume was reconstituted to 1 ml using injection grade water. A 25 μL of solvent-treated sample was diluted with 75 μL distilled water and submitted to gas chromatography analysis to ascertain removal of solvent. The acceptable limit of residual DIPE solvent in any sample used for immunization was ≦25 ppm. Each sample was then aliquoted in appropriate quantity for booster immunization and stored at −70° C.

Viral Protein Recovery and Infectivity Assays

The effect of solvent treatment of SIVmac251 was ascertained by total protein analysis using the BCA (Pierce, Rockford, Ill.) and the Lowry assay (Biorad, Hercules, Calif.), polyacrylamide gel electrophoresis followed by silver staining and by Western blot analysis using a pool of SIV reactive monkey serum. In addition, SIVgag p27 recovery was tested by EIA (Coulter Immunotech, Hialeh, Fla.) and viral RNA by real-time amplification (Amara et al., Science 92:69, 2001). Residual viral infectivity was evaluated in each treated aliquot by standard titration on CEM×174 cells and monitoring of p27 production in the supernatant fluids of individual well. The infectious titers were calculated according to the Spearman-Karber method.

Isopycnic Density Gradient Centrifugation

Virus density profiles were evaluated by subjecting them to isopycnic gradient centrifugation. Briefly, 1.3 ml each of 20%-60% sucrose in phosphate buffered saline (PBS) was overplayed, with 8% increments in sucrose concentrations. Six sucrose concentrations were layered, from 60% sucrose at the bottom, to 20% sucrose at the top. Virus samples (prepared after pelleting through a 20% sucrose cushion) in 750 μl PBS were carefully over-layed on top of the 20% sucrose. All tubes were spun in an 80Ti rotor for the Beckman L8 Ultracentrifuge at 40,000 rpm, and at 4° C. for 16 h. Starting from the top, 17 fractions of 525 μl per tube were collected. Virus concentrations were analyzed using a commercial SIV Gag p27 ELISA kit (Coulter, Calif.).

Fast Performance Liquid Chromatography (FPLC) Virus Analysis

Delipidated viruses were further analyzed by FPLC in a Pharmacia FPLC System. Virus samples (200 μl) were injected into a Superose 6 HR 10/30 (Pharmacia, Sweden) column. Sixty fractions of 500 μl each were collected, at a flow rate of 0.4 ml/min in PBS without Ca and Mg. Presence of SIV in the fractions was detected by a p27 ELISA (Coulter, Calif.). Amounts of cholesterol in the virus fractions were analyzed by the Amplex Red Total Cholesterol Assay according to manufacturer's instructions (Molecular Probes, OR).

Immunization of Mice

Four to six-10 week old female Balb/C mice were given a primary immunization with 10 μg of sucrose banded AT-2 inactivated SIVmac251 (ABI, Columbia, Md.) emulsified in Freund's incomplete adjuvant (IFA) and administered subcutaneously (sc). For purposes of control some mice were primed with IFA only. Groups of 6 animals were then administered a booster immunization 2 weeks later using variable doses of treated vs. non treated SIVmac251 intravenously. The animals were then sacrificed 4 days post boost to collect blood and splenocytes to perform the immune analyses described below.

Intracellular IFN-γResponse Evaluation of Cell Mediated Responses

These analyses were performed using intracellular cytokine (ICC) analyses following short-term antigen specific restimulation in the presence of 5 μg/mL of Brefeldin A and 1 μg/ml each of anti-mouse CD28 and CD49d monoclonal antibodies followed by evaluation of the frequencies of IFN-γ producing $CD4^+$ and $CD8^+$ T-cells. The standard protocol consisted of a 12 h re-stimulation of $1\times10^6$ splenocytes with pools of peptides (containing 2 μg/ml of each individual peptide) encompassing the entire SIV gag (16 peptide pools, 20-mers overlapping by 12 residues) and SIV env (17 peptide pools, 25-mers overlapping by 13 residues), each pool containing 7-9 peptides. Positive control samples consisted of splenocytes stimulated with the mitogens PMA/ionomycin and PHA; negative controls are no peptide stimulation and stimulation with the ovalbumin specific peptide SYNFEKL (SEQ ID NO: 136). The cultures were carried out for 2 hours before adding the Brefeldin A designed to prevent excretion of the cytokine and promote its intracellular accumulation. The restimulated splenocytes were then stained for $CD4^+$, $CD8^+$ and intracellular for IFN-γ. Evaluation of frequencies of IFN-γ positive $CD4^+$ and $CD8^+$ T-cells were analyzed by counting about 200,000 events/sample using a FACS Calibur (Beckton Dickinson, Mountain View, Calif.).

Serology

SIV EIA: Serum samples were titered for antibodies to viral epitopes using routine EIA and Western Blot analysis. Briefly, poly-L-Lysine (10 μg per ml of PBS) coated ELISA micro plates were adsorbed 2 μg purified SIVmac251/well overnight in standard bicarbonate coating buffer, pH 9.6 at 4° C. Following 3 washes with PBS/Tween 20, the plates were blocked for 1 h at room temperature with PBS containing 2% non-fat dry milk. Sequential two-fold serum dilutions were then added to the plate as well as positive and negative control samples in duplicates and incubated at 37° C. for 2 h. After washing the unbound antibodies, the plates were incubated for 1 h at 37° C. with an alkaline phosphatase-anti mouse IgG conjugate (Southern Biotech, Birmingham, Ala.), and later developed with p-nitrophenylphosphate (BioRad) at room temperature. The plates were read at a 450 nm wavelength using an ELISA reader (Molecular Devices, Sunnyvale, Calif.). SIV Western blots: For Western blot analysis, commercially available SIV western blot kits (Zeptometrix, Buffalo, N.Y.) were utilized against mouse sera diluted 1:100 and developed according to the manufacturer's instructions.

Results

Viral Delipidation Results in Removal of Cholesterol Without Loss of Viral Proteins Our previous optimization procedures led to the finding that DIPE treatment effectively delipidated HIV without significant loss of viral proteins (data not shown). We extended these findings to evaluate whether this method could delipidate SIV-mac251. SIV-mac251 was delipidated using DIPE without significantly affecting total protein or viral proteins (p27). Recoveries of both total viral protein and viral gag p27 were not significantly different when compared to live SIV. These findings were confirmed by silver staining and Western blot analysis of SIV. Delipidated virus showed a reproducible 2 log reduction in infectivity (FIG. 7). Removing cholesterol from virus using our method reduces infectivity in a similar manner to β-CD removal of cholesterol in HIV-1 (Nguyan et al., J. Immunol. 168:4121, 2002; Graham et al., J. Virol. 77:8237, 2003), without losing viral RNA or viral proteins. To further characterize the loss of lipids to the physical properties of the treated virus, we evaluated the virus particle profiles by fast performance liquid chromatography (FPLC) (FIG. 5). The FPLC profiles of the control and aldrithiol-2 (AT-2) treated viruses were similar (data not shown). However, DIPE treated virions changed their structural profile, compared to the live control virions. To evaluate whether our delipidation procedure led to removal of cholesterol, we analyzed treated viruses for cholesterol using the Amplex Red assay following FPLC separation. The DIPE treated viruses had approximately 80% less cholesterol than the control virus when expressed as cholesterol/gag p27 protein ratio. Viruses were further analyzed by isopycnic density gradient centrifugation, to evaluate particle densities. Delipidation changed the buoyancy of the virions, resulting in a shift of the density range of viral particles (FIG. 4).

Delipidated Viruses are Able to Elicit Broader Cell-mediated Immune Responses During Boosting To evaluate whether the delipidated viruses had enhanced immunogenicity in boosting cell mediated immune responses, we boosted mice primed with AT-2 inactivated SIV (Rossio et al., J. Virol. 72: 7992, 1998; Arthur et al., AIDS Res. Human Retroviruses 14:Suppl. 3. S311, 1998) with control and delipidated virus. After two weeks, immunized mice groups (6 mice per group) were boosted with 1 μg total viral protein of either live SIV, AT-2 inactivated SIV, or DIPE delipidated SIV. T-cell responses were evaluated using SIV Gag and SIV gp120 envelope overlapping peptide pools, and responding cells detected by intracellular interferon-γ (IFN-γ) flow cytometry (ICC). DIPE delipidated virus booster elicited broader $CD4^+$ and $CD8^+$ responses, compared to control or AT-2 groups (FIGS. 8A and 8B). Specific IFN-γ peptides were also determined from the peptide pool grids, yielding similar patterns to those seen when analyzing the peptide pools. DIPE treated SIV also elicited new peptide pool recognition patterns, compared to the other groups (Table 9). The data were especially striking for $CD4^+$ responses to env peptide pools. DIPE group had a statistically significant increase in responses compared to the live SIV boosted group ($p=0.006$), and to the AT-2-treated SIV boosted group ($p=0.0001$). Similar trends were observed with the DIPE treated SIV for $CD8^+$ env peptide pool responses ($p=0.001$ relative to live and $p=0.02$ relative to AT-2 group). $CD4^+$ gag responses were significantly increased as well ($p=0.03$ relative to AT-2 group). The DIPE treated SIV boosted group also had more IFN-γ positive cells than the other two groups. Antigen dosage studies indicated that a surprisingly low dose of 1 μg of DIPE delipidated virus (which corresponds to approximately 200 ng of SIV p27) was sufficient to elicit broad $CD4^+$ and $CD8^+$ immune responses to both gag and env. Broad $CD4^+$ and $CD8^+$ responses to env and gag peptide pools were observed in mice boosted with delipidated virus when compared to AT-2 treated or live virus boost ($p>0.001$).

Predominantly $CD4^+$ T cell responses were observed at antigen doses as low as 0.05 ug of delipidated virus administered IV without adjuvant, whereas higher doses were needed for AT-2 or live SIV protein. Preliminary antibody responses indicate that the delipidated virus is stimulating antibody responses as well. These findings show a $CD4^+$ and $CD8^+$ cellular responses to a broad array of SIV antigens elicited by very low boost concentrations of virus delipidated with the method of the present invention.

In the following few paragraphs a response is operationally defined as a CD4 cellular response to SIV env peptides in terms of a percentage of CD4+ cells that are positive for interferon gamma. Peptide pools that elicited responses, and several ranges of responses (percentage of CD4+ cells that are positive for interferon gamma) are indicated.

The CD4 cellular response to SIV env peptides was not significant in mice treated with 5 ug of live virus. Following administration of various amounts of 1% DIPE delipidated virus, a CD4 cellular response to SIV env peptides was observed. At a dose of 0.05 ug, a response was elicited from three env peptide pools 5 (0.13-0.22%), 6 (−0.3-0.13%) and 13 (0.13-0.22%). At a dose of 1.0 ug, a broad response was elicited from over several env peptide pools (3, 4, 5 (0.06-0.23%), 8, 11, 12 (0.19-0.45%), 13 (0.13-0.39%), 14 (0.13-0.34%), 15 (−0.03-0.24%)). At the higher dose of 5 ug, a response was observed to env peptide pool 5 (0.17-0.23%).

The CD4 cellular response to SIV env peptide to boost with various amounts of AT-2 treated virus revealed limited response. At a dose of 0.05 ug, a response was elicited from one env peptide pool (10 (0.17-0.25%)). At a dose of 1.0 ug, a response was elicited from about one env peptide pool (10 (0.08-0.22%)). At the higher dose of 5 ug, the CD4 cellular response was not significant.

The CD4 cellular response to SIV env peptide to boost with various amounts of live SIV virus showed a response at a dose of 0.05 ug from pools 1 (−0.05-0.23%), 8 (0.13-0.21%), 12 (0.11-0.21%) and 14 (−0.03-0.25%). At a dose of 1.0 ug, a response was elicited from three env peptide pools (8 (0.22-0.36%), 12 (0.12-0.58%) and 13 (−0.09-0.33%)). At the higher dose of 5 ug, the CD4 cellular response was not significant.

In the following few paragraphs a response is operationally defined as a CD8+ cellular response to SIV env peptides in terms of a percentage of CD8+ cells that are positive for interferon gamma. Peptide pools that elicited responses and several ranges of responses (percentage of CD8+ cells that are positive for interferon gamma) are indicated.

Following administration of various amounts of 1% DIPE delipidated virus, a CD8 cellular response to SIV env peptides was observed. At a dose of 0.05 ug, a response was elicited from two env peptide pools 5 (0.22-1.22%) and 13 (0.43-0.92%). At a dose of 1.0 ug, a broad response was elicited from several env peptide pools (2 (0.18-0.34%), 3 (−0.06-0.35%), 4 (−0.03-0.15%), 5 (0.06-0.25%), 9 (0.24-0.41%), 10 (0.34-0.87%), 11 (0.22-0.71%), 12 (0.19-0.53%), 13 (0.11-0.35%), 14 (0.19-0.32%), 15 (0.98-1.35%) and 16 (0.11-0.31%) At the higher dose of 5 ug, a response was observed to env peptide pool 13 (0.27-0.41%), 14 (0.28-0.48%) and 15 (0.31-0.35%).

Following administration of various amounts of AT-2 treated virus, a limited CD8 cellular response to SIV env peptides was observed. At a dose of 0.05 ug, a CD8 cellular response, was elicited from env peptide pool 16 (0.08-0.45%). At a dose of 1.0 ug, a response was elicited from env peptide pools 7 (0.18-0.33%) and 16 (0.29-0.88%). At the higher dose of 5 ug, the CD8 cellular response was not significant.

Following administration of various amounts of live SIV, a limited CD8 cellular response to SIV env peptides was observed. At a dose of 0.05 ug, a CD8 cellular response, was elicited from peptide pools 1 (−0.05-0.23%), 8 (0.13-0.2%), 12 (0.11-0.21%) and 14 (−0.03-0.25%). At a dose of 1.0 ug, a response was elicited from peptide pools 8 (0.22-0.36%), 12 (0.12-0.58%), and 13 (−0.02-0.33%). At the higher dose of 5 ug, the CD8 cellular response was not significant.

In the following few paragraphs a response is operationally defined as a CD4 cellular response to SIV gag peptides in terms of a percentage of $CD4^+$ cells that are positive for interferon gamma. Peptide pools that elicited responses, and several ranges of responses (percentage of CD4+ cells that are positive for interferon gamma) are indicated.

Following administration of various amounts of 1% DIPE delipidated virus, a CD4 cellular response to SIV gag peptides was observed. At a dose of 0.05 ug, a response was elicited from gag peptide pools 5 (0.22-1.22%) and 13 (0.43-0.92%). At a dose of 1.0 ug, a broad response was elicited from about five gag peptide pools (3 (0.19-0.72%), 5 (0.15-0.71%), 7 (0.12-0.77%), 10 (0.19-0.92%), and 15 (0.42-1.35%)). At the higher dose of 5 ug, the response decreased to about four gag peptide pools 3 (0.12-0.49%), 5 (−0.04-0.48%), 10 (0.11-0.52%), 14 (−0.03-0.52%), and 15 (0.18-0.56%).

Following administration of various amounts of AT-2 treated virus, a limited CD4 cellular response to SIV gag peptides was observed. At a dose of 0.05 ug, a CD4 cellular response, was elicited from three gag peptide pools (10 (0.19-0.59%), 11 (0.11-0.39%), and 13 (−0.03-0.31%)). At a dose of 1.0 ug, a limited response was elicited from gag peptide pool 7 (−0.05-0.27%). At the higher dose of 5 ug, the CD4 cellular response was not significant.

Following administration of various amounts of live SIV virus, a CD4 cellular response to SIV gag peptides was observed. At a dose of 0.05 ug, a CD4 cellular response, was elicited from about 2 gag peptide pools (2 (0.59-1.23%) and 9 (0.34-1.1%)). At a dose of 1.0 ug, a response was elicited from about four gag peptide pools (2 (0.39-1.12%), 3 (0.11-0.51%), 6 (0.21-0.72%), and 9 (0.15-0.51%)). At the higher dose of 5 ug, a response was elicited from about two gag peptide pools (2 (0.16-0.51%) and 6 (−0.05-0.23%)).

In the following few paragraphs a response is operationally defined as a CD8 cellular response to SUV gag peptides in terms of a percentage of CD8+ cells that are positive for interferon gamma. Peptide pools that elicited responses, and several ranges of responses (percentage of CD8+ cells that are positive for interferon gamma) are indicated.

Following administration of various amounts of 1% DIPE delipidated virus, a CD8 cellular response to SIV gag peptides was observed. At a dose of 0.05 ug, a response was elicited from about five gag peptide pools (2 (0.19-0.92%), 3 (0.19-0.94%), 4 (0.18-0.95%), 6 (0.28-0.49%), and 13 (0.29-0.88%)). At a dose of 1.0 ug, a response was elicited from about six gag peptide pools (2 (0.01-1.01%), 3 (0.03-0.49%), 6 (0.01-0.99%), 7 (0.02-0.37%), 10 (0.01-0.92%), and 15 (0.05-0.65%)) At the higher dose of 5 ug, a response was elicited from about seven gag peptide pools (2 (0.11-0.37%), 3 (0.16-0.54%), 4 (0.18-0.91%), 5 (0.18-0.71%), 10 (0.13-0.23%), 14 (0.13-0.81%), and 15 (0.2-0.56%)).

Following administration of various amounts of AT-2 treated virus, a CD8 cellular response to SIV gag peptides was observed. At a dose of 0.05 ug, a CD8 cellular response, was elicited from five gag peptide pools (10 (0.28-0.71%), 11 (0.3-0.91%), 12 (0.23-0.76%), 13 (0.15-0.61%), and 14 (0.19-0.72%)). At a dose of 1.0 ug, a response was elicited from about three gag peptide pools (10 (0.01-0.73%), 11 (−0.02-1.1%), and 12 (−0.05-0.72%)). At the higher dose of 5 ug, a response was elicited from about one gag peptide pool (10 (0.07-0.27%).

Following administration of various amounts of live SIV virus, a CD8 cellular response to SIV gag peptides was observed. At a dose of 0.05 ug, a CD8 cellular response, was elicited from about 3 gag peptide pools (2 (0.28-0.92%), 9 (0.32-0.82%), and 15 (0.21-0.43%)). At a dose of 1.0 ug, a response was elicited from about five gag peptide pools (2 (0.01-0.91%), 3 (0.03-0.67%), 6 (0.01-0.71%), 9 (−0.25-0.8%) and 12-0.05-0.39%)). At the higher dose of 5 ug, a response was elicited from about three gag peptide pools (2 (0.19-0.71%), 9 (0.19-0.53%), and 12 (0.04-0.87%)).

Taken together, these data demonstrate that mice immunized with AT-2 treated SIV virus show enhanced immunological responses to boosting with delipidated SIV virus when compared to boosting with AT-2 treated virus or live SIV virus. The delipidated SIV virus was more immunogenic than the AT-2 treated virus in terms of the percentage of $CD4^+$ and $CD8^+$ with enhanced IFN-γ staining.

Our data indicate that delipidated viruses elicited strong T-cell mediated immune responses, without the use of an adjuvant. Increase in the breadth and strength of the overall cell-mediated immune response was observed in the DIPE boosted mice group, compared to the live and AT-2 treated groups. Tables 9 and 10 present a summary of these results.

TABLE 9

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| | | | | | CD4 ENV POOLS RESPONDING | | | | | | | | | | | | |
| 0.05 μg DIPE | | | | | + | | | | | | | | + | | | | |
| 1 μg DIPE | | | | | ▓ | | | | | | | ▓ | ▓ | ▓ | ▓ | | |
| 5 μg DIPE | | | | | + | | | | | | | | | | | | |
| | | | | | CD8 ENV POOLS RESPONDING | | | | | | | | | | | | |
| 0.05 μg DIPE | | | | | + | | | | | | | | + | | | | |
| 1 μg DIPE | ▓ | ▓ | | | ▓ | | | | | ▓ | ▓ | ▓ | ▓ | ▓ | ▓ | ▓ | ▓ |

TABLE 9-continued

| 5 µg DIPE | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
|  |  |  |  |  |  | + |  |  |  |  |  | + | + | + |  |  |

CD4 GAG POOLS RESPONDING

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 0.05 µg DIPE |  |  |  |  |  | + |  |  |  |  |  | + |  |  |  |  |
| 1 µg DIPE |  |  | ▨ |  |  | ▨ |  | ▨ |  |  | ▨ |  |  |  | ▨ |  |
| 5 µg DIPE |  |  |  | + |  | + |  |  |  | + |  |  | + |  |  |  |

CD8 GAG POOLS RESPONDING

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 0.05 µg DIPE |  | + | + | + |  | + |  |  |  |  |  | + |  |  |  |  |
| 1 µg DIPE |  | ▨ | ▨ |  |  | ▨ | ▨ |  |  | ▨ |  | ▨ |  |  | ▨ |  |
| 5 µg DIPE |  | + | + | + | + |  |  |  |  | + | + | + |  | + | + |  |

SIV gag and env peptide pool responses for CD4$^+$ and CD8$^+$ T-cells in mice boosted with 0.05, 1, or 5 µg total protein.
1 million mouse PBMCs were stimulated with different peptide pools as indicated, for 2 h.
After blocking protein secretion by Brefeldin A, anti-CD4 and anti-CD8 antibodies were added, cells permeabilized and further stained with anti-IFN-γ Ab.
Cells were subsequently analyzed by FACS.
Any responses above 0.1% of total cells positive for IFN-γ staining were considered as a positive response.
Shaded symbols represent DIPE treated viruses at 1 µg dose.

TABLE 10

TABLE 10. Mice were immunized with 10 µg of SIV incorporated in Freund's incomplete adjuvant sc and 2 weeks later boosted iv with varying concentration of DIPE treated SIV, AT-2 treated SIV or untreated live SIV. Controls consisted of groups of mice primed with saline but boosted with DIPE, AT-2 or untreated virus or groups of mice primed with SIV but boosted with saline. Spleen cells were assayed for response to pools of SIV env or SIV gag overlapping peptides utilizing the ICC assay for CD4$^+$ or CD8$^+$ T-cells synthesizing IFN-g, and denotes a net response (response to media and irrelevant peptide was deducted) to the appropriate peptide pool.

CD4 ENV POOLS RESPONDING

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1% DIPE |  |  |  |  | ⊞ |  |  |  |  |  |  | + | ⊞ | ⊞ | ⊞ |  |  |
| LIVE |  |  |  |  |  |  |  | ⊞ |  |  |  | + |  |  |  |  |  |
| AT-2 |  |  |  |  |  |  |  |  |  | ⊞ |  |  |  |  |  |  |  |
| CONTROLS | | | | | | | No detectable responses | | | | | | | | | | |

CD8 ENV POOLS RESPONDING

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1% DIPE |  | ⊞ | ⊞ |  |  |  |  | + | ⊞ | ⊞ | ⊞ | + | ⊞ | ⊞ | ⊞ | + |  |
| LIVE |  |  |  |  |  |  |  |  | + |  |  | + |  |  |  |  |  |
| AT-2 |  |  |  |  |  |  | ⊞ |  |  |  |  |  |  |  |  | + |  |
| CONTROLS | | | | | | | No detectable responses | | | | | | | | | | |

CD4 GAG POOLS RESPONDING

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1% DIPE |  |  |  | + |  | ⊞ |  | ⊞ |  |  | ⊞ |  |  |  | ⊞ |  |
| LIVE |  |  | ⊞ | + |  |  | + |  |  |  |  |  |  |  |  |  |
| AT-2 |  |  |  |  |  |  |  |  |  |  |  |  |  |  |  |  |
| CONTROLS | | | | | | No detectable responses | | | | | | | | | | |

CD8 GAG POOLS RESPONDING

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1% DIPE |  |  | + | + |  | + | ⊞ |  | + |  |  |  |  | + |  |  |
| LIVE |  |  | + | + |  | + |  | ⊞ |  | + |  |  |  |  |  |  |
| AT-2 |  |  |  |  |  |  |  |  |  | + | ⊞ | + |  |  |  |  |
| CONTROLS | | | | | | No detectable responses | | | | | | | | | | |

Antibody Titers are Enhanced in DIPE Treated SIV Boosted Group

Figure 9:
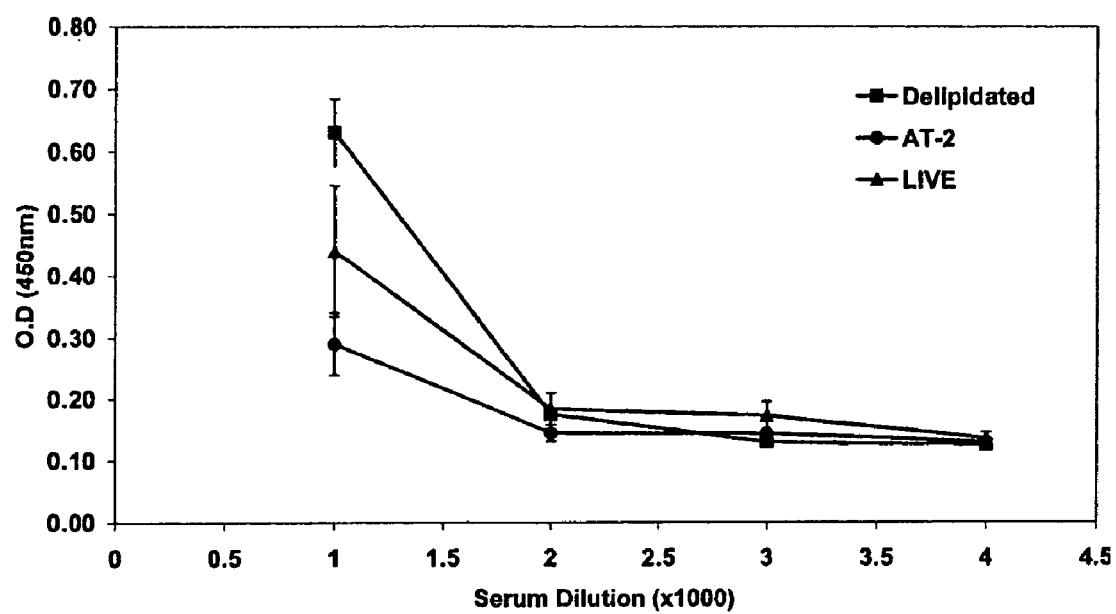
FIG. 9 is a schematic representation of SIV env gp120 antibody titers (O.D. at 450 nm) in mice immunized with AT-2 treated virus (SIV mac 251) and boosted with 1 ug total viral protein of live virus (SIV mac 251), AT-2 inactivated virus or delipidated virus (1% DIPE). Serial dilution of mouse plasma was measured in ELISA plates coated with recombinant SIV mac251 gp120 env protein.
Figure 10:
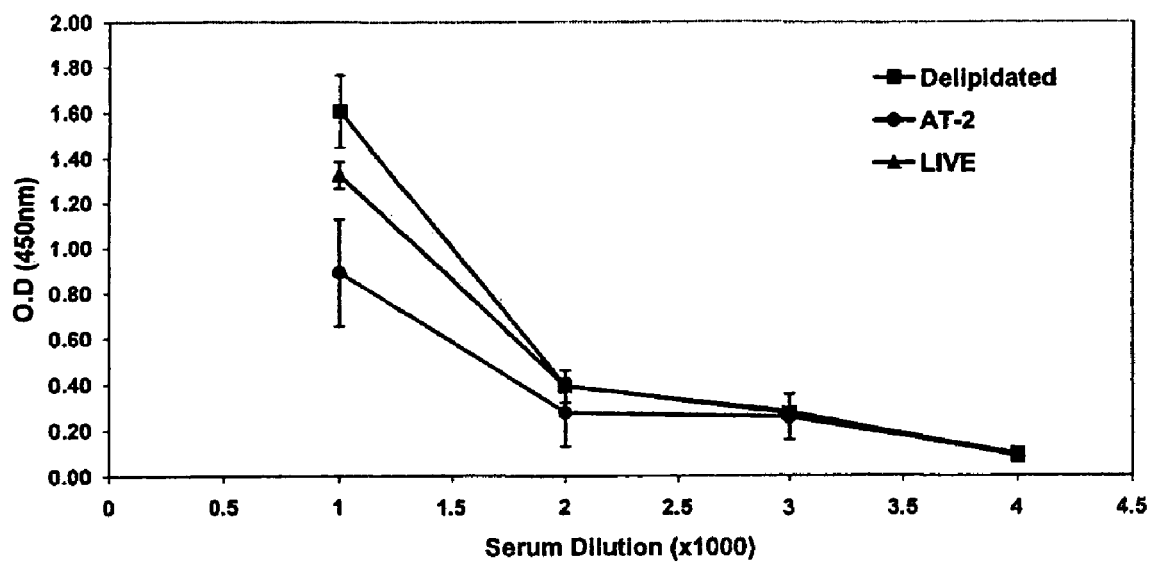
FIG. 10 is a schematic representation of SIV gag p55 antibody titers (O.D. at 450 nm) in mice immunized with AT-2 treated virus and boosted with 1 ug total viral protein of live virus (SUV mac 251), AT-2 inactivated virus or delipidated virus (1% DIPE). Serial dilution of mouse plasma was measured in ELISA plates coated with recombinant SUV mac251 p55 gag protein.

Antibody (Ab) titers to whole virions were determined for each group. Antibody titers to SIV gp120 were significantly lower in the AT-2 boosted group compared to the DIPE boosted groups (p=0.02) (FIG. 9). In general, DIPE boosted mice gave higher Ab readings, compared to either the live, or AT-2 boosted groups, for both SIV gp120 and SIV Gag (FIG. 10). When Ab titers were measured in a subsequent experiment at 4 weeks, boosting was observed for all groups (data not shown). Gag (p55) antibody titers, measured by ELISA (absorbance at 450 nm), were higher in serum from mice boosted with delipidated SIVmac251 than either live or AT-2 treated SIV boosted groups. Western Blot analysis supported the antibody ELISA data, as a broader p27 band was observed by the delipidated SIV boosted serum, compared to live or AT-2 treated mouse serum. This indicates a broader p27 epitope recognition by gag antibodies from the delipidated SUV boosted mice. Maturation of antibody response to both gag and env was observed when mice were boosted 4 weeks after priming compared to a 2 week boosting post prime. Route of administration, subcutaneous (sc) or intravenous (IV), did not affect antibody (ELISA) titers. A stronger correlation is seen between $CD4^+$ T-cell and antibody responses to both SIVmac251 gag and env proteins in mice boosted with delipidated virus compared to live or AT-2 treated virus boosts.

Strong Correlation Between CD4 Responses and Antibody Responses

Figure 11:
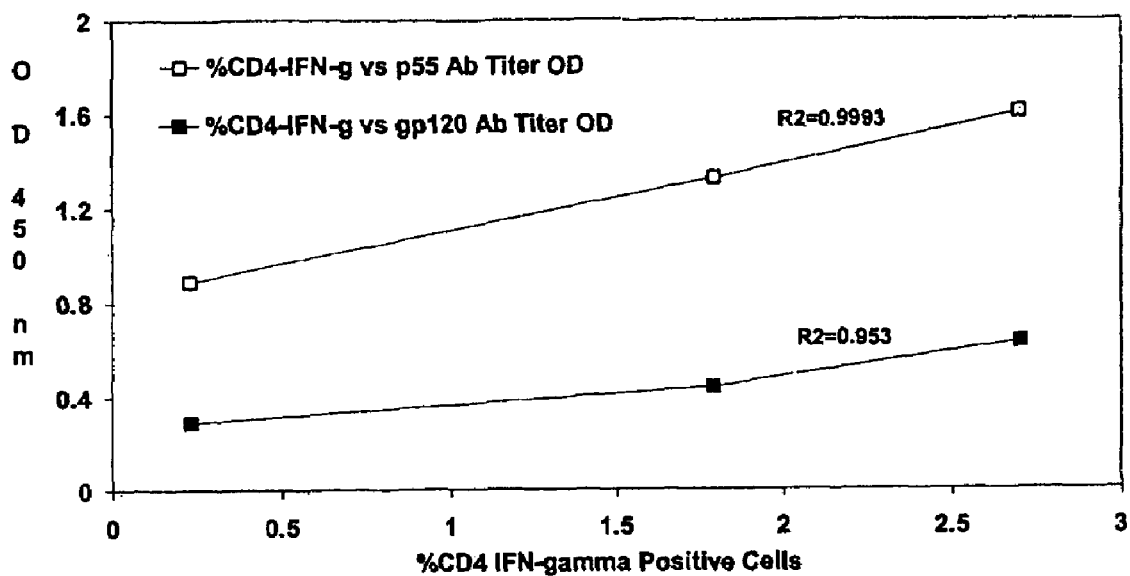
FIG. 11 is a schematic representation of a correlation curve of CD4+ responses (% IFN gamma cells) to SIV mac 251 Gag and Env peptide pools to the antibody responses (O.D. 450 nm) to recombinant Gag and Env. A strong correlation ($R^2$=0.9993) was observed between the cellular responses (CD4) to SIV mac 251 gag and the anti-gag antibody responses. A good correlation ($R^2$=0.953) was observed between cellular responses (CD4+) to SIV mac 251 env and the anti-env antibody responses.

We further determined the impact of immunization by comparing the $CD4^+$ responses to gag and env peptide pools to the antibody responses to recombinant gag and env. A strong correlation was observed between the cellular responses (CD4) and the humoral responses (antibody responses) (FIG. 11), indicating additional benefits of enhanced cell mediated immune responses.

DIPE-treatment created a powerful cell mediated immune response, and a good humoral response in the absence of an adjuvant. Significantly, an effective boosting was achieved with as little as 1 mg total viral protein of DIPE treated SIV, representing about 200 ng of SIV p27.

Our ability to elicit virus peptide specific immune responses with as little as 1 μg of total virus protein was both surprising and unexpected. This level of immune response achieved with a single IV boost without co-administration of adjuvants suggests that the biochemical nature of delipidated virus is sufficiently altered to direct an efficient processing and presentation, or recognition of a larger number of viral peptides different from those elicited by live or AT-2-treated SIV.

In conclusion, we have compared the immunogenicity of live SIV, AT-2 treated SIV, and delipidated SIV (DIPE) in Balb/c mice, and observed a significant enhancement of cell-mediated immune responses from the groups boosted with DIPE treated viruses. Surprisingly, effective boosting was achieved with a very low dose of 1 μg total viral protein, which corresponds to about 200 ng of SIV p27. These results were obtained without the use of adjuvants in the boost doses, indicating a substantial increase in immunogenicity. Our results show that delipidating viruses enhanced the antigenicity of the virus, while significantly reducing its infectivity. Our results differ from previous findings that cholesterol-depletion of HIV dramatically reduces virus infectivity (Nguyan et al., J. Immunol. 168:4121, 2002; Graham et al., J. Virol. 77:8237, 2003; Liao et al., AIDS Res. Human Retroviruses 19:675, 2003), because β-CD treated viruses resulted in dramatic loss of viral RNA and viral proteins, thus contributing to the loss of infectivity. Delipidated viruses have negligible loss of viral RNA and viral proteins.

While not wanting to be bound by the following statement, it is believed that the delipidation process may create virus particles which are better processed or presented by antigen presenting cells, leading to the broad peptide pool responses observed. Additionally, delipidation of viruses could expose more cellular antigens (picked up by the virus when budding from infected CEM×174 cells) such as MHC II molecules, which could act as adjuvants in enhancing cellular responses. Serum Ab titers and Western blot analysis of Ab sera profiles, indicated enhanced anti-Env antibodies, and consistent broadening of SIV gag specific antibody responses in DIPE-treated SIV-boosted groups, perhaps indicating an increase in anti-p27 Ab titers, or an increase in Ab avidity to viral proteins. The present results demonstrate that DIPE delipidation of SIV affects the immunogenicity of the virus in mice. It is believed that this novel delipidation method will contribute to HIV therapeutic vaccine design and development.

EXAMPLE 8

Total Protein and p24 Protein Recovery in HIV Virus Treated with Various Delipidation Procedures The applicants have found that the aforementioned delipidation processes are capable of producing intact viral particles, as measured by the degree of total protein recovery and p24 protein recovery.

The sample containing the HIV virus was mixed with solvent using end-over-end rotation at room temperature for 20 minutes at a speed of 70%. Next the sample was centrifuged for 2 minutes at 1000×g and then passed through a charcoal column. Total protein was measured by BioRad Assay. Viral p24 was measured by p24 sandwich ELISA (Coulter) Total protein recovery for delipidation processes using 1% DIPE, 1% butanol/DIPE, 1% butanol, 2% butanol, and 5% butanol are within 10% of the control, specifically in the range of 63% to 75% of total input. P24 protein recovery for delipidation processes using 1% DIPE, 1% butanol/DIPE, 1% butanol, 2% butanol, and 5% butanol are within 40% of the control, with 2% butanol yielding a p24 protein recovery percentage of around 78% relative to a control recovery percentage of around 83%.

EXAMPLE 9

Buoyant Density and Immunoreactivity (gp120 and p24) Profile of HIV and SIV Particles Treated with Various Delipidation Procedures The aforementioned delipidation processes modified the buoyant density of viral particles. Changes in density are useful indicators of successful delipidation because the removal of lipids from viral particles changes the protein to lipid ratio and, as a result, the particle density. In this experiment, the isopyknic densities of control and solvent treated HIV and SIV particles were determined and the changes in density were correlated with measured lipid content of control and treated viruses.

Figure 2:
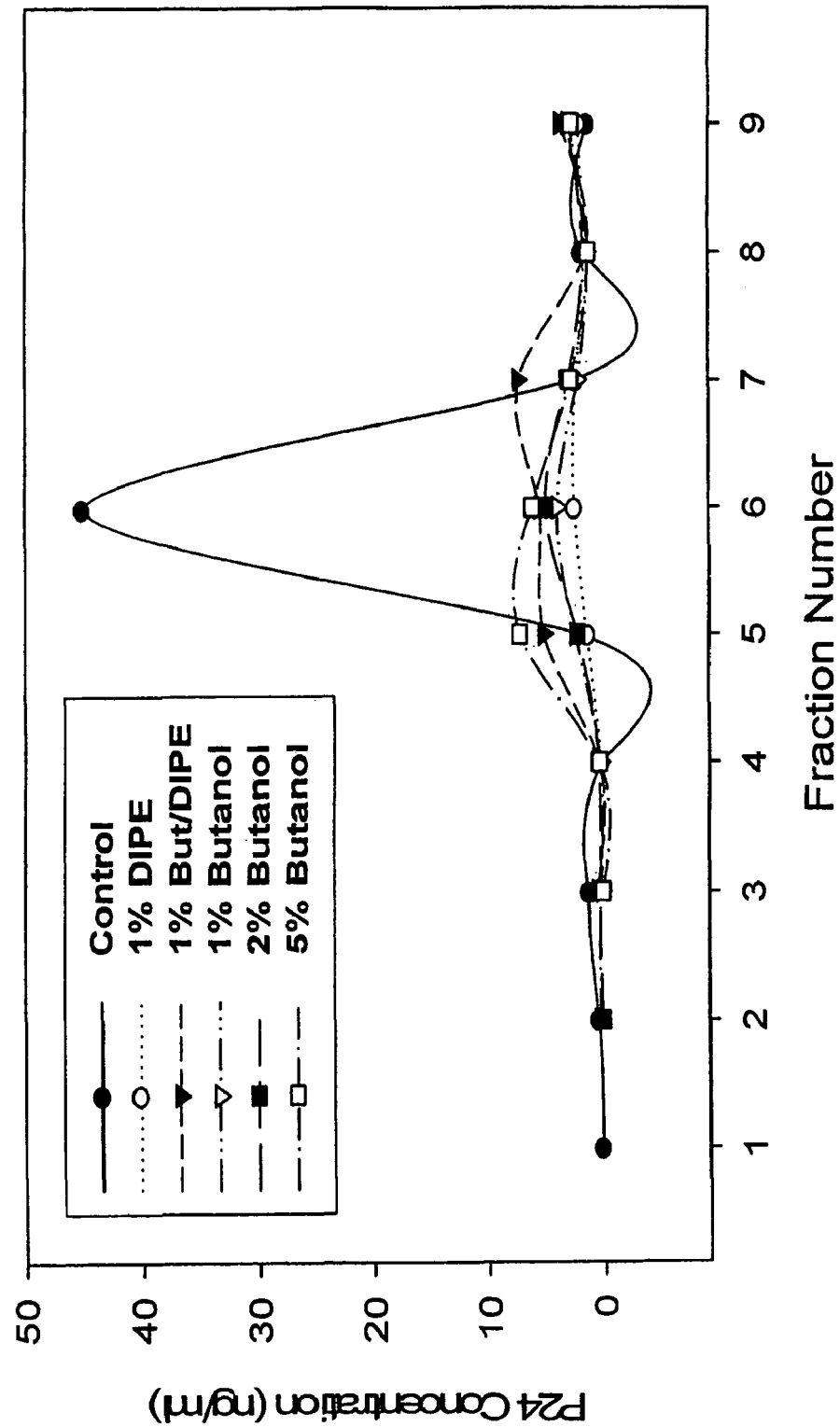
FIG. 2 depicts the p24 protein concentration (ng/ml) for each of the fraction numbers shown in FIG. 1.

Solvent treatments broadened the density range of HIV and SIV particles and high solvent concentrations shifted the virus to higher overall density, based on Western blot analyses and protein profiles, which is consistent with the loss of lipids. Specifically, FIG. 1 depicts the density of sucrose gradient fractions as indicated by the graphing of density against fraction number for viral particles subjected to delipidation using 1% DIPE, 1% butanol/DIPE, 1% butanol, 2% butanol, and 5% butanol, along with a control group. HIV was delipidated and sucrose purified. Virus was loaded onto sucrose gradients and centrifuged until equilibrium densities were reached. FIG. 2 depicts the p24 protein concentration for each of the fraction numbers. As expected, the protein concentration for the control group was highest with 1% butanol/DIPE demonstrating a relatively larger concentration of p24, although registering at a higher density than the control. Other density modified p24 concentrations were exhibited for 5% butanol, 2% butanol, 1% butanol, and 1% DIPE. The density modifications demonstrate a degree of success in delipidating the viral particles.

The HIV-1 virus was run on a sucrose gradient and various fractions were collected and then run on an SDS-PAGE gel, transferred to a membrane, and blotted using a positive control sera from an HIV-1 infected individual.

Western blot analyses were conducted with antibodies for envelope protein gp120 and capsid protein p24 for the various density fractions derived for each of the delipidation processes and the control for HIV-1 viral particles. The Western blot analysis of control samples revealed strong bands of p24 protein and gp120 protein at the expected density fractions. The majority of intact virions eluted in fractions 5-7. The various delipidation processes produced changes in the location of the p24 and gp120 immunoreactive fractions, indicating alterations in the density of the treated viral particles. Treatment of HIV-1 with 1% DIPE produced a shift of immunoreactive bands to higher density fractions. Treatment of HIV-1 with 1% DIPE/butanol and separately with 1% butanol also produced a shift of immunoreactive bands to higher density fractions. Treatment of HIV-1 with 2% butanol resulted in a loss of many proteins, including a decrease in p24 protein and gp120 protein, and an increase in density of the viral particles. Treatment of HIV-1 with 5% butanol resulted in an almost complete loss of p24 protein and gp120 protein immunoreactivity, and a marked increase in density of the viral particles.

Figure 3:
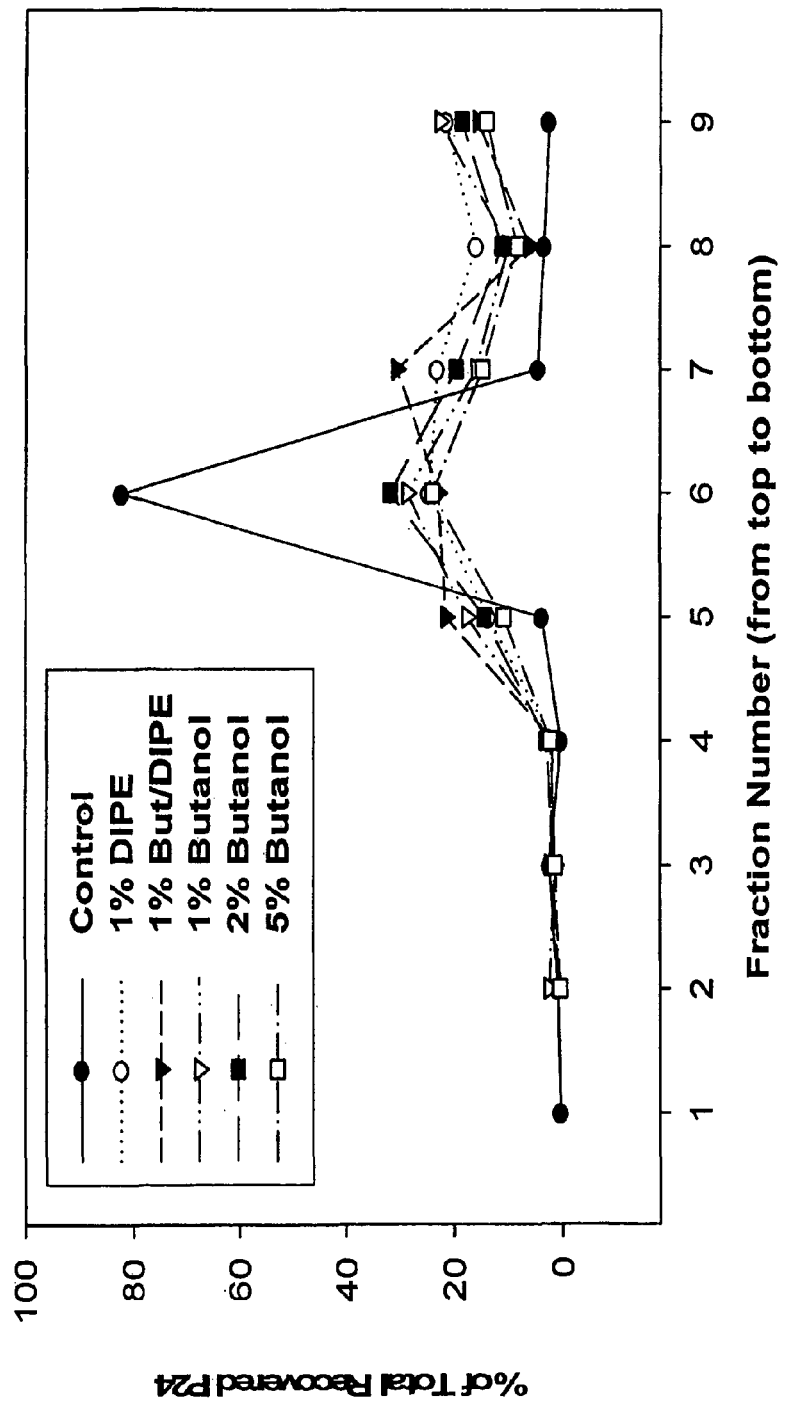
FIG. 3 is similar to FIG. 2 and is a schematic representation of an isopycnic gradient analysis of delipidated HIV subjected to delipidation using 1% DIPE, 1% butanol/DIPE, 1% butanol, 2% butanol, and 5% butanol, along with a control group, indicated by a graphing p24 levels as a percent of total recovered p24 protein against fraction number.
Figure 4:
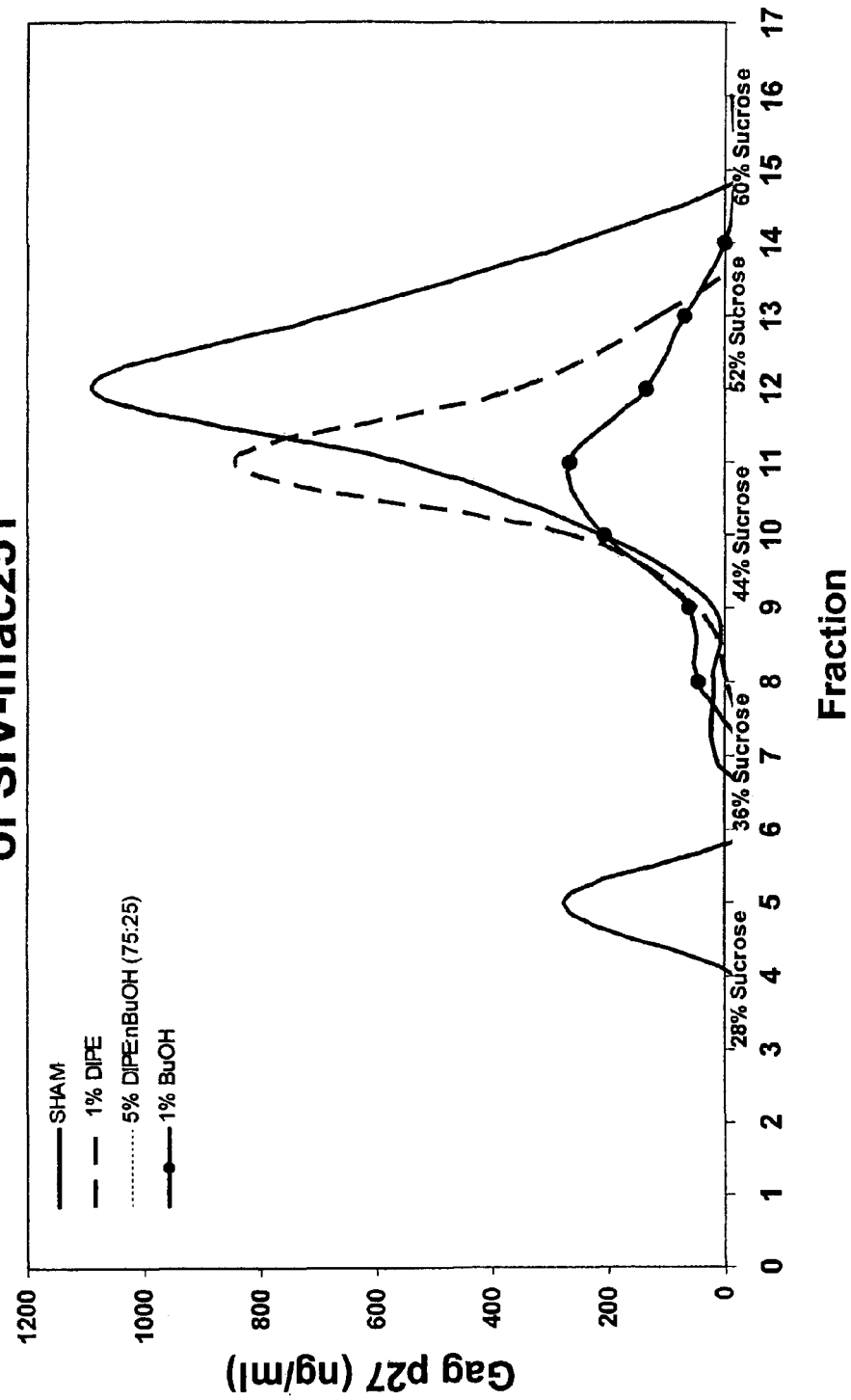
FIG. 4 is a schematic representation of an isopycnic gradient analysis of delipidated SIV-mac 251, indicated by a graphic of gag p27 concentration (ng/ml) against fraction number following delipidation conditions 1% DIPE, 5% DIPE:n-butanol (75:25) and 1% n-butanol.

In FIG. 3, an isopycnic gradient analysis of delipidated HIV, indicated by a graphing of percent of total recovered p24 protein against fraction number, is shown. A substantial amount of the total recovered p24 protein for the samples subjected to delipidation processes is found at higher densities. For each of the samples delipidated with 1% DIPE, 1% butanol/DIPE, 1% butanol, 2% butanol, and 5% butanol, greater amounts of p24 protein were recovered at the higher fraction numbers (higher densities) as compared to the control group. That density shift is further shown in FIG. 4 where the isopycnic density of SIV-mac 251, indicated by a graphic of gag p27 concentration against fraction number, is depicted. Relative to a control, the delipidation samples for 1% DIPE and 1% butanol both exhibited a shift in density.

EXAMPLE 10

Reduction in Cholesterol Content of HIV and SIV Viral Particles Subject to Delipidation Procedures The applicants have found that the aforementioned delipidation processes modify the degree of cholesterol in viral particles. Changes in cholesterol are useful indicators of successful delipidation because the removal of lipids from viral particles changes the amount of cholesterol and the cholesterol to protein ratio. Exposure of HIV and SIV particles to organic solvents removes lipids while preserving proteins, thereby resulting in loss of viral infectivity while maintaining or enhancing the immunogenicity of particles.

In Table 11 the cholesterol to total protein ratio of viral particles delipidated by 1% DIPE, 1% butanol, 1% butanol/DIPE, 2% butanol, and 5% butanol, along with a control, is shown. HIV was delipidated and purified on 20% sucrose. Cholesterol was measured with Amplex Red assay, a commercially available bioassay from vendors such as Molecular Probes, Inc., and total protein was measured. The data shows a decreased cholesterol content, relative to total protein, for each of the delipidated samples.

TABLE 11

Cholesterol and protein levels in HIV subject to different lipid removing solvents

|  | Chol. (µg/ml) | SD (ug/ml) | % of Control | Protein (ug/ml) | Chol./ protein |
| --- | --- | --- | --- | --- | --- |
| Control | 11.06 | 0.31 | 100.00 | 75.45 | 0.15 |
| 1% DIPE | 6.49 | 0.06 | 49.15 | 90.03 | 0.07 |
| 1% But/DIPE | 5.87 | 0.44 | 48.14 | 83.18 | 0.07 |
| 1% Butanol | 5.52 | 0.60 | 45.90 | 82.08 | 0.06 |
| 2% Butanol | 5.14 | 0.16 | 43.54 | 80.53 | 0.06 |
| 5% Butanol | 3.86 | 0.07 | 35.08 | 75.01 | 0.05 |

Figure 5:
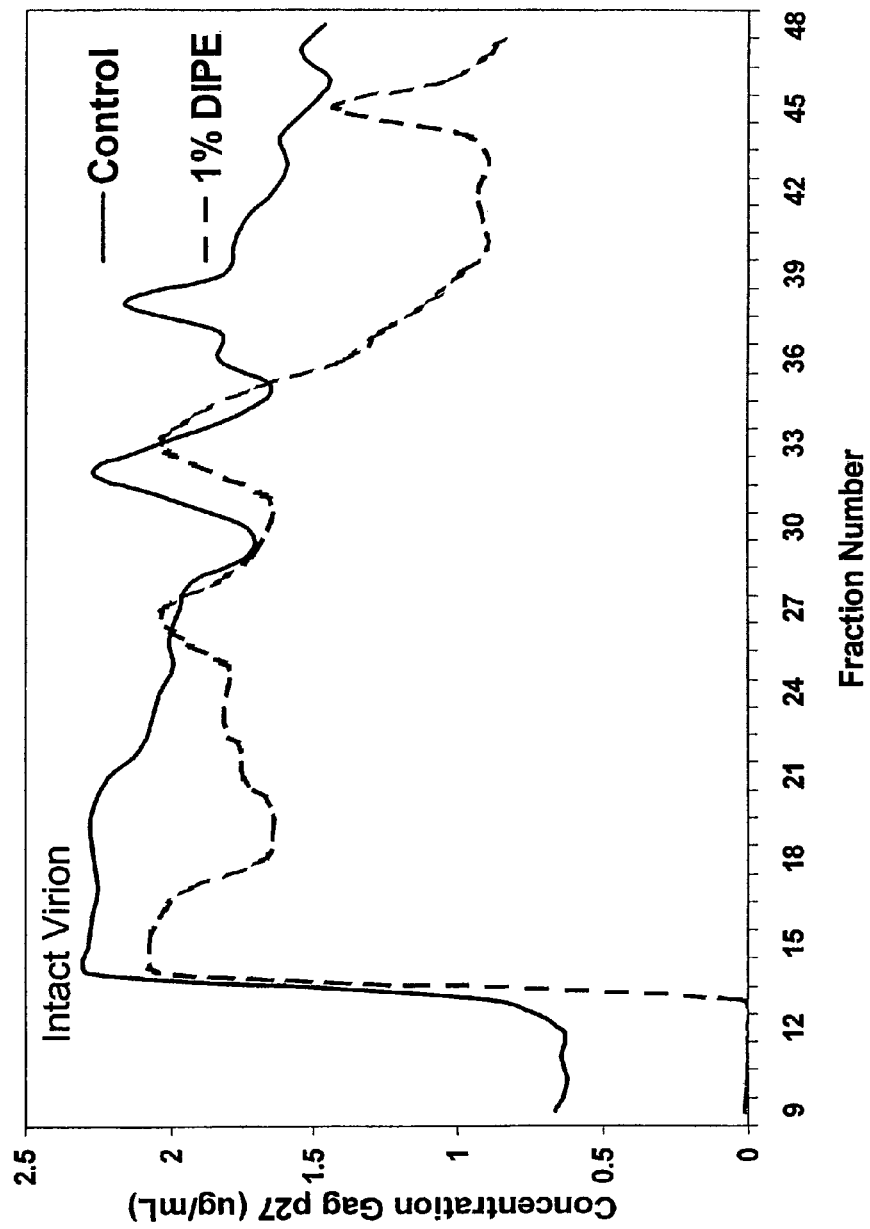
FIG. 5 is a schematic representation of a fast performance liquid chromatography (FPLC) of the control and 1% DIPE-treated SIV mac 521 showing the p27 gag levels (ug/ml) in each fraction number.
Figure 6:
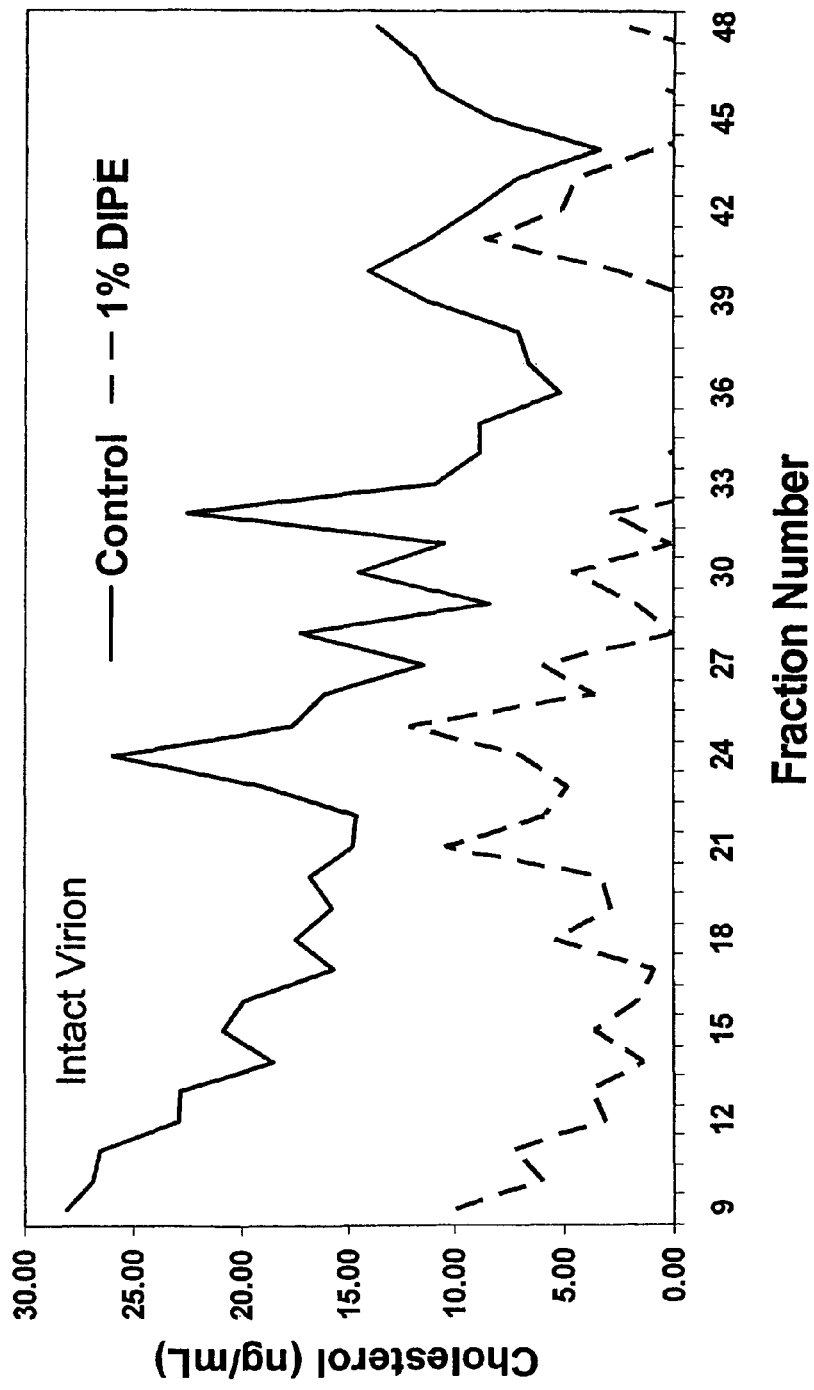
FIG. 6 presents cholesterol levels (ng/ml) in the fractions shown in FIG. 5.
Figure 7:
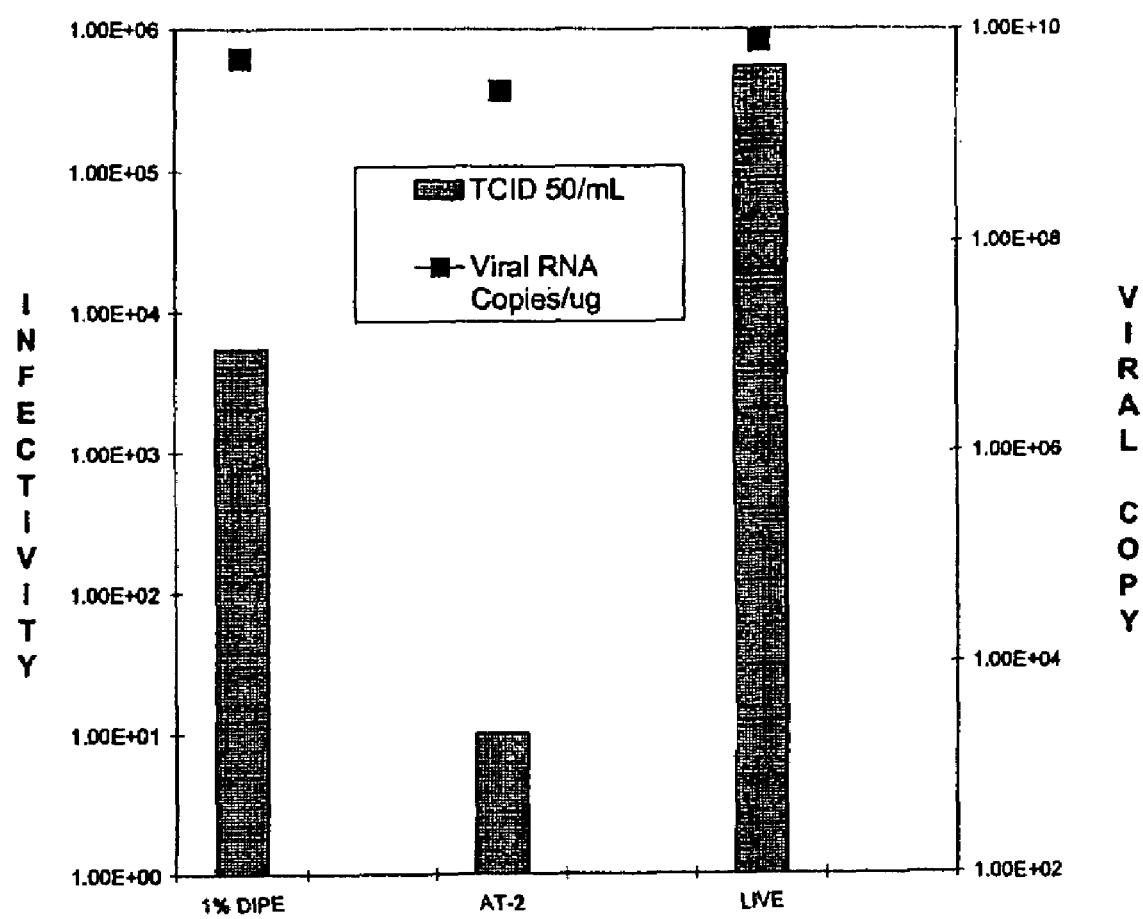
FIG. 7 is a schematic representation of SIV mac 521 infectivity (TCID 50/ml) versus viral RNA copy numbers (copies/mg) after 1% DIPE treatment, in live virus, and after AT-2 treatment.
Figure 8A:
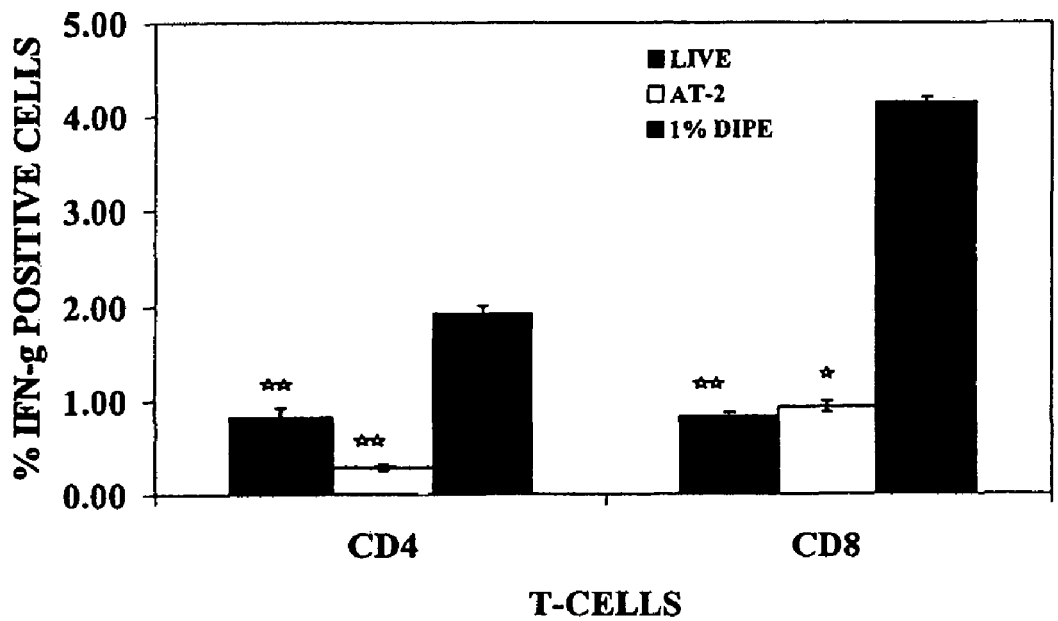
FIGS. 8A and 8B show CD4+ and CD8+ T cell responses (% interferon gamma positive cells) to SIV env (8A) peptide pools and to SIV gag (8B) peptide pools in 1 million PMBCs from AT-2 inactivated SIV primed mice boosted with live virus, AT-2 inactivated virus or delipidated virus (1% DIPE). Mean of 6 mice+or−SEM are shown. **=p value<0.01, *=pvalue<0.05.
Figure 8B:
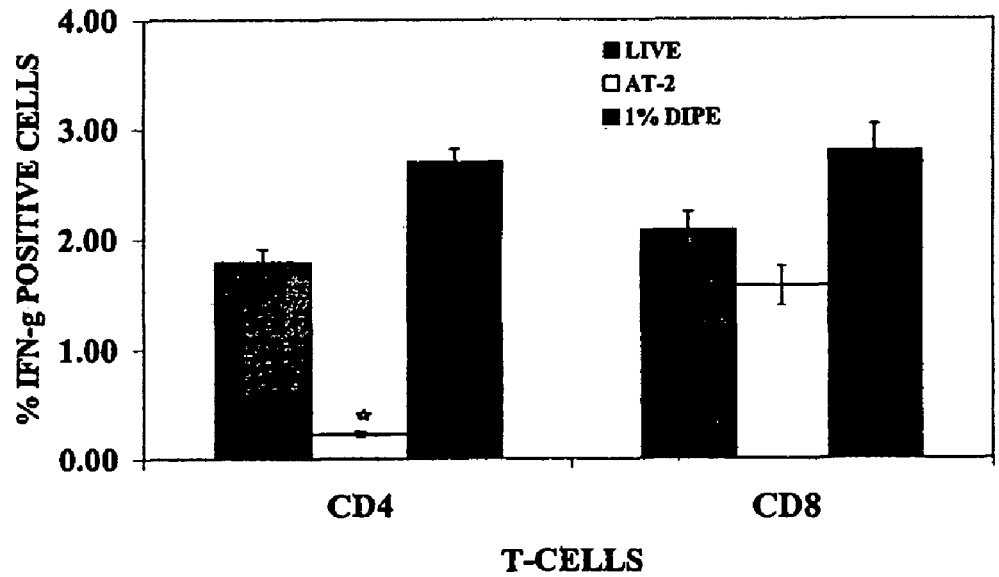

SIV was delipidated and purified on 20% sucrose. Cholesterol was measured with Amplex Red assay and Gag p27 protein measured. Data is expressed as cholesterol to Gag p27 protein ratio. DIPE treated virus had 80% less cholesterol than control, indicating effective delipidation. Similarly, relative to the control, the 1% DIPE sample has a decreased cholesterol to protein ratio. 1% DIPE treatment effectively removed 80% cholesterol while maintaining the structural integrity of the virus measured by the p27 recovery. 5% DIPE:n-butanol treatment led to a dramatic loss of viral protein, total protein, and cholesterol. This method was too harsh. 1% butanol treatment was not effective at delipidating the virus, as the amount of cholesterol measured was still intact. The recovery of total cholesterol is about 37% and 78% for 1% butanol and 1% DIPE, respectively, and the corresponding recovery of p27 protein is about 90% and 15%, respectively, further indicating a successful delipidation of viral particles while still keeping a substantial portion of such viral particles intact. Referring to FIGS. 5 and 6, FPLC profiles of fractionated SIV-mac251 are shown for Gag p27 and cholesterol. The graphs demonstrate that, for a 1% DIPE delipidation, the concentration of gag p27 substantially diverges from the control at higher fraction numbers while the concentration of cholesterol is substantially lower than the control for nearly all fractions.

EXAMPLE 11

Monkeys Boosted with Delipidated HIV have Higher Ab Titers Compared to live HIV Boosted Group Four monkeys were primed with an equivalent of 5 ug p24 HIV-IIIB in incomplete Freund's Adjuvant. Monkeys were then separated into two groups of two monkeys. Group 1 (RIl & RFo) received 1 ug DIPE delipidated HIV-IIIB every month; group 2 (RFt & Rom) received 1 ug live HIV-IIIB every month. Cellular parameters were measured by immunocytochemistry. Staining was done at 7 days post boost, while Ab titers and neutralization Ab were taken at 4 weeks post boosting. Ab titers to whole HIV-IIIB lysate were measured. Group 1 animals (which received delipidated virus) had higher Ab titers than the two control monkeys in Group 2. Delipidated virus boosting enhanced Ab titers to the whole virion (data not shown).

Figure 12:
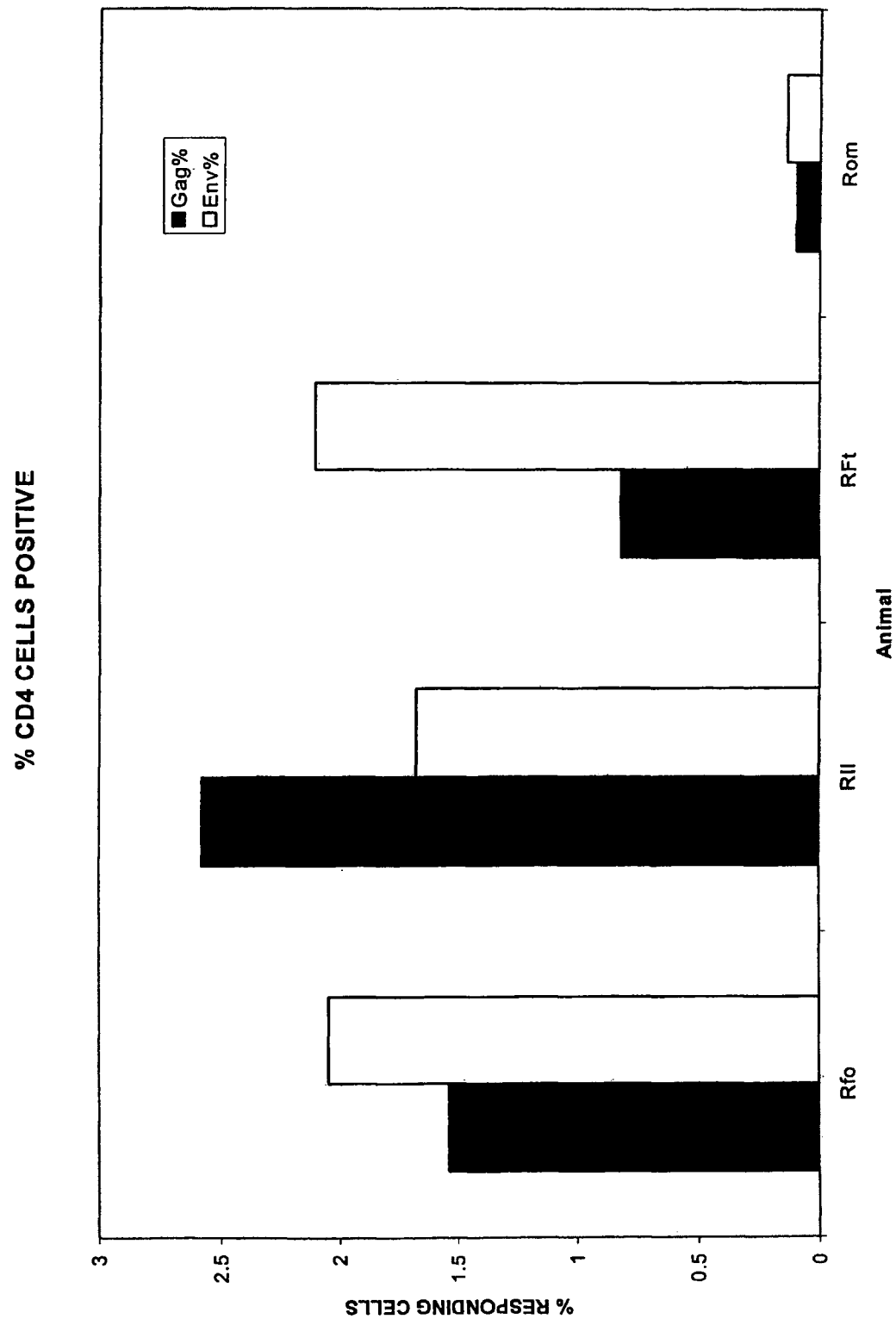
FIG. 12 presents the percentage of CD4+ cells immunoreactive for IFN gamma in response to gag or env peptide pools in four monkeys, each primed with an equivalent of 5 ug p24 HIV-IIIB in incomplete Freund's Adjuvant, and later boosted with 1 ug DIPE delipidated HIV-IIIB every month (RIl & RFo), or with 1 ug live HIV-IIIB every month (RFt & Rom).

Pooled CD4 T-cell responses to all the peptide pools are displayed in FIG. 12. Overall, animals showed a better response to ENV peptide pools than to GAG peptide pools. Both of the animals in Group 1 (RIl and RFo) had cumulative responses for Gag (>1.5%) and for Env (>1.5%). Only one animal in the control Group 2 (RFt) had an appreciable response to Gag (>0.5%) and for Env (>1.5%). The other control animal, Rom, had very low responses to the peptide pools.

Overall, monkeys given delipidated virus showed better cell mediated immune response (measured by ICC). The Ab data correlates well with the CD4+ ICC data. Animals show-

EXAMPLE 12

Dendritic Cells Exposed to Delipidated SIV Stimulate Enhanced CD4+ Proliferation Compared to Dendritic Cells Exposed to Live Virus PBMCs from a long term non-progressor monkey were employed. PBMCs were isolated using ficoll separation, and monocytes were cultured out using plastic adherence of $3 \times 10^7$ PBMC in 5 ml RPMI-10% FCS at 37° C. for 2 hrs. Non-adherent cells were removed and flasks gently washed with warm 1X PBS. Monocytes were incubated with 1000 U/ml IL-4 and 1000 U/ml of GM-CSF for 4 days in RPMI-15% FCS. This procedure generated immature dendritic cells (DC).

Immature DC ($2 \times 10^3$) were pulsed with 50 ng of AT-2 treated SIV, delipidated SIV (1% DIPE with end-over-end mixing for 20 min) or live SIV for 3 hr at 37° C. Cells were washed extensively to eliminate excess virus and were checked by SIVp27 for amount of residual virus. DC ($2 \times 10^3$) were resuspended for 3 days in R-15 with 100 U/ml TNF-a, IL-4, GM-CSF to induce DC maturation. Next, $2 \times 10^6$ peripheral blood lymphocytes (PBL) were added to the DC cultures, for 24-36 hr, before performing proliferation assay using the cyQUANT Cell Proliferation Assay Kit (Molecular Probes) [Note: CD8+ cells were depleted from the PBLs prior to use]. Proliferation assay performed according to manufacturer's protocol (cyQUANT-Molecular Probes). Briefly, cells were pelleted and the supernatant removed. The pellet was then frozen for about 1 hr, and 4X CyQUANT dye concentration added to the pellet. The supernatant of lysed cells was allowed to sit for about 10 min before reading a fluorescent plate at wavelengths of 480 for excitation and 520 for emission.

The % proliferation was calculated as follows: [(test proliferation-control proliferation)/(control proliferation)]×100. The control proliferation is the proliferation of PBMC+DC without adding the antigen to provide background noise.

Dendritic cells (DC) are powerful antigen presenting cells to the CD4, CD8, and CD20 B-cells. The results demonstrate that dendritic cells (DC) pulsed with delipidated SIV triggered a 16% better proliferative response in CD4+cells compared to DCs pulsed with live virus (208672 with delipidated virus vs 165616 with live virus). This strongly suggests a better antigen processing/presentation of the delipidated virus by the DC.

CD4 proliferation is a functional index of CD4 responses to a given epitope. It is more specific readout than IFN-γ secretion, since in HIV infected people, their CD4 cells produce IFN-γ, but do not proliferate in response to antigen.

Virus delipidated with the method of the present invention can increase proliferation of antigen specific CD4+ cells which leads to a more efficient maturation of the CD8+ cells and maturation of plasma cells (B-cells which produce antigen specific Ab). Since control of viral infection is dependent on CD4+ cellular proliferation, the method of the present invention provides an effective functional vaccine.

EXAMPLE 13

Delipidated Immunodeficiency Viruses as Autologous Therapeutic Vaccines

A cohort of highly viremic macaques chronically infected for over two years with SIVmac239 was used as a chronic and pathogenic model of immunodeficiency virus infection. The animals were identified as RDg-7, RJo-6, RMi-7 and RSp-6. To test the effect on these animals of administration of a delipidated immunodeficiency virus composition comprising modified, partially delipidated immunodeficiency viral particles, also referred to as therapeutic vaccine compositions or therapeutic vaccines, autologous immunodeficiency virus was delipidated and administered to the experimental animals following a 30 day antiretroviral therapy (ART) with an antiviral drug PMPA. The therapy resulted in viral loads of less than 80 copies/ml of viral RNA in the experimental animals. The animals were then subjected to lymph node targeted immunization at monthly intervals with 1, 1 and 10 μg of autologous delipidated SIV virus composition, obtained substantially as described elsewhere herein. Four weeks after the last boost, ART was discontinued and the animals were monitored for virological and immunological parameters.

Figure 13:
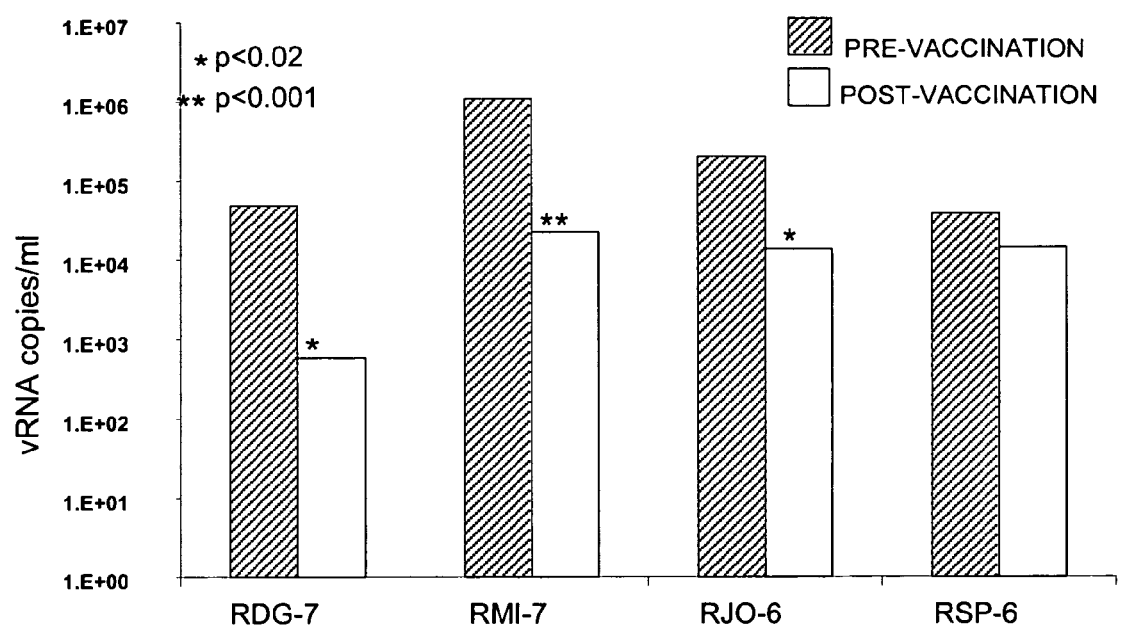
FIG. 13 is a schematic representation of plasma viral loads (vRNA copies/ml) before (pre-) and after (post-) administration of an autologous delipidated viral composition in a cohort of macaques (RDg-7, RMi-7, RJo-6 and RSp-6) chronically infected with SIV mac239. Pre-administration viral loads are averages of three data points before vaccination as shown in FIGS. 14-17. Post-administration viral loads are averages of last three available post-vaccination data points as shown in FIGS. 14-17.
Figure 14:
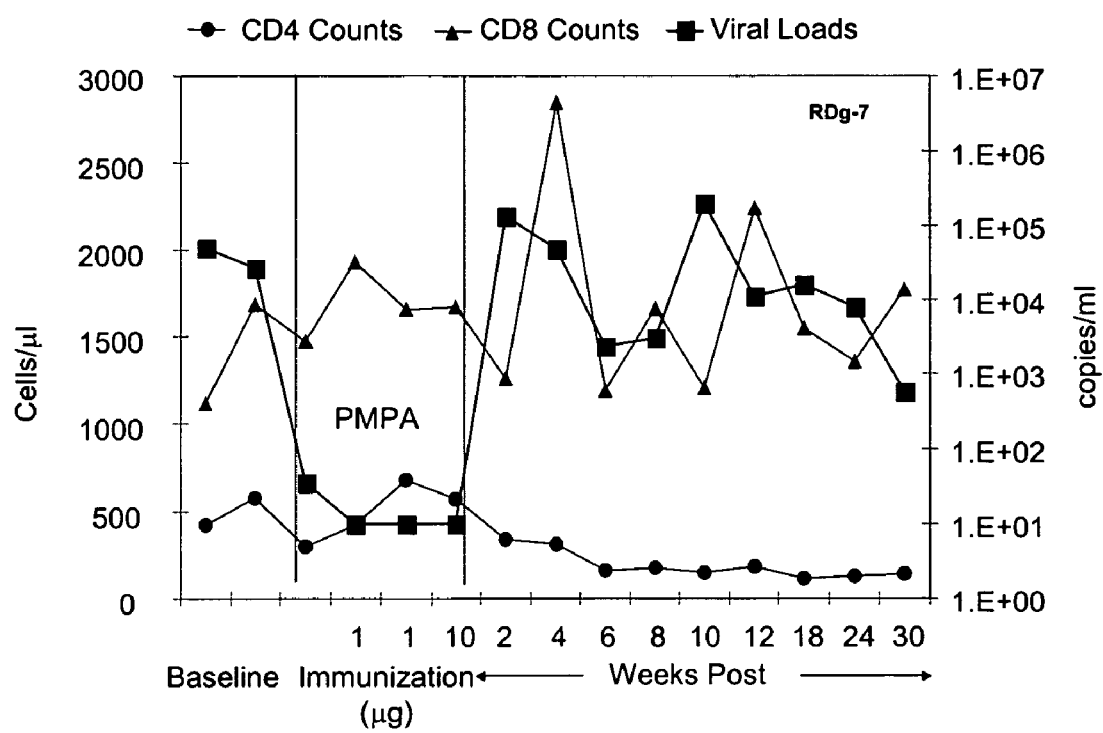
FIG. 14 is a schematic representation of virologic and immunologic parameter profiles in a macaque, RDg-7, chronically infected with SIV mac239 before and after administration of an autologous delipidated viral composition.
Figure 15:
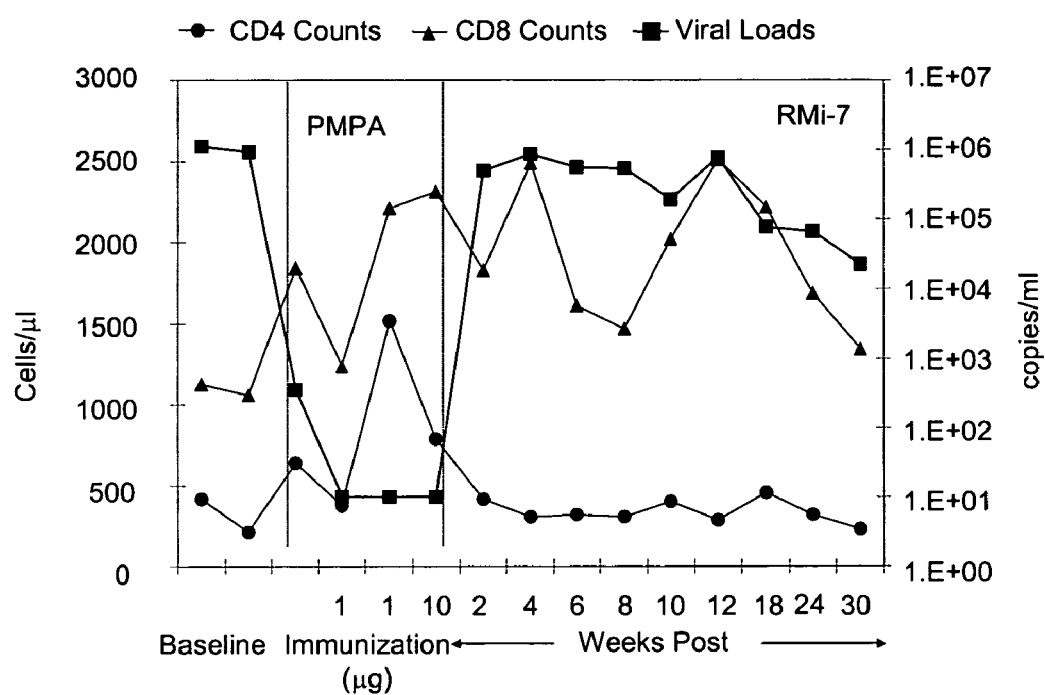
FIG. 15 is a schematic representation of virologic and immunologic parameter profiles in a macaque, RMi-7, chronically infected with SIV mac239 before and after administration of an autologous delipidated viral composition.
Figure 16:
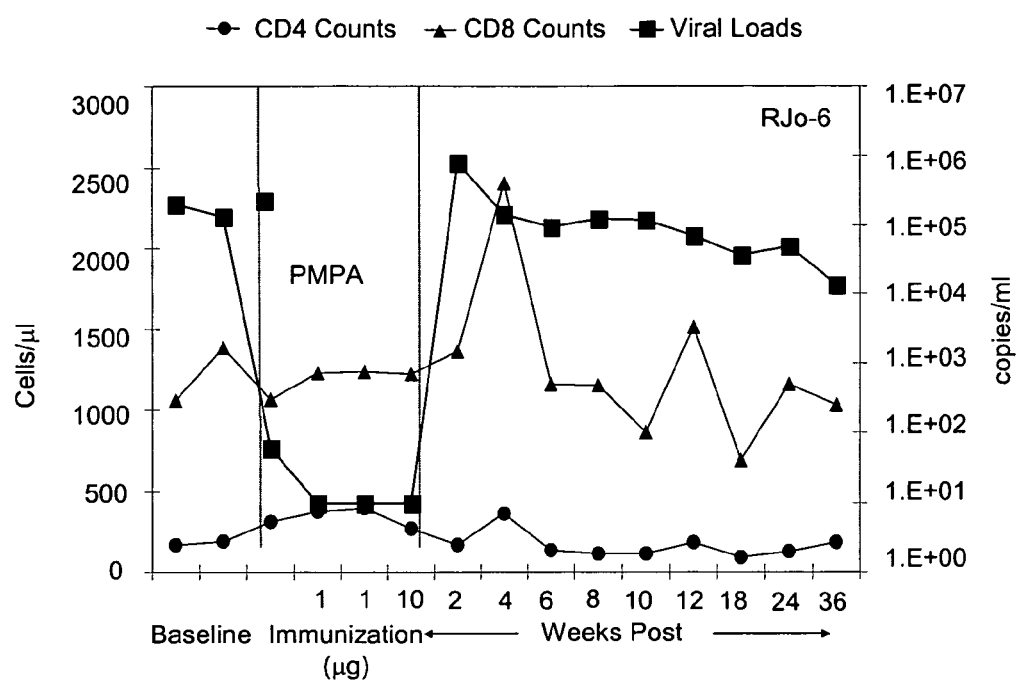
FIG. 16 is a schematic representation of virologic and immunologic parameter profiles in a macaque, RJo-6, chronically infected with SIV mac239 before and after administration of an autologous delipidated viral composition.
Figure 17:
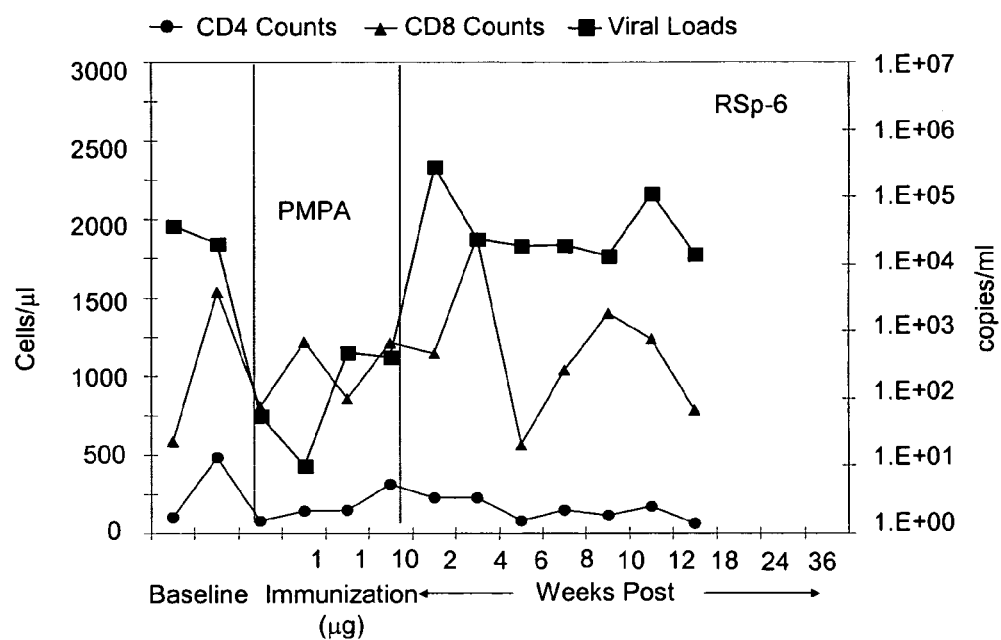
FIG. 17 is a schematic representation of virologic and immunologic parameter profiles in a macaque, RSp-6, chronically infected with SIV mac239 before and after administration of an autologous delipidated viral composition.
Figure 18:
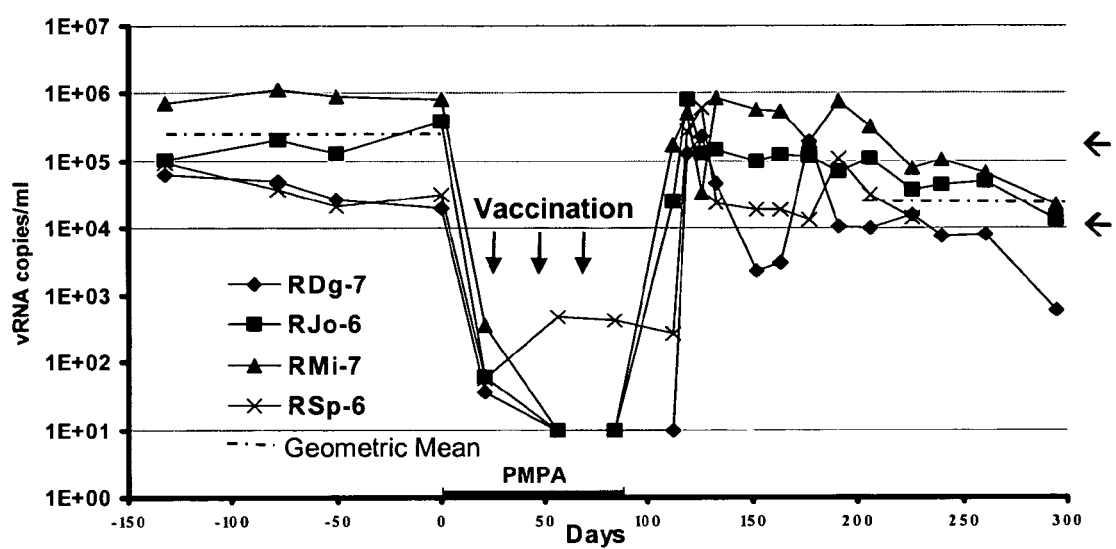
FIG. 18 is a schematic representation of viral loads in a cohort of macaques (RDg-7, Rmi-7, RJo-6 and RSp-6) chronically infected with SIV mac239 before and after administration of an autologous delipidated viral composition.

The virological and immunological parameters were determined substantially as follows. Viral loads, schematically shown in FIGS. 13-18, were analyzed by SIV enzyme immunoassay (EIA) substantially as described elsewhere herein. Briefly, serially diluted serum was added to microtiter plates adsorbed with SIVmac251, Env gp120 or Gag p55 antibodies. After washing, the plates were incubated with a HRP-anti mouse IgG Ab and developed with tetra-methylene blue (TMB) substrate. Plates were read at a 450 nm wavelength using an ELISA reader. As schematically shown in FIG. 13, pre-administration (pre-vaccination) rates are averages of the three viral load data points before vaccination as shown in FIGS. 14-17. Post-administration (post-vaccination) rates are averages of last three available post-vaccination data points as shown in FIGS. 14-17.

Figure 20:
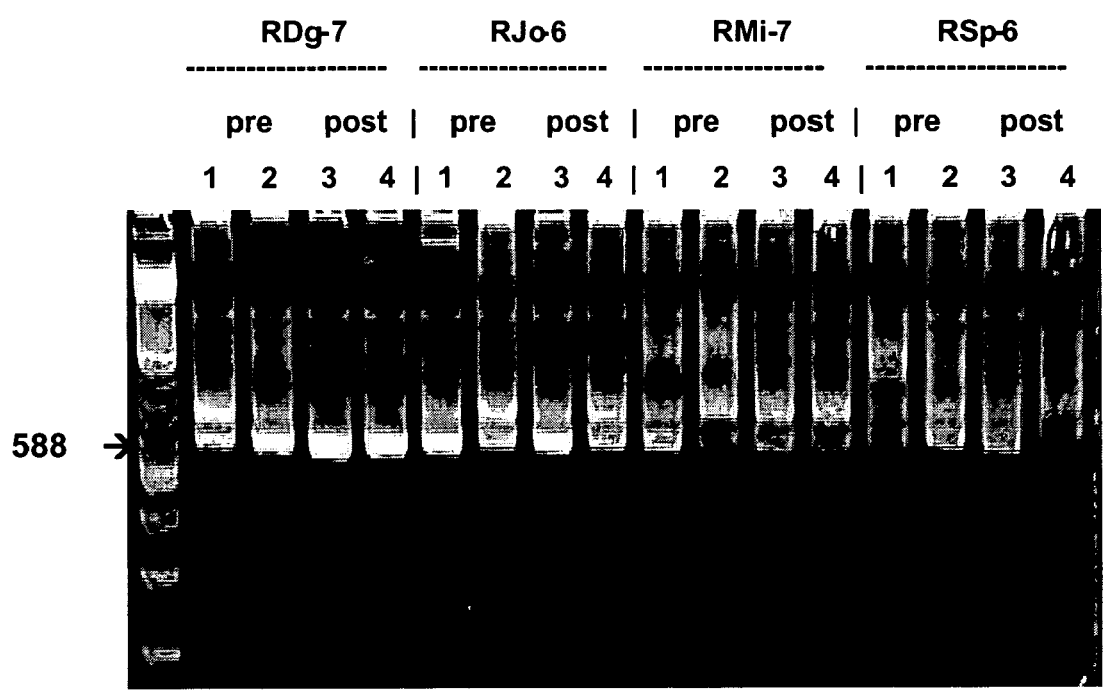
FIG. 20 is a photograph of gel-electrophoresis analysis of levels of Env-encoding nucleic acids determined by a heteroduplex-mobility shift assay in macaques chronically infected with SIV mac239 before (pre-) and after (post-) administration of an autologous delipidated viral composition.

Env nucleic acid levels were analyzed by heteroduplex-mobility shift assay (HMSA), with the results shown in FIG. 20. Briefly, a 588 bp Env sequence was amplified from viral RNA of 3 separate amplificates, denatured at 95° C., mixed together, placed on ice immediately to form heteroduplexes, and run on a non-denaturing 5% PAGE gel. The nucleic acid bands were visualized using ethidium bromide staining.

Peripheral blood mononuclear cells (PBMC) were subjected to short-term restimulation with overlapping peptides spanning the entire SIV Env and Gag proteins, followed by enumeration of IFN-γ producing PBMC by intracellular cytokine staining (ICC) by flow cytometry. Briefly, a 12 hour re-stimulation of $1 \times 10^6$ splenocytes with pools of peptides encompassing SIV Gag and Env, was performed. After Brefeldin A addition, the samples were stained for CD4, CD8, and intracellular IFN-γ, and the cells were analyzed using a FACS Calibur. The results of the immunological parameters determination are analyzed, for example, in FIGS. 14-17 and Tables 12-13.

As illustrated in FIGS. 14-18, PMPA treatment reduced plasma viral loads from $10^4$-$10^6$ to below the limits of detection (10 viral RNA copies/ml). Upon PMPA cessation, all animals exhibited initial viral rebound to pre-PMPA levels. Following administration, also referred to as vaccination, of the delipidated viral composition, all animals exhibited gradual decline of their viral loads. The difference in the viral loads in the experimental animals pre- and post-vaccination is illustrated in FIG. 13. At 7 months post PMPA cessation, all three surviving animals (RDg-7, RJo-6 and Rmi-7) exhibited statistically significant (p<0.02), ≧1 log reduction in viral loads.

As illustrated in FIGS. 14-17 and Tables 12-13, PMPA treatment of the experimental animals led to increases in absolute CD4 counts from pre-PMPA levels of<500/μl. Tables 12-13 show that administration of delipidated viral composition to the experimental animals, or vaccination, enhanced Gag and Env CD8 responses in the animals post-vaccination. PMPA cessation/viral rebound was accompanied by the appearance of several Gag and Env epitope pool responses. In particular, administration of delipidated viral composition to the macaques generated CD4 responses to a unique set of pools, as shown in Table 13, which were maintained throughout the study. PMPA cessation/viral rebound was accompanied by the reappearance of broad and potent CD4 responses to most Gag and Env peptide pools with significantly higher magnitude as compared to pre-PMPA levels. Absolute CD4 counts remained substantially stable in two out of the three experimental animals for the remaining duration of the study.

Figure 19:
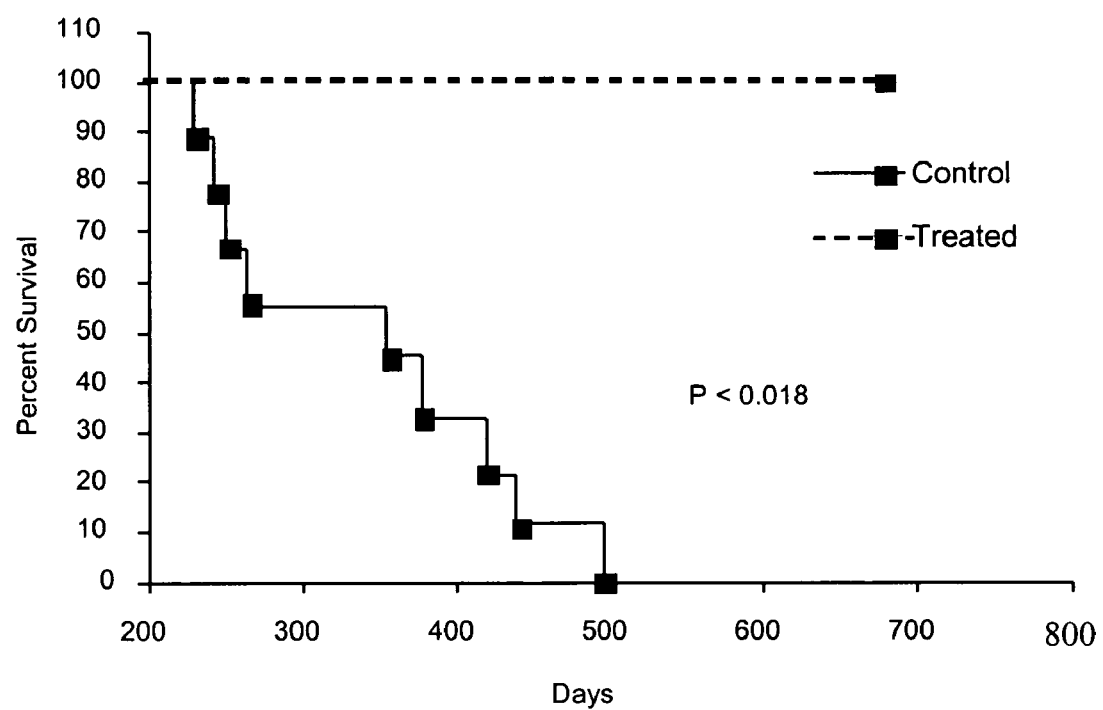
FIG. 19 is a Kaplan-Meier survival plot of macaques chronically infected with SIV mac239 after administration of an autologous delipidated viral composition as compared to a historical control cohort of macaques (average survival rates for a cohort are shown).

As illustrated in FIG. 19, Kaplan-Meier survival plot of the experimental animals showing average survival rates of experimental animals revealed statistically significant survival differences between the vaccinated cohort (survival rate of 100%) and a historical PMPA treated control group of animals (p<0.02).

As illustrated in FIG. 20, based on the reduction in diversity of sizes of viral RNA hybridizing to the Env probe, the heteroduplex mobility assay indicated reduction of viral diversity post-administration of the delipidated virus composition.

The results obtained from the monkey therapeutic vaccine animal model showed that T cell responses markedly diminished during ART, with only modest and transient increases observed following administration of delipidated viral composition, or therapeutic vaccine. However, all the macaques to whom the delipidated viral composition was administered showed markedly higher and broader T cell responses upon cessation of ART and return of viremia. Administration of the therapeutic vaccine, followed by PMPA cessation, resulted in marked increases in CD4 and CD8 T-cell peptide pool responses, significantly higher CD8 ICC IFNγ responses to Env, novel epitopes elicited in both CD4 and CD8 Env and Gag proteins and markedly lower viral diversity in three out of the four experimental macaques. The immunological responses resulted in diminution of viral loads in two out of the four macaques by 1 log or more as compared to pre ART viral loads. All animals maintained CD4 counts. T-cell and antibody responses against viral antigens were previously reported to control viremia in other models used for evaluation of immunodeficiency virus vaccines, such as HIV vaccine. Here, administration of the delipidated virus led to significant (>1 log) reduction of viral loads in three out of the four experimental animals and significant (p<0.02) enhancement of overall survival. The enhanced responses to autologous delipidated SIV and the reduction of viral loads and enhancement of survival in the experimental animals upon administration of the delipidated virus, as provided herein, support the use of delipidated immunodeficiency viral composition, such as delipidated HIV compositions, as a therapeutic vaccine administered to substantially enhance antibody and T-cell immune responses.

The experiments in the macaque animal modal discussed herein also demonstrated the added benefit of administering delipidated autologous virus vaccination during ART therapy. In the immunologically compromised animals (CD4<500/μl; viral loads>104 viral RNA (vRNA)/ml), administration of autologous delipidated virus, also referred to as vaccination, led to a significant reduction of viral loads, and a significant enhancement of survival. It has been previously reported that ART therapy alone does not provide such benefits. See, for example, Tryniszewska, E. et al. Vaccination of macaques with long-standing SIVmac251 infection lowers the viral set point after cessation of antiretroviral therapy. *Journal of Immunology*, v. 169, p. 5347 (2002).

Although not wishing to be bound by the following hypothesis, delipidated virus schematically illustrated in FIG. 21 may be processed and presented to the immune system more efficiently than AT-2 treated or live virus. In particular, delipidated virus tested in the experiments discussed herein may be more efficiently processed and presented by the antigen presenting cells (APC) resulting in significant T-cell and antibody responses. In the experimental animal model, T cell responses and control of viremia were improved at late immunodeficiency virus infection stages by administering low concentrations of delipidated virus. Thus, administration of the delipidated viral compositions comprising modified, partially delipidated immunodeficiency viral particles obtained by some embodiments of the methods discussed herein represents, in some of its aspects, a new method for therapeutic immunization and induction of immune response in animals or humans. In one aspect, compositions comprising modified, partially delipidated immunodeficiency viral particles obtained by the methods discussed herein and schematically illustrated in FIG. 21 represent an embodiment of a new composition for therapeutic immunization and induction of immune response in animals or humans infected by immunodeficiency viruses. These compositions are effective as therapeutic vaccines for prevention, attenuation, alleviation or treatment of an immunodeficiency virus infection and conditions associated with it, or for reduction of immunodeficiency viral loads in an animal or a human.

TABLE 12

T-Cell Peptide Pool Responses with Delipidated Virus

| | ENVELOPE | | | | GAG | | | |
|---|---|---|---|---|---|---|---|---|
| | CD4 | | CD8 | | CD4 | | CD8 | |
| ANIMAL ID | PRE | POST | PRE | POST | PRE | POST | PRE | POST |
| RDg | 6 | 13 | 8 | 15 | 9 | 15 | 6 | 16 |
| RJo | 1 | 5 | 10 | 15 | 1 | 4 | 5 | 14 |
| RMi | 1 | 11 | 10 | 14 | 5 | 15 | 8 | 12 |
| RSp | 1 | 4 | 14 | 17 | 1 | 15 | 7 | 11 |
| Geometric Mean | 2 | 7 | 10 | 15 | 3 | 11 | 6 | 13 |
| P-value | | 0.0281 | | 0.0075 | | 0.0245 | | 0.0009 |

PRE = pre-administration of delipidated virus (pre-vaccination);
POST = post-administration of delipidated virus (POST-vaccination)

TABLE 13

Novel Epitopes Elicited Post-Administration of Delipidated Virus

| | ENV | | | | | | GAG | | | | | |
|---|---|---|---|---|---|---|---|---|---|---|---|---|
| | CD4 | | | CD8 | | | CD4 | | | CD8 | | |
| Region | C1 | C2 | Gp 41 | C1 | C2 | Gp 41 | P9 | P17 | P27 | P9 | P17 | P27 |
| RDg-7 | X | X | X | | | | X | X | | | X | |
| RMi-7 | X | X | X | | X | X | X | X | | X | X | X |
| RJo-6 | X | X | X | X | X | X | | X | X | | | |
| RSp-6 | | | X | X | X | X | X | | X | X | X | X |

X indicates presence of a novel epitope

EXAMPLE 14

Characterization of Delipidated Retroviruses as Novel Therapeutic Vaccines

Embodiments of a novel solvent-based delipidation method disclosed herein were evaluated in the preparation of modified, partially delipidated immunodeficiency virus particles, such as HIV and SIV. The resulting modified, partially delipidated immunodeficiency viral particles delipidated by various solvent concentrations were evaluated for infectivity, by virus capture assay, electron microscopy (EM), isopyknic gradient centrifugation and by electrospray mass spectrometry (EM-SI). Examples of the delipidation conditions evaluated were delipidation with 1% DIPE, 1% butanol/DIPE, 1% butanol, 2% butanol and 5% butanol.

The virus capture assay was substantially performed as follows. Briefly, immunodeficiency virus (2 ng) was mixed with monoclonal antibodies (Mabs) against viral or host proteins and incubated for 1 hr on ice. Rabbit anti-mouse IgG was added for 1 hr, precipitated with *Staphylococcus aureus*, washed, lysed, and p24 levels were measured by ELISA substantially as described elsewhere herein.

Isopyknic gradient centrifugation was substantially performed as follows. Briefly, virus (10 µg/ml) was delipidated, pelleted through a 20% sucrose cushion, resuspended in 250 µl of TNE buffer and loaded onto 20% to 60% sucrose gradients. Fractions were collected from top to bottom and subjected to protein, p24 and Western blot analyses. The density gradients were confirmed by weighing duplicate 100 ml samples of fractions from control tubes.

Electron microscopy was substantially performed as follows. Briefly, concentrated HIV was directly pelleted or 20% sucrose pelleted. The virus pellets were fixed by adding EM-grade glutaraldehyde. The fixed pellets were then processed by postfixation with OsO$_4$. Ethanol dehydrated samples were embedded in epoxy resin and polymerized. Ultrathin sections were placed on copper grids, stained with uranyl acetate and lead hydroxide, and analyzed in a Philips transmission electron microscope. Images were captured with a digital camera at 1024×1024 pixel resolution, stored as TIFF files, and processed with Adobe Photoshop software.

Electrospray mass spectrometry was substantially performed as follows. Briefly, concentrated HIV-1 50 µg/ml (total protein) was mock treated or delipidated and pelleted (120,000×g, 1 hr). The pellets in PBS were mixed with chloroform/methanol (4:1) in a glass tube, vortexed, centrifuged and the upper phase removed. The solvent was removed with nitrogen and the samples stored at −20 degrees. 10 µl aliquots in methanol were injected into the EM-SI (API 150EX, LC/MS Systems, PE SCIEX) for analysis in positive ion mode.

The infectivity assay was substantially performed as follows. HIV-1 was diluted to 10 µg/ml in PBS, delipidated, pelleted, taken up in complete RPMI medium (cRMPI), and added to 200,000 LuSIV or TZN cells in the wells of a 96-well plate. Cells were lysed (24-36 hrs) and tested for luciferase activity.

The experimental results showed that HIV and SIV subjected to delipidation by less than 5% solvent retained both viral envelope proteins and envelope incorporated host proteins. Analysis by ELISA and virus capture indicated that both viral and host envelope proteins retained at least some of their native structure. HIV-1 delipidated by 1% solvent, for example, by 1% DIPE, substantially retained protein content and immunoreactivity as compared to control virus. HIV-1 delipidated by 5% solvent also showed a much higher p55 gag to total viral protein ratio than the HIV-1 delipidated by 1% solvent as determined by Western blot of HIV-1 proteins probed with a serum obtained from an HIV-infected human (results not shown). This indicated that the integrity of immunodeficiency virus was compromised by 5% solvent delipidation.

Figure 22:
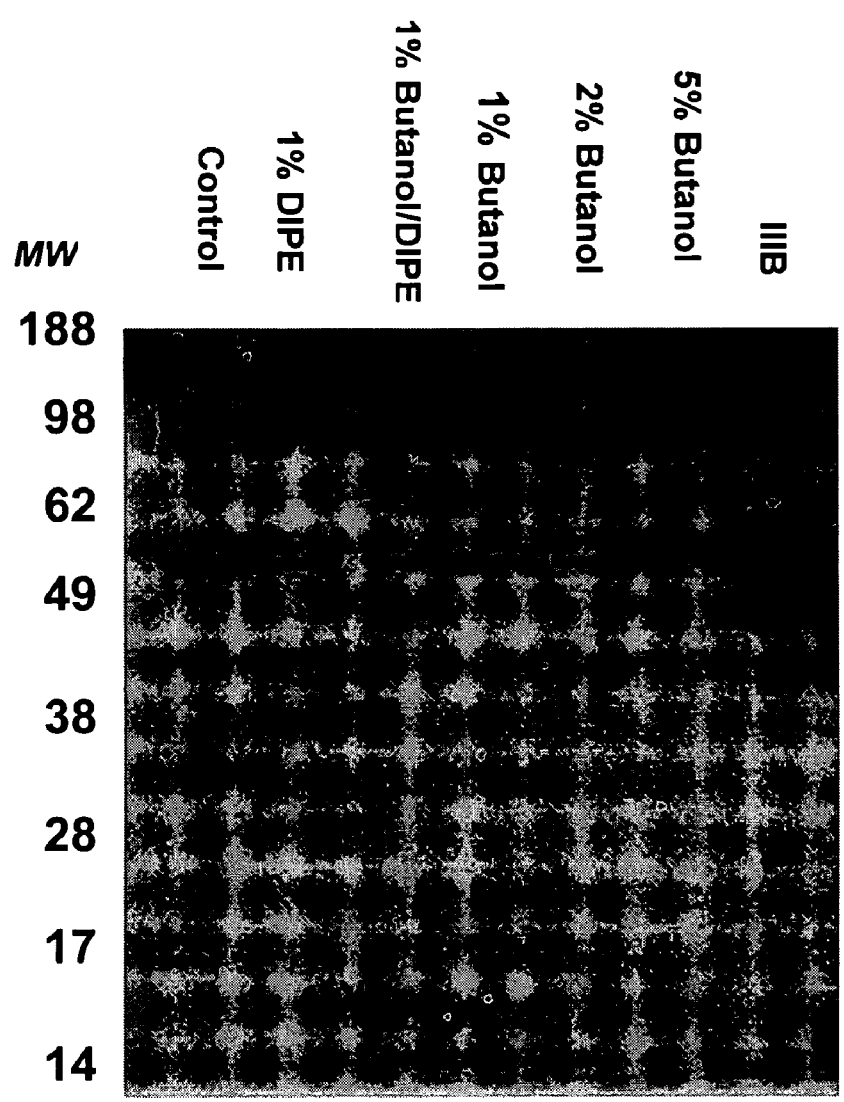
FIG. 22 is a anti-class I MHC (MHC I) Western blot of HIV-1 delipidated by 1% DIPE, 1% butanol, 1% butanol/DIPE, 2% butanol and 5% butanol.
Figure 23:
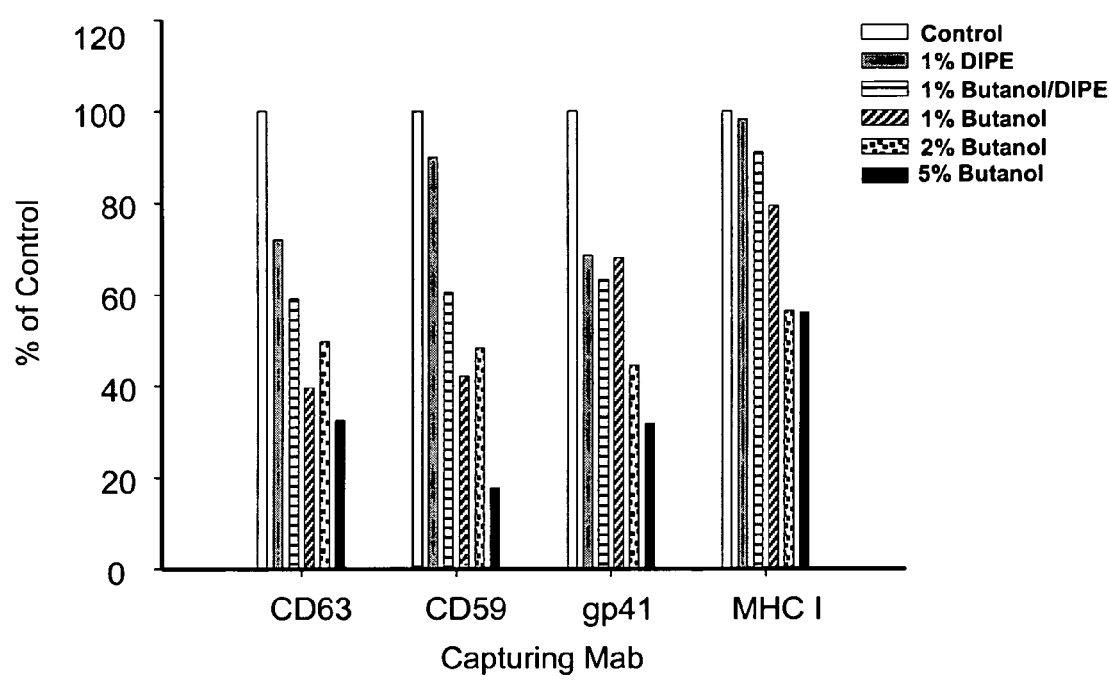
FIG. 23 is a schematic representation of a virus capture assay, using antibodies to CD63, CD59, gp41 and MHC I, of HIV-1 delipidated by 1% DIPE, 1% butanol, 1% butanol/DIPE, 2% butanol and 5% butanol.

HIV-1 delipidated with 2% or less solvent retained envelope incorporated host proteins and their conformations (see FIGS. 22-23). On the other hand, HIV-1 delipidated with 5% solvent exhibited significant changes in the host protein profile, with reductions, for example, in lipid raft membrane marker CD59. As the solvent concentration increased from 1% to 5%, the concentration of cellular proteins that are viral membrane bound, such as MHC-1, also dropped. Upon delipidation with 1% DIPE, the modified viral particles retained >95% of the cellular proteins, such as MHC-I, while delipidation with 5% butanol resulted in the levels of MHC-I undetectable by Western blot analysis, as shown in FIG. 22, indicating a substantial loss or significant modification of the protein. As illustrated in FIG. 23, when detected by the capture assay, delipidation with 1% DIPE resulted in the modified viral particles retaining >95% of the cellular proteins, such as MHC-I, while the virus delipidated by 5% butanol retained ≦40% of the cellular proteins, such as MHC-I. Other cellular and viral proteins reactivity, such as that of CD63, CD59 and gp41, was also substantially affected by delipidation with 5% butanol. Modified viral particles delipidated with 1% DIPE, on the other hand, retained ≧70% reactivity of these proteins.

Figure 24:
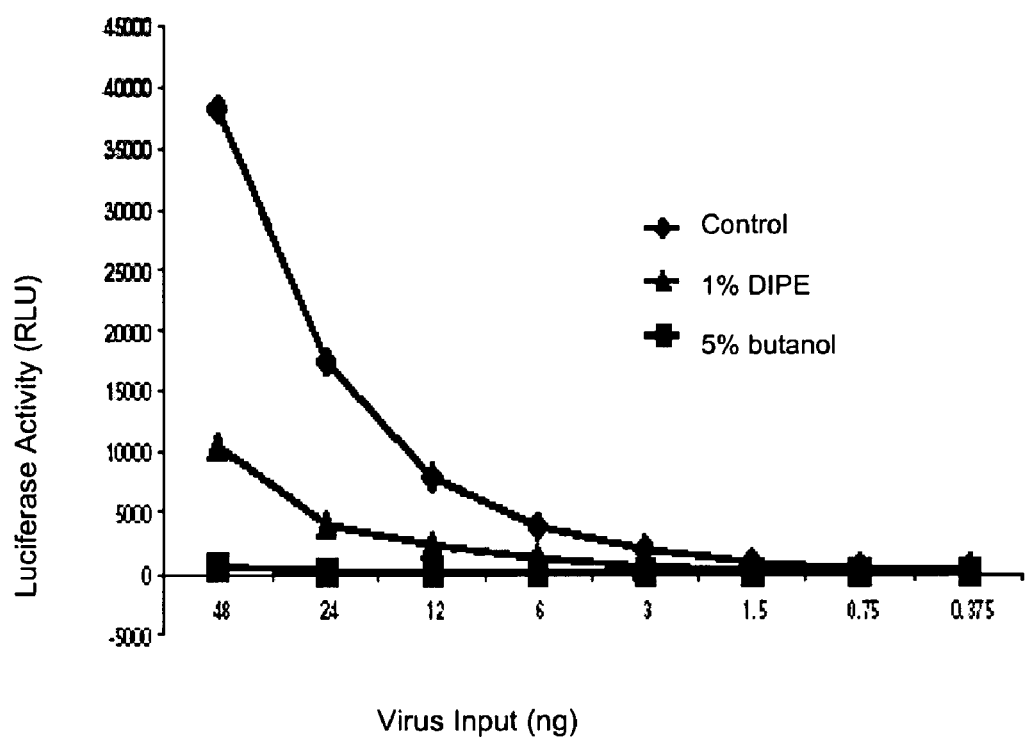
FIG. 24 is a schematic representation of results of an infectivity assay (measured as luciferase activity) for HIV-1 delipidated by 1% DIPE (▲) and 5% butanol (■), and control HIV-1 (●) not subjected to delipidation.
Figure 25:
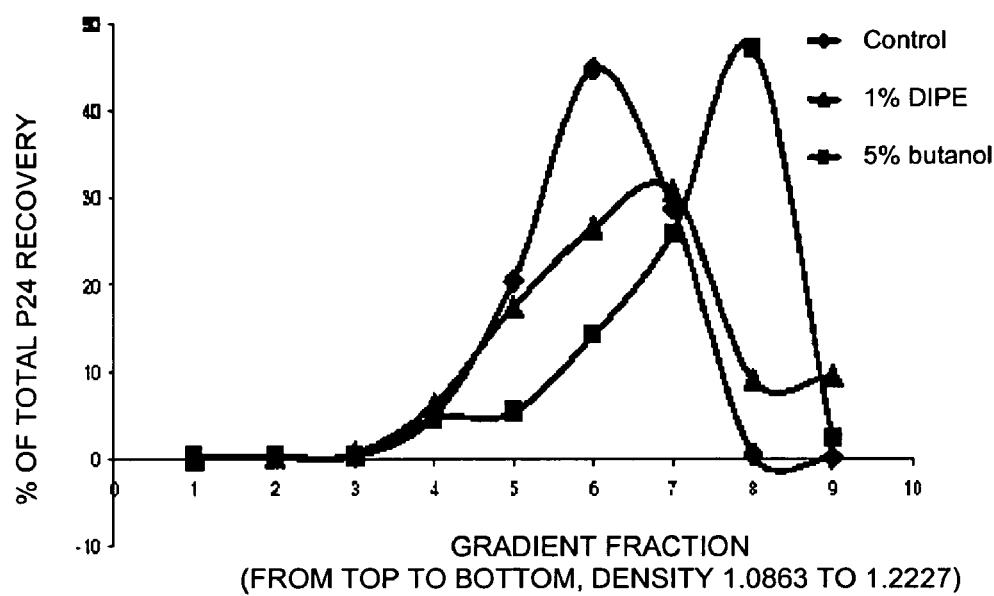
FIG. 25 is a schematic representation of results of an isopyknic gradient centrifugation assay for HIV-1 delipidated by 1% DIPE (▲) and 5% butanol (■), and control HIV-1 (●) not subjected to delipidation.
Figure 26:
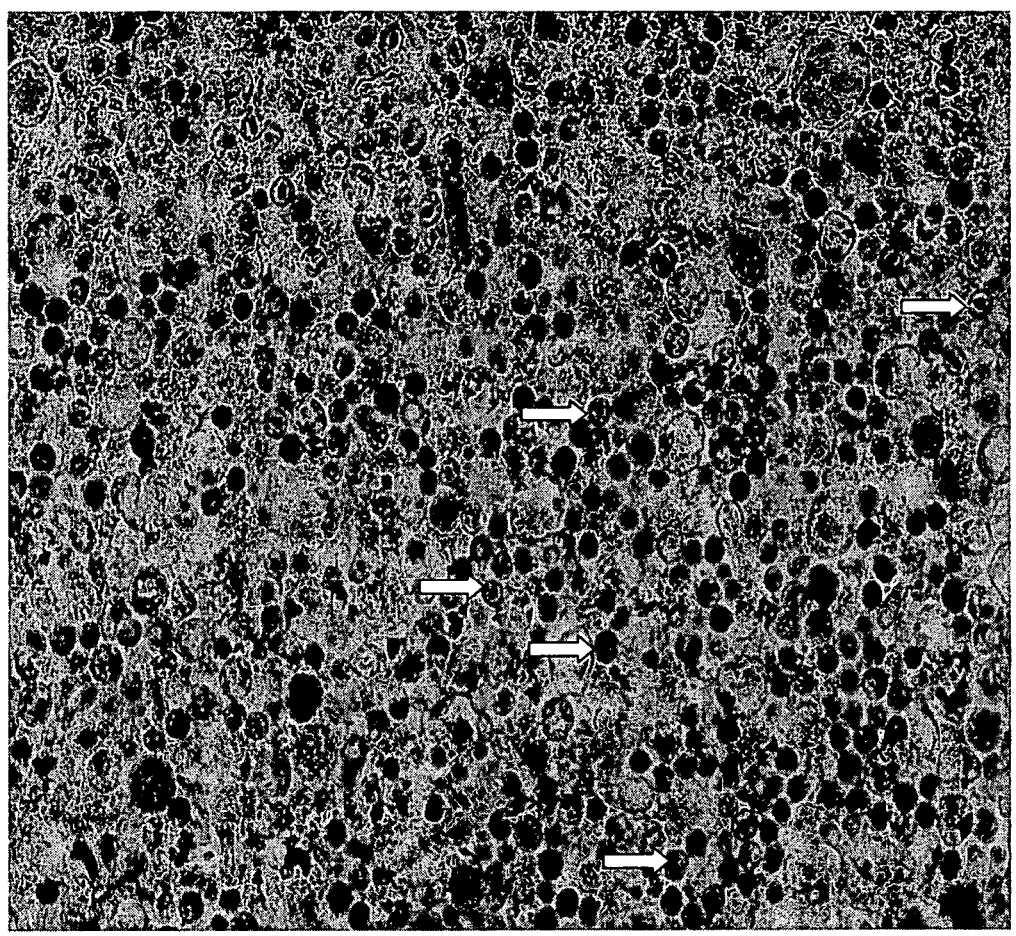
FIG. 26 is an electron micrograph of control HIV-1 particles not subjected to delipidation.
Figure 27:
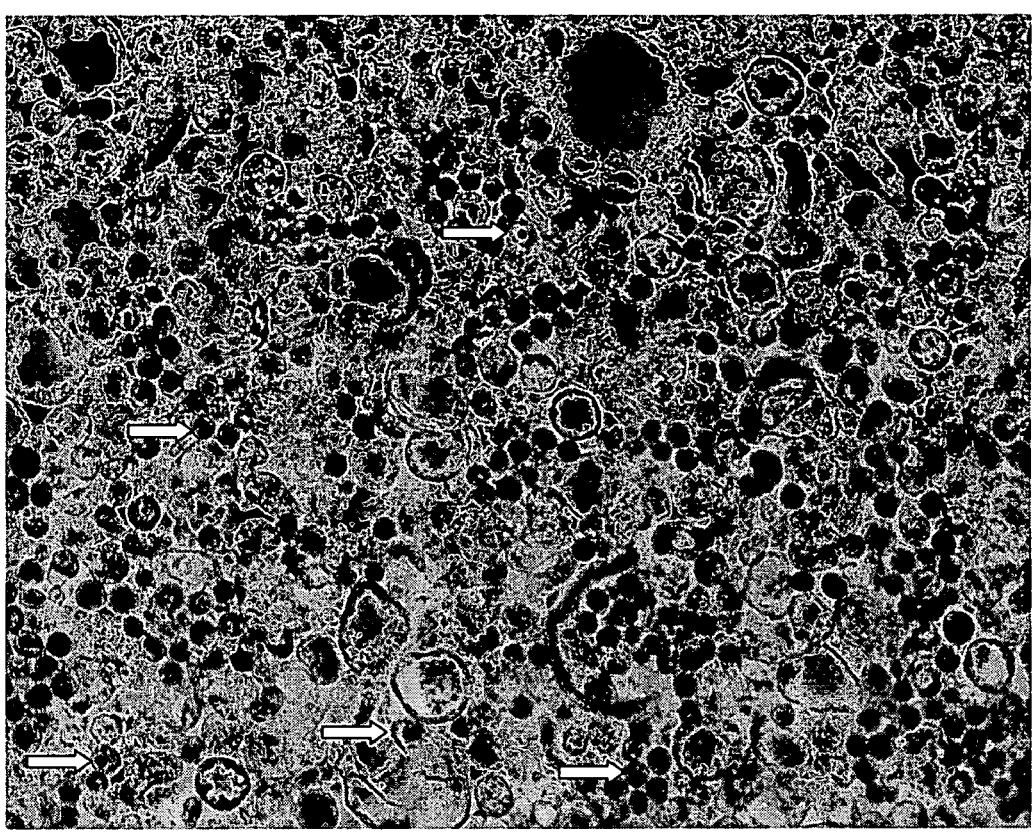
FIG. 27 is an electron micrograph of HIV-1 particles delipidated by 1% DIPE.
Figure 28:
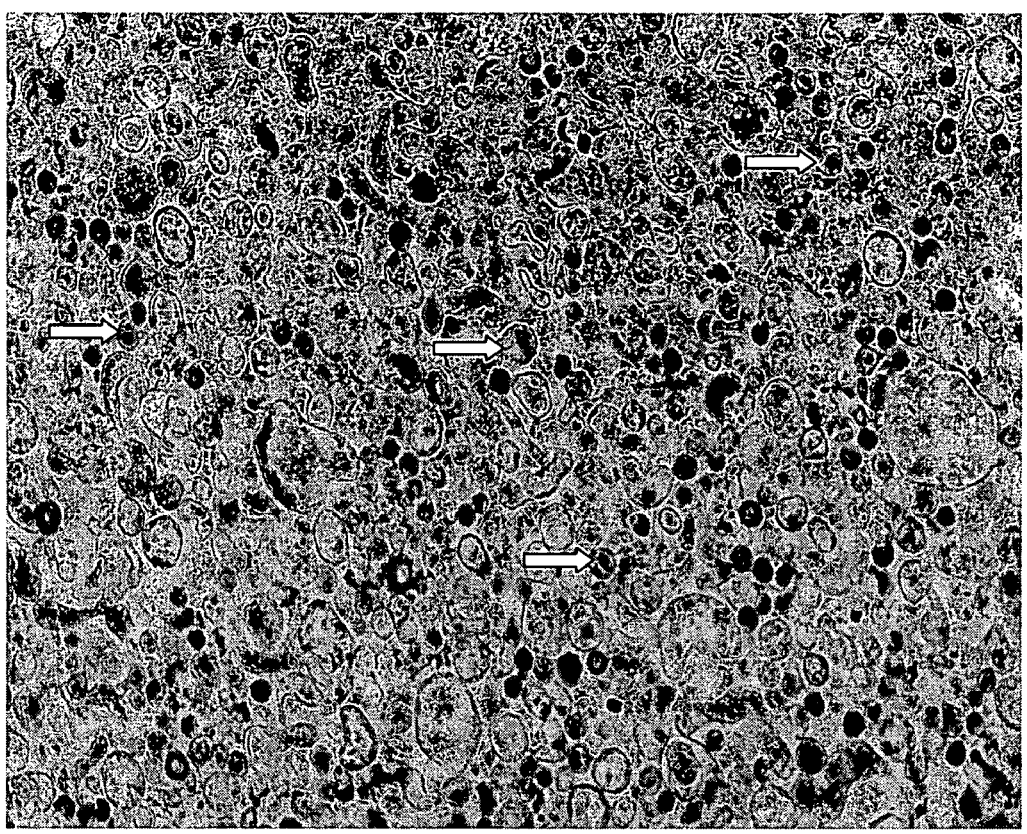
FIG. 28 is an electron micrograph of HIV-1 particles delipidated with 1% butanol.
Figure 29:
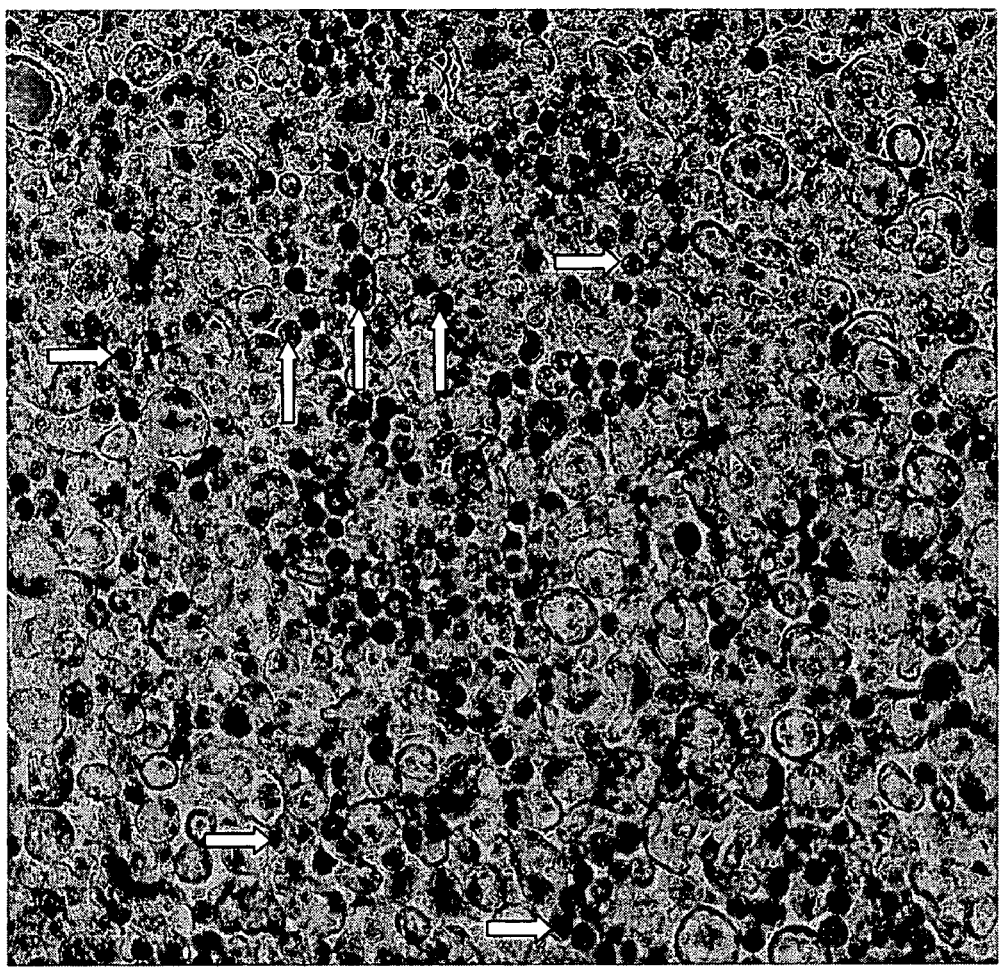
FIG. 29 is an electron micrograph of HIV-1 particles delipidated with 1% DIPE/butanol.
Figure 30:
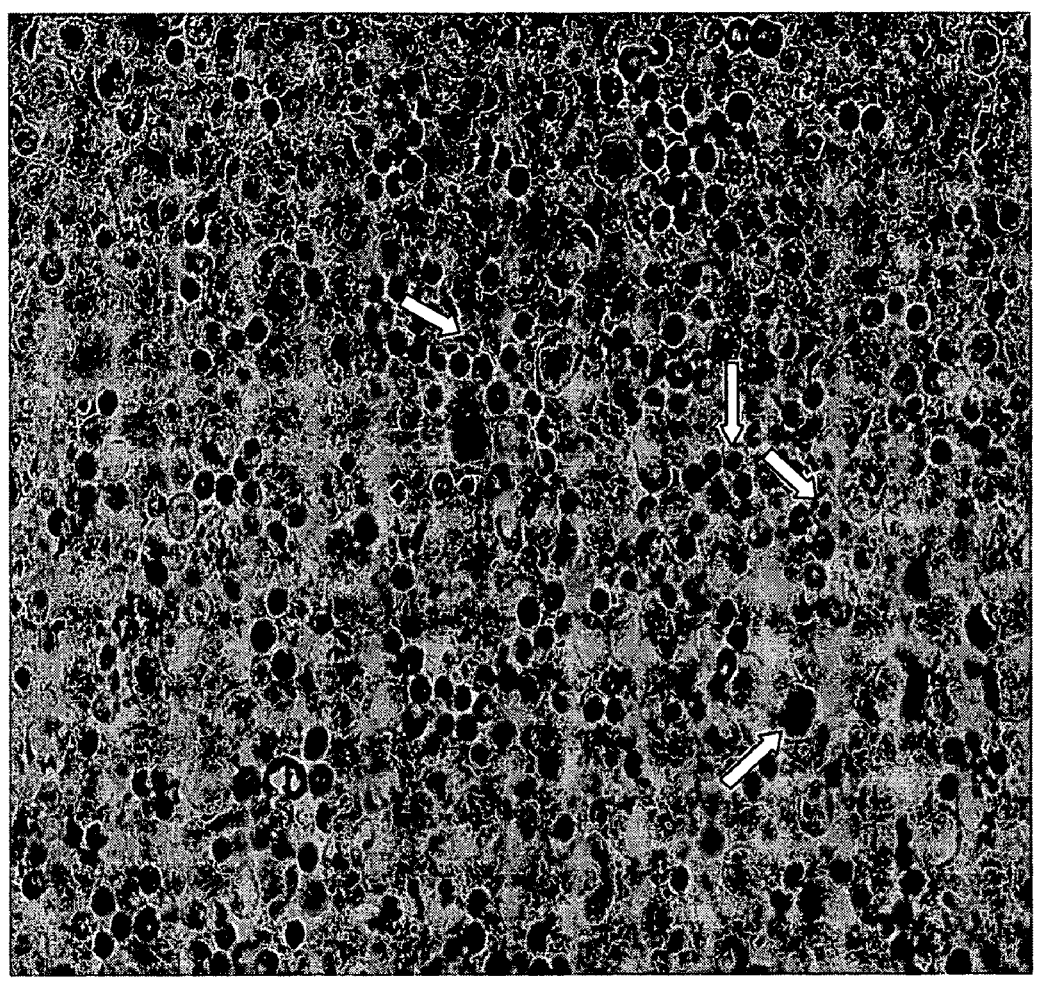
FIG. 30 is an electron micrograph of HIV-1 particles delipidated with 2% butanol.

Infectivity assays showed that subjecting immunodeficiency virus to the solvent-based delipidation protocol resulted in reduced infectivity of the modified viral particles. As illustrated in FIG. 24, delipidation reduced infectivity of HIV-1. Mildly delipidated HIV-1 exhibited residual infectivity at the highest virus input (48 ng).

Isopyknic studies on sucrose gradients revealed that the buoyancy of modified, partially delipidated particles decreased, as expected, from the loss of viral lipids. As illustrated in FIG. 25, density gradient analysis showed that HIV-1 equilibrated at a density of approximately 1.12, consistent with previously available data. Delipidating HIV-1 with 1% solvent increased its density, which is consistent with higher protein to lipid ratios and lower buoyancy. Delipidation with 5% butanol further increased the density of HIV-1, moving it to the bottom of the gradient.

Figure 31:
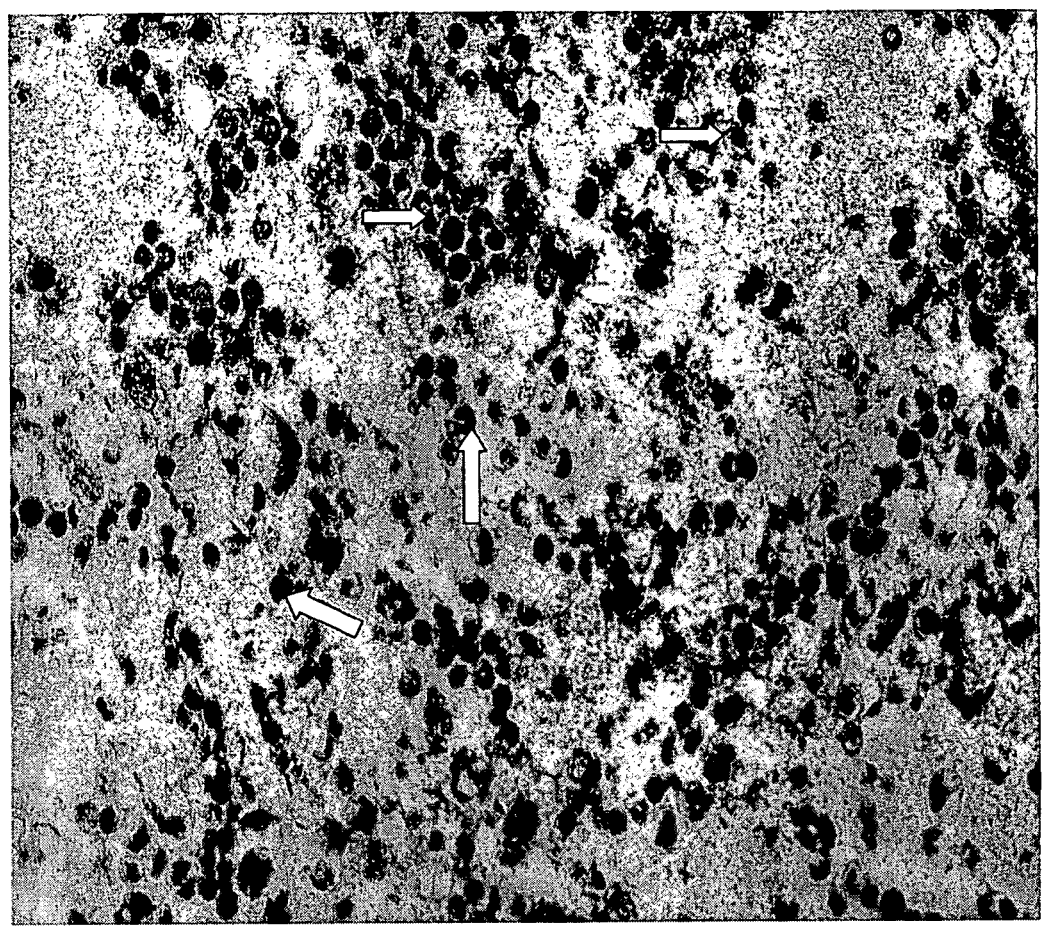
FIG. 31 is an electron micrograph of HIV-1 particles delipidated with 5% butanol.

Ultrastructural analysis by electron microscopy revealed that particles delipidated at low solvent concentrations retained their overall morphology. As illustrated in FIGS. 26-31, HIV-1 maintained its overall structure when delipidated with 1% solvent (see FIGS. 27-29, examples of viral particles indicated by arrows), however, the presence of vesicles and membranous material increased. The electron micrographs shown in FIGS. 27-30 show that, as compared to control HIV-1 not subjected to delipidation, a significant proportion of the viral envelopes were present following delipidation with 1% or 2% solvent (examples of viral particles indicated by arrows), resulting in partially delipidated particles comprising viral envelopes, including envelope proteins. In contrast, delipidation with 5% solvent destroyed viral envelopes, as shown in FIG. 31 (examples of viral cores indicated by arrows). HIV-1 delipidated with 5% solvent lost its overall structure, resulting in decreased membrane integrity and increased viral permeability.

Figure 32:
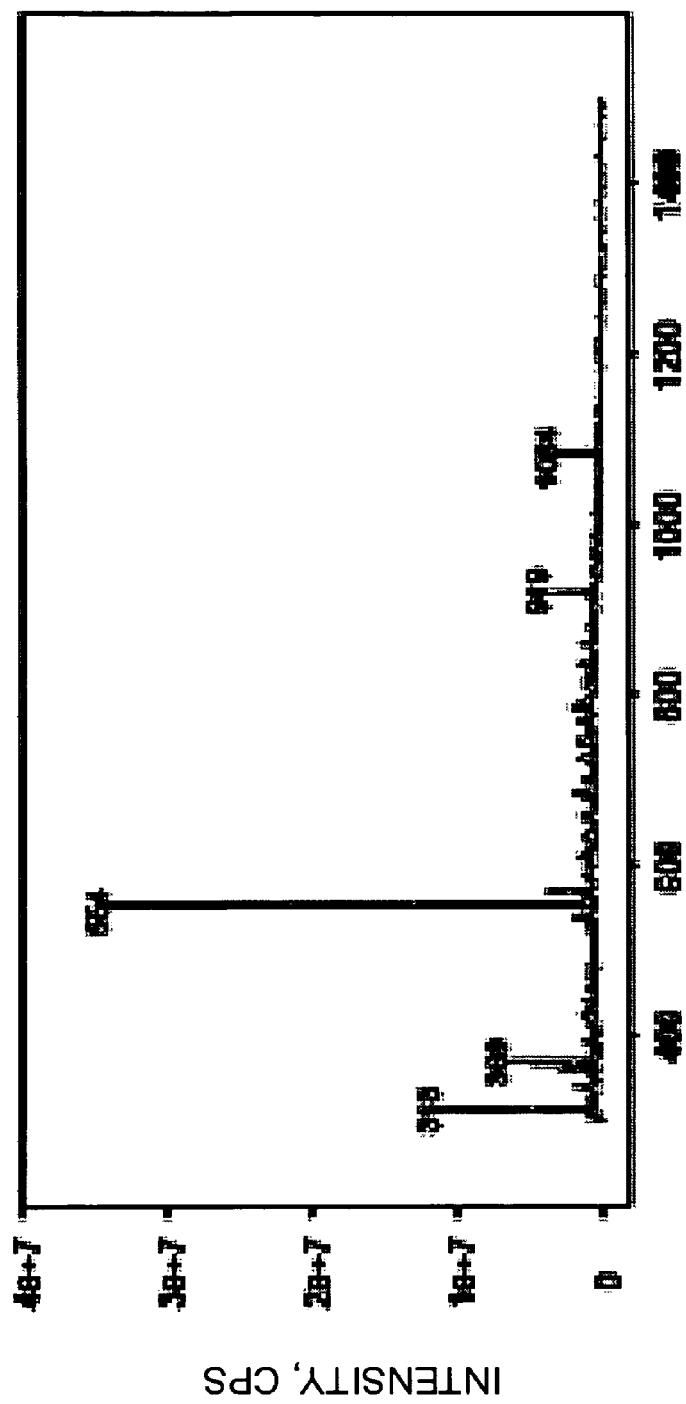
FIG. 32 is a schematic representation of ESI-MS analysis of delipidated with 1% DIPE HIV-1 particles.
Figure 33:
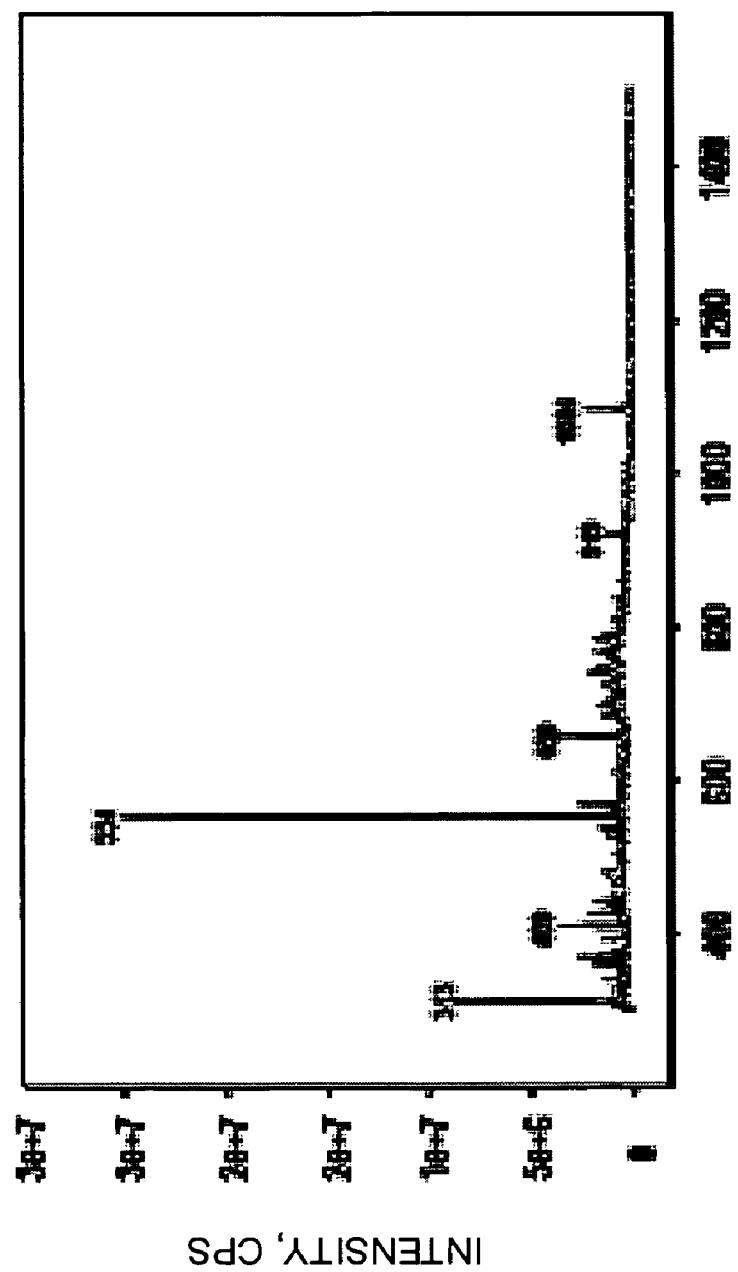
FIG. 33 is a schematic representation of ESI-MS analysis of delipidated with 5% butanol HIV-1 particles.
Figure 34:
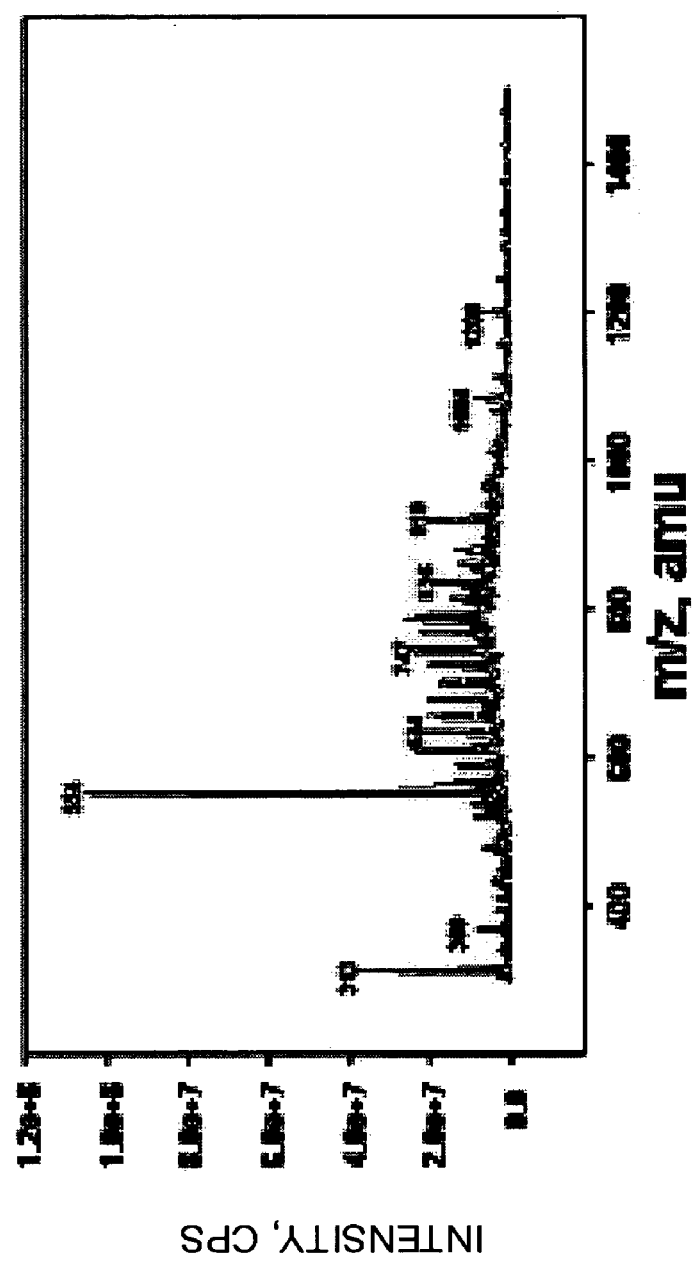
FIG. 34 is a schematic representation ESI-MS analysis of control HIV-1 particles not subjected to delipidation.

In reference to FIGS. 32-34, delipidation with 1% DIPE (FIG. 32) and with 5% butanol (FIG. 33) substantially changed the ESI-MS profile of the virus as compared to the control profile of a virus not subjected to delipidation (FIG. 34) by eliminating at least some of the major membrane lipid classes to levels undetectable by ESI-MS as performed herein (note the differences in the intensities on the axes). Lipid species at m/z 369 & 919 were more resistant to removal by delipidation. Major peaks at m/z 554 & 1084 appeared to represent solvent adducts. ESI-MS analysis confirmed substantial loss of lipids after delipidation and suggested preferential loss of some lipid species.

The results provided herein indicate that solvent-based delipidation protocol under certain delipidation conditions generated immunogenic virus particles that generally retained viral structure comprising an envelope and a core. For example, HIV-1 delipidated with 1-2% solvent retained the incorporated host membrane proteins, viral membranes, core proteins, and their conformations, as indicated by reactivity of the delipidated HIV-1 with monoclonal and polyclonal antibodies in immunoprecipitation and immunoblots. In contrast, with a solvent concentration of 5%, structural integrity of the immunodeficiency virus was compromised. Severely delipidated viruses exhibited disruption of viral integrity resulting in the loss of both viral envelope and host proteins. While not wishing to be bound by the following hypothesis, modified, partially delipidated immunodeficiency viral particles retain at least some of the viral envelope and may be taken up and processed more efficiently as compared to undelipidated immunodeficiency virus or immunodeficiency virus subject to delipidation conditions that destroy its envelope and associated proteins. Modified viral particle may also display the epitopes that are masked on untreated viruses.

All patents, publications and abstracts cited above are incorporated herein by reference in their entirety. It should be understood, of course, that the foregoing relates only to preferred embodiments of the present invention and that numerous modifications or alterations may be made therein without departing from the spirit and the scope of the invention as set forth in the appended claims.

---

I claim:

1. A process of creating a modified, partially delipidated immunogenic immunodeficiency viral particle of an immunodeficiency virus, comprising the steps of:

receiving an immunodeficiency virus in a fluid, exposing the immunodeficiency virus to a delipidation process, consisting essentially of treating the immunodeficiency virus with 0.5% to 2.5% organic solvent, wherein the organic solvent is not a detergent or surfactant, wherein the delipidation process decreases the lipid content of a viral envelope of the immunodeficiency virus.

2. The process of claim 1, wherein the immunodeficiency virus is SIV or HIV.

3. The process of claim 1, wherein the modified, partially delipidated viral particle contains at least 70% of immunoreactivity of the viral and host proteins as compared to the immunodeficiency virus not subjected to the delipidation process.

4. The process of claim 1, wherein the modified, partially delipidated viral particle contains at least 70% of immunoreactivity of MHC I, CD63, CD59 or gp 41 as compared to the immunodeficiency virus not subjected to delipidation.

5. The process of claim 1, wherein the organic solvent is an ether, an alcohol, or a combination thereof.

6. The process of claim 5, wherein the ether is diisopropyl ether and the alcohol is butanol.

7. The process of claim 1, wherein the immunodeficiency virus is from an animal or a human.

8. The process of claim 1, wherein the immunodeficiency virus is HIV-1 or HIV-2.

9. The process of claim 1, wherein the fluid is a biological fluid selected from the group consisting of blood, plasma, serum, lymphatic fluid, cerebrospinal fluid, peritoneal fluid, pleural fluid, and pericardial fluid.

10. The process of claim 1, wherein the fluid is a biological fluid selected from the group consisting of blood, plasma and serum.

11. The process of claim 1, wherein the organic solvent is selected from the group consisting of hydrocarbons, ethers, alcohols, phenols, esters, halohydrocarbons, halocarbons, amines, and combinations thereof.

12. The process of claim 1, wherein the organic solvent is diisopropyl ether.

13. The process of claim 1, wherein the organic solvent is a combination of diisopropyl ether and butanol.

14. The process of claim 11, wherein the ether is a $C_4$-$C_8$ containing ether selected from the group consisting of ethyl ether, diethyl ether, propyl ether, isopropyl ether, diisopropyl ether and combinations thereof.

15. The process of claim 5, wherein the alcohol and the ether are present in a ratio of alcohol to ether of from about 0.01:99.99 to about 60:40.

16. The process of claim 5, wherein the alcohol and the ether are present in a ratio of alcohol to ether of from about 10:90 to about 5:95.

17. The process of claim 5, wherein the alcohol and the ether are present in a ratio of alcohol to ether of from about 10:90 to about 50:50.

18. The process of claim 5, wherein the alcohol and the ether are present in a ratio of alcohol to ether of from about 20:80 to about 45:55.

19. The process of claim 5, wherein the alcohol and the ether are present in a ratio of alcohol to ether of about 25:75.

20. The process of claim 5, wherein the ether is diethyl ether and the alcohol is butanol.

* * * * *